(12) United States Patent
Zheng et al.

(10) Patent No.: US 9,041,938 B2
(45) Date of Patent: *May 26, 2015

(54) SURFACE WAVE ASSISTED STRUCTURES AND SYSTEMS

(75) Inventors: Guoan Zheng, Pasadena, CA (US); Xiquan Cui, San Jose, CA (US); Xin Heng, Berkeley, CA (US); Changhuei Yang, Pasadena, CA (US); Axel Scherer, Woodstock, VT (US)

(73) Assignee: California Institute of Technology, Pasadena, CA (US)

( * ) Notice: Subject to any disclaimer, the term of this patent is extended or adjusted under 35 U.S.C. 154(b) by 381 days.

This patent is subject to a terminal disclaimer.

(21) Appl. No.: 13/344,550

(22) Filed: Jan. 5, 2012

(65) Prior Publication Data

US 2012/0250027 A1    Oct. 4, 2012

Related U.S. Application Data

(63) Continuation-in-part of application No. 12/792,059, filed on Jun. 2, 2010, now Pat. No. 8,189,204, which is a continuation-in-part of application No. 11/743,581, filed on May 2, 2007, now Pat. No. 7,768,654.

(Continued)

(51) Int. Cl.
*G01B 9/02* (2006.01)
*G02B 6/122* (2006.01)
*B82Y 20/00* (2011.01)
(Continued)

(52) U.S. Cl.
CPC ............... *G02B 6/1226* (2013.01); *B82Y 20/00* (2013.01); *G01N 21/554* (2013.01); *G02B 5/008* (2013.01); *G02B 21/0032* (2013.01); *G02B 21/004* (2013.01); *G02B 21/0056* (2013.01);
(Continued)

(58) Field of Classification Search
CPC .. G02B 21/14; G02B 21/004; G02B 21/0032; G02B 21/0056; G02B 5/008; G02B 5/0294
USPC ......................................................... 356/521
See application file for complete search history.

(56) References Cited

U.S. PATENT DOCUMENTS

| | | | |
|---|---|---|---|
| 4,981,362 | A | 1/1991 | DeJong et al. |
| 5,196,350 | A | 3/1993 | Backman et al. |

(Continued)

FOREIGN PATENT DOCUMENTS

| | | |
|---|---|---|
| EP | 1 371 965 | 12/2003 |
| JP | 2003-207454 A | 7/2003 |

(Continued)

OTHER PUBLICATIONS

United States Patent and Trademark Office (USPTO) Office Action in U.S. Appl. No. 11/743,581 dated on May 22, 2009.

(Continued)

*Primary Examiner* — Jonathan Hansen
(74) *Attorney, Agent, or Firm* — Sheila Martinez-Lemke; Weaver Austin Villeneuve & Sampson LLP

(57) ABSTRACT

A surface wave assisted system having an aperture layer with a surface and an aperture, and a plurality of grooves around the aperture. The plurality of grooves is configured to generate an optical transfer function at the aperture by inducing a surface wave for interfering with transmission of light of a range of spatial frequency.

21 Claims, 35 Drawing Sheets

Related U.S. Application Data

(60) Provisional application No. 60/796,997, filed on May 2, 2006, provisional application No. 60/796,996, filed on May 2, 2006, provisional application No. 61/183,868, filed on Jun. 3, 2009, provisional application No. 61/345,018, filed on May 14, 2010, provisional application No. 61/430,690, filed on Jan. 7, 2011.

(51) Int. Cl.
*G01N 21/552* (2014.01)
*G02B 5/00* (2006.01)
*G02B 21/00* (2006.01)
*G02B 21/14* (2006.01)
*G02B 27/52* (2006.01)

(52) U.S. Cl.
CPC .......... *G02B21/0068* (2013.01); *G02B 21/14* (2013.01); *G02B 27/52* (2013.01)

(56) References Cited

U.S. PATENT DOCUMENTS

| | | | |
|---|---|---|---|
| 5,362,653 A | 11/1994 | Carr et al. | |
| 5,426,505 A | 6/1995 | Geiser et al. | |
| 5,973,316 A | 10/1999 | Ebbesen et al. | |
| 6,499,499 B2 | 12/2002 | Dantsker et al. | |
| 6,858,436 B2 | 2/2005 | Zenhausern et al. | |
| 7,045,781 B2 | 5/2006 | Adamec et al. | |
| 7,250,598 B2 | 7/2007 | Hollingsworth et al. | |
| 7,271,885 B2 | 9/2007 | Schermer | |
| 7,283,229 B2 | 10/2007 | Noguchi et al. | |
| 7,751,048 B2 | 7/2010 | Yang et al. | |
| 7,768,654 B2 | 8/2010 | Cui et al. | |
| 7,773,227 B2 | 8/2010 | Yang et al. | |
| 7,982,883 B2 | 7/2011 | Cui et al. | |
| 8,189,204 B2 * | 5/2012 | Cui et al. | 356/521 |
| 8,411,282 B2 | 4/2013 | Cui et al. | |
| 2003/0142291 A1 | 7/2003 | Padmanabhan et al. | |
| 2003/0174992 A1 | 9/2003 | Levene et al. | |
| 2003/0203502 A1 | 10/2003 | Zenhausern et al. | |
| 2004/0156610 A1 | 8/2004 | Charlton et al. | |
| 2004/0175734 A1 | 9/2004 | Stahler et al. | |
| 2004/0190116 A1 * | 9/2004 | Lezec et al. | 359/298 |
| 2004/0224380 A1 | 11/2004 | Chou et al. | |
| 2005/0161594 A1 | 7/2005 | Hollingsworth et al. | |
| 2005/0271548 A1 | 12/2005 | Yang et al. | |
| 2006/0003145 A1 | 1/2006 | Hansen et al. | |
| 2006/0013031 A1 | 1/2006 | Ravkin et al. | |
| 2007/0172745 A1 * | 7/2007 | Smith | 430/5 |
| 2007/0207061 A1 | 9/2007 | Yang et al. | |
| 2007/0258096 A1 | 11/2007 | Cui et al. | |
| 2009/0073434 A1 * | 3/2009 | Kim et al. | 356/317 |
| 2009/0225319 A1 | 9/2009 | Lee et al. | |
| 2009/0276188 A1 | 11/2009 | Cui et al. | |
| 2010/0195873 A1 | 8/2010 | Cui et al. | |
| 2010/0290049 A1 | 11/2010 | Yang et al. | |
| 2010/0296094 A1 | 11/2010 | Yang et al. | |
| 2010/0309457 A1 | 12/2010 | Cui et al. | |
| 2011/0063623 A1 | 3/2011 | Cui et al. | |
| 2011/0075254 A1 | 3/2011 | Cui et al. | |
| 2011/0170105 A1 | 7/2011 | Cui et al. | |
| 2011/0181884 A1 | 7/2011 | Cui et al. | |
| 2012/0026509 A1 | 2/2012 | Cui et al. | |

FOREIGN PATENT DOCUMENTS

| | | |
|---|---|---|
| JP | 2003-0524779 A | 8/2003 |
| JP | 2004-505272 A | 2/2004 |
| WO | WO 02/10713 A2 | 2/2002 |
| WO | WO 2004/038484 | 5/2004 |
| WO | WO 2005/121749 | 12/2005 |
| WO | WO 2008/112416 | 9/2008 |

OTHER PUBLICATIONS

United States Patent and Trademark Office (USPTO) Final Office Action in U.S. Appl. No. 11/743,581 dated on Dec. 3, 2009.
United States Patent and Trademark Office (USPTO) Notice of Allowance in U.S. Appl. No. 11/743,581 dated on Mar. 26, 2010.
United States Patent and Trademark Office (USPTO) Notice of Allowance in U.S. Appl. No. 12/823,201 dated on Mar. 1, 2011.
United States Patent and Trademark Office (USPTO) Notice of Allowance in U.S. Appl. No. 12/823,201 dated on Mar. 11, 2011.
United States Patent and Trademark Office (USPTO) Office Action in U.S. Appl. No. 13/157,245 dated on Dec. 6, 2011.
United States Patent and Trademark Office (USPTO) Notice of Allowance in U.S. Appl. No. 13/157,245 dated on Aug. 23, 2012.
U.S. Allowed Claims for U.S. Appl. No. 13/157,245 dated on Dec. 3, 2012.
United States Patent and Trademark Office (USPTO) Notice of Allowance in U.S. Appl. No. 13/157,245 dated on Dec. 3, 2012.
United States Patent and Trademark Office (USPTO) Notice of Allowance in U.S. Appl. No. 12/792,059 dated on Dec. 14, 2011.
"Differential interference contrast microscopy," Wikipedia, last modified Feb. 10, 2009, downloaded from the Internet at http://en.wikipedia.org/wiki/Differential interference contrast microscopy on Mar. 31, 2009, 4pp.
"Fresnel number," Wikipedia, last modified May 2, 2010, 2pp.
"Surface Plasmon," Wikipedia, last modified Apr. 4, 2010, 7pp.
Adams, Mark L., et al., (2003) "Microfluidic Integration on detector arrays for absorption and fluorescence micro-spectrometers," *Sensors and Actuators A*, 104:25-31.
Aigouy, L., et al., (2007) "Near-field analysis of surface waves launched at nanoslit apertures," *Physical Review Letters*, 98:153902.
Arnison, M. R., et al., (Apr. 2004) "Linear Phase Imaging Using Differential Interference Contrast Microscopy," *Journal of Microscopy*, 214(Part. I):7-12.
Barnes et al., (2003) "Surface plasmon subwavelength optics," *Nature*, 424:824-830.
Beebe, David J., et al., (2002) "Physics and Applications of Microfluidics in Biology," *Annu. Rev. Biomed., Eng.*, 4:261-286.
Bethe, H.A., (1944) "Theory of Diffraction by Small Holes," *The Physical Review*, 66(7-8):163-182.
Biddiss, Elaine, et al., (2004) "Hetergeneous Surface Charge Enhanced Micromixing for Electrokinetic Flows," *Anal. Chem.*, 76:3208-3213.
Boppart, S. A., et al., (1997) "Forward-imaging instruments for optical coherence tomography," *Optics Letters*, 22:1618-1620.
Bouwkamp, C. J., (1954) "Diffraction theory," *Reports on Progress in Physics* XVIII, pp. 35-100.
Cao, Jinhua, et al., (2004) "Brownian Particle Distribution in Tube Flows," *Proceedings of IMECE04*, 260:243-252.
Chen, L., et al. (2006) "Role of radiation and surface plasmon polaritons in the optical interactions between a nano-slit and a nano-groove on a metal surface," *Optics Express*, 14:12629-12636.
Cheng, Ya, et al., (2004) "Microfluidic laser embedded in glass by three-dimensional femtosecond laser microprocessing," *Optics Letters*, 29(17):2007-2009.
Chronis, Nikolas, et al., (2004) "Total internal reflection-based biochip utilizing a polymer-filled cavity with a micromirror sidewall," *Miniaturisation for Chemistry, Biology & Bioengineering, Lab Chip*, 4:125-130.
Courjon, Daniel, (2003) "Near-field Microscopy and near-field optics," *Imperial College Press*, 317 pages.
Cui, X. et al., (Jan. 2006) "Portable Optical microscope-on-a-chip," *Photonics West*, San Jose, CA, 9pp.
Cui, Xiquan, et al., (Jan. 2006) "Portable optical microscope-on-a-chip," *Proc. SPIE*, 6095:609509-1-609509-8.
Cui, Xiquan, et al., (2008) "Quantitative differential interference contrast microscopy based on structured-aperture interference," *Applied Physics Letters*, 93:091113-1-091113-3.
Cui, Xiquan, et al., (2006) "Slanted hole array beam profiler (SHArP)—a high-resolution portable beam profiler based on a linear aperture array," *Optics Letters*, 31(21):3161-3163.

(56) References Cited

OTHER PUBLICATIONS

Dahan, M., et al., (2001) "Time-gated biological imaging by use of colloidal quantum dots," *Optics Letters*, 26(11):825-827.

De Fornel, F., (2001) "Evanescent waves from Newtonian optics and Atomic optics," *Springer Series in Optical Sciences*, 270 pages.

Doyle, P. S., et al., (Mar. 2002) "Self-assembled magnetic matrices for DNA separation chips," *Science*, 295(5563):2237.

Drezet, A., et al., (Jul. 25, 2008) "Miniature Plasmonic Wave Plates," *Physical Review Letters*, 101:43902-1-043902-4.

Dunn, et al., (2007) "Introduction to Confocal Microscopy," [retrieved on Aug. 2, 2007 at available at http://www.microscopyu.com/articles/confocal], *MicroscopyU*, 3 pp.

Ebbesen, T. W., et al., (Feb. 1998) "Extraordinary optical transmission through sub-wavelength hole arrays," *Nature*, 391(6668):667-669.

Fowles, G. R., (1989) "Introduction to Modern Optics," *Dover Publications, Second Ed.*, New York, pp. 57-61.

Fu, Anne Y., et al., (Nov. 1999) "A microfabricated fluorescence-activated cell sorter," *Nature Biotechnology*, 17(11):1109-1111.

Garcia De Abajo, F. J., (2002) "Light transmission through a single cylindrical hole in a metallic film," *Optics Letters*, 10(25):1475-1484.

Gay, G., et al., (2006) "The optical response of nanostructured surfaces and the composite diffracted evanescent wave model," *Nat Phys*, 2:262-267.

Gbur, G., et al., (2005) "Achieving superresolution in near-field optical data readout systems using surface plasmons," *Applied Physics Letters*, 87:191109—pp. 1-3.

Heng, Xin, et al., (2005) "Optofluidic Microscopy," *Proceedings of the ICMM 2005 3rd International Conference on Microchannels and Minichannels*, pp. 1-6.

Heng, Xin, (Apr. 1, 2005) "OptoFuidic Microscopy (OFM)" *Biophotonics Group, Caltech, DARPA optofluidic center retreat*, 9pp.

Heng, Xin, et al., (2005) "Optofluidic Microscope—a miniature microscope on a chip," *9th International Conference on Miniaturized Systems for Chemistry and Life Sciences* (μTAS), 3pp.

Heng, Xin, et al., (2006) "Characterization of light collection through a subwavelength aperture from a point source," *Optics Express*, 14:10410-10425.

Heng, Xin, et al., (2006) "Optofluidic Microscopy—a method for implementing a high resolution optical microscope on a chip," *Lab Chip*, 6(10):1274-1276.

Lalanne, P., and Hugonin, J., (2006) "Interaction between optical nano-objects at metallo-dielectric interfaces," *Nature Physics*, 2:551.

Laux, E., et al., (2008) "Plasmonic photon sorters for spectral and polarimetric imaging," *Nature Photonics*, 2:161-164.

Lay, Christophe, et al., "Enhanced microfiltration devices configured with hydrodynamic trapping and a rain drop bypass filtering architecture for microbial cells detection," *Lab on a Chip* 2008, 8:830-833; published as Advanced Article on Apr. 1, 2008 at http://pubs.rsc.org | DOI:10.1039/b800015h, 4 pp.

Lee, Lap Man, et al., (2009) "The Application of On-Chip Optofluidic Microscopy for Imaging *Giardia lamblia* Trophozoites and Cysts," *Biomed Microdevices*, Springer DOI 10.1007/s10544-009-9312-X 11:951-958.

Leen, J., et al., (2008) "Improved focused ion beam fabrication of near-field apertures using a silicon nitride membrane," *Optics Letters*, 33:2827-2829.

Lezec, H.J., et al. (2002) "Beaming Light from a Subwavelength Aperture," *Science*, 297(5):820-822.

Lezec, H.J., and Thio, T., (Aug. 2004) "Diffracted evanescent wave model for enhanced and suppressed optical transmission through subwavelength hole arrays," *Optics Express*, 12(16):3629-3651.

Liu, H., and Lalanne, P., (2008) "Microscopic theory of the extraordinary optical transmission," *Nature*, 452:728-731.

Liu, Shaorong R., (2003) "A microfabricated hybrid device for DNA sequencing," *Electrophoresis* 2003, 24(21):3755-3761.

Minakawa, K., et al., (2009) "Microchamber Device Equipped with Complementary Metal OXide Semiconductor Optical Polarization Analyzer Chip for Micro Total Analysis System," *Jpn. J. Appl. Phys.*, 48:04C192.

Murphy, et al., (2007) "Differential Interference Contrast (DIC)," available from Nikon MicrocopyU at http://www.microscopyu.com/articles/dic/dicindeX.html.

Ng, R., et al., (2005) "Light field photography with a hand-held plenoptic camera," *Computer Science Technical Report CSTR*, vol. 2, 11 pp.

Nott, Prabhu R., et al., (1994) "Pressure-driven flow of suspensions: simulation and theory," *J. Fluid Mech.*, 275:157-199.

Nozokido, Tatsuo, et al., (2001) "Scanning Near-Field Millimeter-Wave Microscopy Using a Metal Slit as a Scanning Probe," *IEEE Transactions on Microwave Theory and Techniques*, 49(3):491-99.

Pacifici, D., et al., (2007) "All-optical modulation by plasmonic excitation of CdSe quantum dots," *Nature photonics*, 1:402-406.

Pacifici, D., et al., (2008) "Quantitative determination of optical transmission through subwavelength slit arrays in Ag films: Role of surface wave interference and local coupling between adjacent slits," *Physical Review B*, 77:115411.

Pacifici, D., et al., (2008) "Universal optical transmission features in periodic and quasiperiodic hole arrays," *Optics Express*, 16:9222-9238.

Pfeiffer, F., et al., (2008) "Hard-X-ray dark-field imaging using a grating interferometer," *Nature Materials* 7:134-137.

Platt, B. C. and Shack, R., (Sep./Oct. 2001) "History and Principles of Shack-Hartmann Wavefront Sensing," *Journal of Refractive Surgery* 17:S573-S577.

Popescu, G., et al., (Nov. 24, 2006) "Optical measurement of cell membrane tension," *Physical Review Letters* 97:218101-1-4.

Probstein, R. F., (2003) "Solutions of Uncharged Macromolecules and Particles," Chapter 5: pp. 109-116, p. 123; "Solutions of Electrolytes," Chapter 6: 190-197; "Surface Tension," Chapter 10: pp. 309-310; *Physicochemical Hydrodynamics*, Wiley, 2nd Edition.

Psaltis, Demetri, et al., (Jul. 2006) "Developing optofluidic technology through the fusion of microfluidics and optics," *Nature*, 442:381-386.

Rappaz, B., et al., (2005) "Measurement of the integral refractive index and dynamic cell morphometry of living cells with digital holographic microscopy," *Optics Express*, 13:9361-9373.

Rust, M. J., et al., (2006) "Sub-diffraction-limit imaging by stochastic optical reconstruction microscopy (STORM)," *Nature Methods*, 3:793-795.

Schouten, H., et al., (2005) "Plasmon-assisted two-slit transmission: Young's experiment revisited," *Physical Review Letters*, 94:53901.

Schwiegerling, Jim, and Neal, Daniel, (2005) "Historical development of the Shack-Hartmann wavefront sensor," in Robert Shannon and Roland Shack: Legends in Applied Optics, edited by J. E. Harvey and R. B. Hooker _SPIE, Bellingham, WA, pp. 132-139.

Segre, G., et al., (1962) "Behavior of macroscopic rigid spheres in Poiseuille flow: Part 1. Determination of local concentration by statistical analysis of particle passages through crossed light beams," *J. Fluid Mech.*, 14:115-135.

Segre, G., et al., (1962) "Behavior of macroscopic rigid spheres in Poiseuille flow: Part 2. Experimental results and interpretation," *J. Fluid Mech.*, 14:136-157.

Seo, Jeonggi, et al., "Disposable integrated microfluidics with SELF-aligned planar microlenses," *Sensors and Acutators B*, vol. 99, pp. 615-622 (2004).

Shi, X., et al., (2003) "Ultrahigh light transmission through a C-shaped nanoaperture," *Optics letters*, 28:1320-1322.

Stanley, S.L., "Amoebiasis," *Lancet* 361, pp. 1025-1034 (2003).

Stone, H.A., et al., (2004) "Engineering Flows in Small Devices: Microfluidics Toward a Lab-on-a-Chip," *Annu. Rev. Fluid Mech.*, 36:381-411.

Tai, Y. C., et al., (2002) "Integrated micro/nano fluidics for mass-spectrometry protein analysis," *International Journal of Nonlinear Sciences and Numerical Simulation*, 3(3-4):739-741.

Tearney, G. J., et al., (1996) "Scanning single-mode fiber optic catheter-endoscope for optical coherence tomography," *Optics Letters*, 21:543-545.

(56) References Cited

OTHER PUBLICATIONS

Tegenfeldt, Jonas O., et al., (2004) "Micro- and nanofluidics for DNA analysis," Analytical and Bioanalytical Chemistry, 378(7): 1678-1692.

Tegenfeldt, Jonas O., et al., (Feb. 2001) "Near-field Scanner for Moving Molecules," *Physical review letters*, 86(7):1378-1381.

Thio, T., et al., (2001) "Enhanced light transmission through a single subwavelength aperture," *Opt. Lett.*, 26:1972-1974.

Thio, T., et al., (2002) "Giant optical transmission of sub-wavelength apertures: physics and applications," *Nanotechnology*, 13:429-432.

Tokeshi, Manabu, et al., (2003) "Chemical processing on microchips for analysis, synthesis, and bioassay," *Electrophoresis*, 24(21):3583-3594.

Trau, D., et al., (2002) "Genotyping on a complementary metal oxide semiconductor silicon polymerase chain reaction chip with integrated DNA microarray," *Analytical Chemistry*, 74(13):3168-3173.

Ung, B., and Sheng, Y., (2008) "Optical surface waves over metallo-dielectric nanostructures: Sommerfeld integrals revisited," Optics Express, 16:9073-9086.

Yu, N., et al., (2009) "Semiconductor lasers with integrated plasmonic polarizers," *Applied Physics Letters*, 94:151101.

Zayats, et al., (2005) "Nano-optics of surface plasmon polaritions," *Phys. Rep.* 408:131-314.

Zheng, et al., (2009) "A Phase Conjugate Mirror Inspired Approach for Building Cloaking Structures with Left-handed Materials," *New Journal of Physics* 11(4):033010-25.

Zheng et al., (2010) "Improving Weak-Signal Identification via Predetection Background Suppression by a Pixel-Level, Surface-Wave Enabled Dark-Field Aperture," *Optics Letters* 35(15):2636-2638.

Zheng, et al., (May 2010) "Surface-wave-enabled darkfield aperture: A method for suppressing background during weak signal detection," *PNAS* USA, 107(60):9043-9048.

Zheng, et al., (Oct. 15, 2011) "Microscopy refocusing and dark-field imaging by using a simple LED array," *Optics Letters* 36(20):3987-3989.

\* cited by examiner

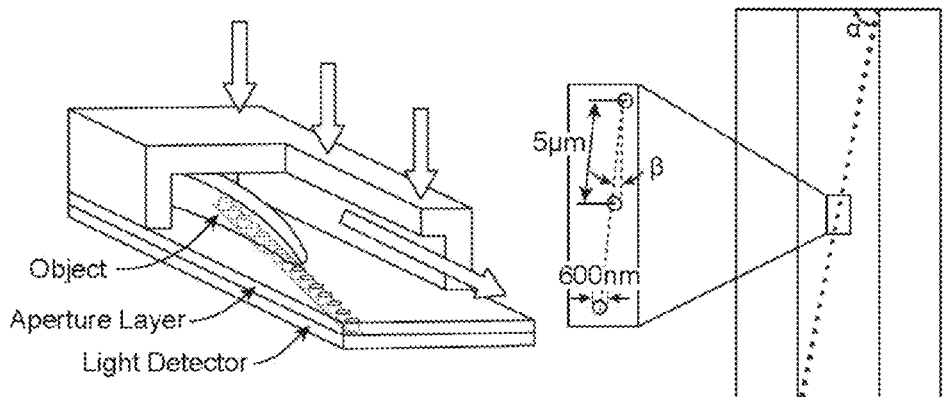
FIG. 1A
FIG. 1B
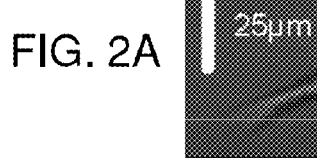
FIG. 2A
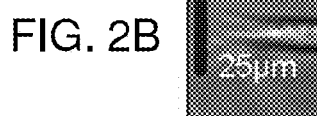
FIG. 2B
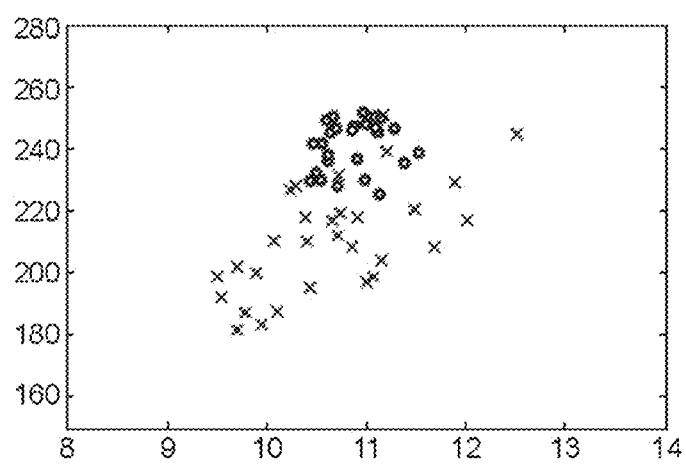
FIG. 2C

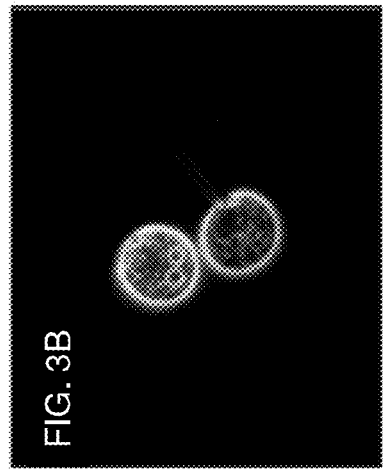
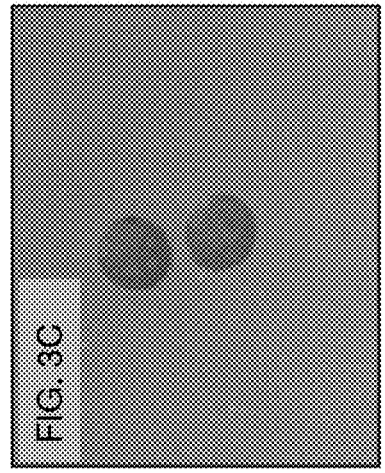
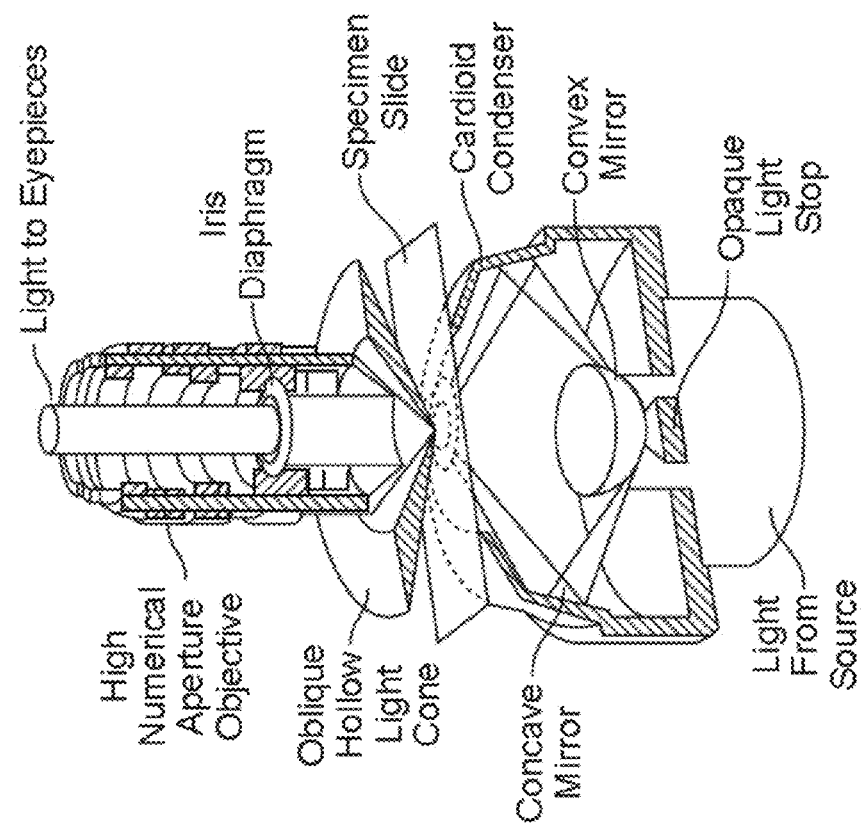
FIG. 3A Cardioid Darkfield Condenser
FIG. 3B
FIG. 3C

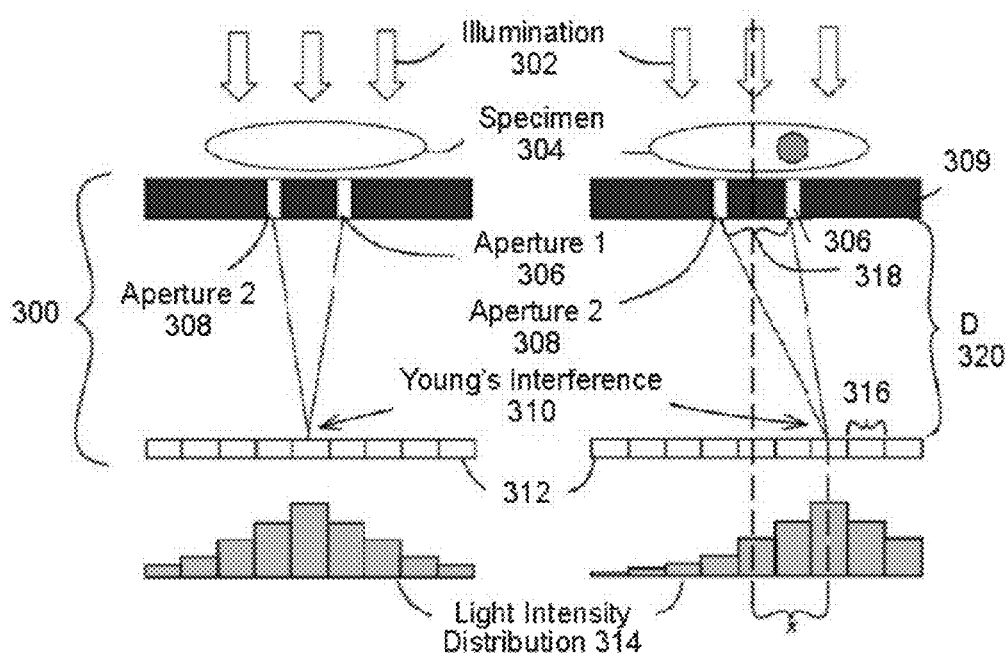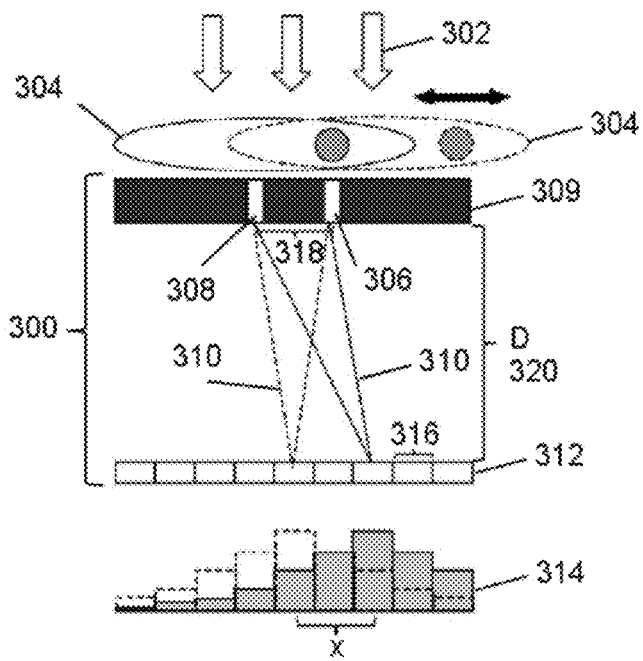

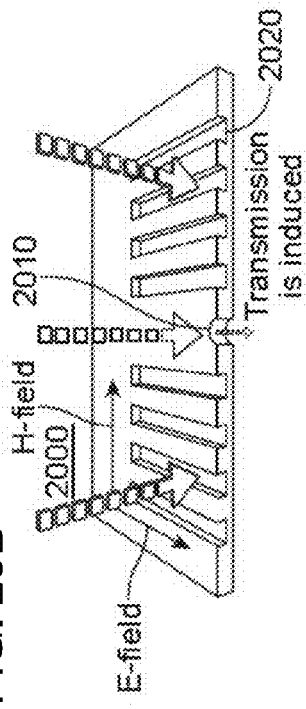
FIG. 23A
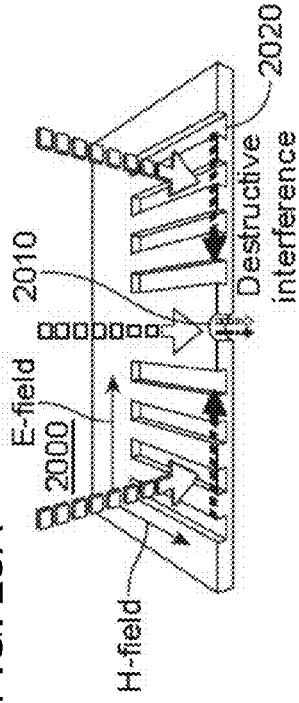
FIG. 23B
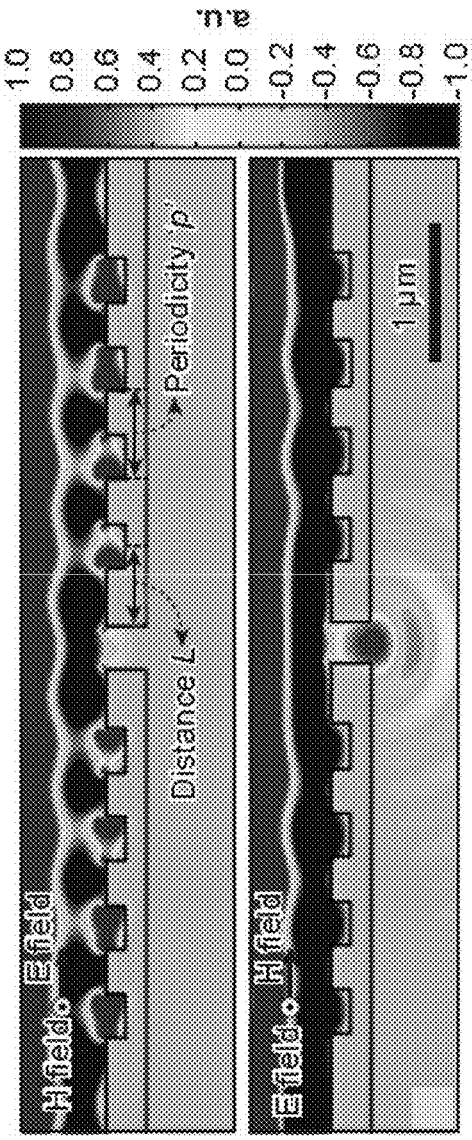
FIG. 23C
FIG. 23D

FIG. 29A
FIG. 29B
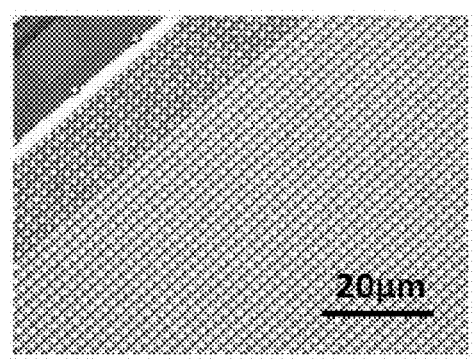
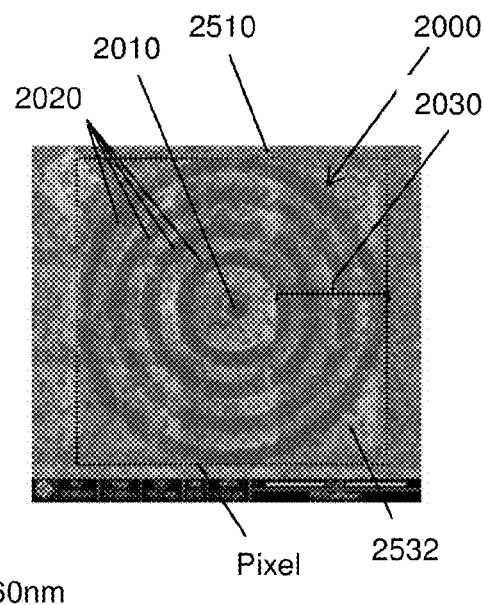
FIG. 29C
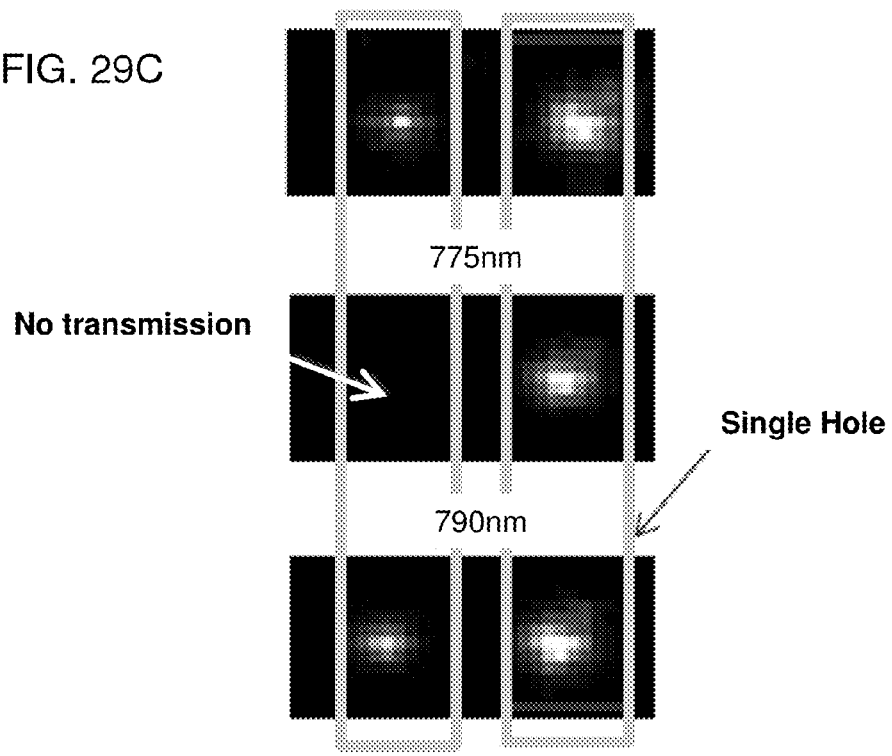

SURFACE WAVE ASSISTED STRUCTURES AND SYSTEMS

CROSS-REFERENCES TO RELATED APPLICATIONS

This is a continuation-in-part application of U.S. patent application Ser. No. 12/792,059, filed on Jun. 2, 2010, now U.S. Pat. No. 8,189,204 which is a continuation-in-part application of U.S. patent application Ser. No. 11/743,581, filed on May 2, 2007, now U.S. Pat. No. 7,768,654 which is a non-provisional of and claims priority to U.S. provisional applications 60/796,997 and 60/796,996 filed on May 2, 2006. U.S. patent application Ser. No. 12/792,059 filed on Jun. 2, 2010 is also a non-provisional of and claims priority to U.S. provisional applications 61/183,868, filed on Jun. 3, 2009 and 61/345,018 filed on May 14, 2010. The present application is also a non-provisional of and claims priority to U.S. provisional application No. 61/430,690 entitled "Pixel-Integrated Optical Structure Designs for CMOS Image Sensor" filed on Jan. 7, 2011. All of these applications are hereby incorporated by reference in their entirety for all purposes.

This non-provisional application is related to the following co-pending and commonly-assigned patent applications, which are hereby incorporated by reference in their entirety for all purposes:

U.S. patent application Ser. No. 11/125,718 entitled "Optofluidic Microscope Device" filed on May 9, 2005, now U.S. Pat. No. 7,773,227.

U.S. patent application Ser. No. 11/686,095 entitled "Optofluidic Microscope Device" filed on Mar. 14, 2007, now U.S. Pat. No. 7,751,048.

U.S. patent application Ser. No. 12/398,050 entitled "Optofluidic Microscope Device with Photosensor Array" filed on Mar. 4, 2009.

U.S. patent application Ser. No. 12/435,165 entitled "Quantitative Differential Interference Contrast (DIC) Microscopy and Photography Based on Wavefront Sensors" filed on May 4, 2009, now U.S. Pat. No. 8,039,776.

U.S. patent application Ser. No. 12/690,952 entitled "Quantitative Differential Interference Contrast (DIC) Microscopy and its Computed Depth Sectioning Ability" filed on Jan. 21, 2010.

The following non-provisional patent application is being filed on the same day and is hereby incorporated by reference in its entirety for all purposes: U.S. patent application Ser. No. 13/344,523, filed on Jan. 5, 2012, entitled "Light-Field Pixel".

STATEMENT REGARDING FEDERALLY SPONSORED RESEARCH AND DEVELOPMENT

This invention was made with government support under EB008867 awarded by the National Institutes of Health and under Grant No. HR0011-04-1-0032 awarded by DARPA. The government has certain rights in the invention.

BACKGROUND OF THE INVENTION

Differential Interference Contrast (DIC) Microscopes

A major problem of imaging transparent specimens with conventional microscopes is that it can be difficult to elicit contrast, because the imaging technique is solely based on the amplitude information of the sampling light. This difficulty can be especially problematic for examining transparent or nearly transparent biological specimens. Phase information, if measured, can improve the imaging contrast dramatically. Conventional DIC microscopy performs admirably in this respect by rendering excellent phase contrast in these biological specimens, and is widely used in biology and clinical laboratories.

DIC microscopes are beam-shearing interference systems. An example of a conventional DIC microscope can be found in Murphy, Schwartz, Salmon, Spring, Parry-Hill, Sutter, and Davidson, "Differential Interference Contrast (DIC), 2007," available from Nikon MicroscopyU at http://www.microscopyu.com/articles/dic/dicindex.html, which is hereby incorporated by reference in its entirety for all purposes. In DIC microscopes, a reference beam is sheared by a very small distance with respect to a sample beam. The phase difference between the reference beam and the sample beam after they pass two adjacent spots of the specimen provides the differential phase contrast of the specimen. Since DIC microscopy is an interference-based technique, it can distinguish minuscule amounts of phase differences and identify small changes in the sample's refractive index.

Prior art DIC microscopes have some disadvantages. Firstly, prior art DIC microscopes are very expensive instruments, as many complicated and expensive optical components are required to manipulate the light. Secondly, the lateral resolution of current DIC microscopes is determined by the spot size of the objective lens of the DIC microscope, which has a diffraction limit. The small sheared distance between the reference beam and the sample beam is usually tuned to be slightly smaller than this spot size.

Microfluidics

Recent developments in microfluidics have brought forth a variety of new devices that can potentially revolutionize traditional biomedical and chemical experiments. Examples of microfluidic devices can be found in Fu, A. Y., et al., "*A microfabricated fluorescence-activated cell sorter, Nature Biotechnology,*" 1999, 17(11), pp. 1109-1111, Tai, Y. C., et al., "*Integrated micro/nano fluidics for mass-spectrometry protein analysis,*" International Journal of Nonlinear Sciences and Numerical Simulation, 2002, 3(3-4), pp. 739-741, Tokeshi, M., et al., "Chemical processing on microchips for analysis, synthesis, and bioassay," Electrophoresis, 2003, 24(21): pp. 3583-3594, Doyle, P. S., et al., "*Self-assembled magnetic matrices for DNA separation chips,*" Science, 2002, 295(5563), pp. 2237-2237, Trau, D., et al., "*Genotyping on a complementary metal oxide semiconductor silicon polymerase chain reaction chip with integrated DNA microarray, Analytical Chemistry,*" 2002, 74(13), pp. 3168-3173, and Liu, S. R., "*A microfabricated hybrid device for DNA sequencing,*" Electrophoresis, 2003, 24(21), pp. 3755-3761, which are hereby incorporated by reference in their entirety for all purposes. Another such device is the optofluidic microscope (OFM) described in U.S. patent application Ser. No. 11/686, 095, filed on Mar. 14, 2007, by Changhuei Yang and Demetri Psaltis, entitled OPTOFLUIDIC MICROSCOPE DEVICE, which is hereby incorporated by reference in its entirety for all purposes. The OFM fuses the advantage of optical imaging in providing high resolution and the advantages of microfluidics, such as low cost and high throughput. Further, OFM's application in nematode imaging and phenotyping has been reported in Heng, X., et al., "*Optofluidic microscope, a miniature microscope on a chip,*" 9th International Conference on Miniaturized Systems for Chemistry and Life Sciences (µTAS), 2005, which is hereby incorporated by reference in its entirety for all purposes.

FIGS. 1A and 1B are schematic drawings an OFM device having a body that forms a fluid channel. An object is passing through the fluid channel generally in the flow direction. The body includes an aperture layer having an aperture array of light transmissive regions (e.g., apertures, slits, etc.). The aperture layer is located adjacent to the light detector layer having an array of light detecting elements. The aperture array is oriented at a small angle β relative to the fluid channel (FIG. 1B). As an object passes over the aperture array, light detecting elements detect light through the light transmissive regions. The sensor of a processor communicating with the sensor generates time-varying data in the form of a line scan which can be compiled into an image of the object.

FIG. 2A illustrates an image of wild-type C. elegans larvae at the first larval stage that was generated by an OFM device. FIG. 2B is an OFM generated image of a dpy-24 mutant that was generated by an OFM device. FIG. 2C illustrates the aspect ratio of wild-type larvae and dpy-24 mutants that was generated by an OFM device.

In many cases, the light transmissive regions in the OFM device may be of a small size due to the compactness of the OFM device. In these cases, light detector may detect a weak signal. The reduced optical transmission through small apertures is described in Bouwkamp, C. J., "*Diffraction theory*," Reports on Progress in Physics XVIII, 1954, p. 35 and de Abajo, F., "*Light transmission through a single cylindrical hole in a metallic film*," Optics Express, 2002, 10(25), pp. 1475-1484, which are hereby incorporated by reference in their entirety for all purposes. The weak transmission signal can be buried in noise. Although strong illumination from strong sources such as powerful lasers can help to increase the total transmission through small light transmissive regions, high-intensity light may also have adverse effects on the biological specimens.

Darkfield Imaging

The ability of an optical sensor to detect light signals, especially weak light signals, can be limited by the presence of a bright background. This limitation is described in R. Narayanaswamy and O. Wolfbeis, "*Optical sensors: industrial, environmental and diagnostic applications*," Springer Berlin, 2004, and G. C. Cox, "*Optical imaging techniques in cell biology*," Boca Raton: CRC/Taylor & Francis, 2007, which are hereby incorporated by reference in their entirety for all purposes. As such, pre-detection background suppression providing a darkfield can be important in the detection of light signals. The benefit of a darkfield image can be appreciated by drawing an analogy to the visibility of stars in the night and their apparent absence during the day—the absence of the bright background can significantly enhance the relative contrast of the light fields.

Darkfield imaging has numerous advantages and applications. For example, darkfield imaging of biological specimens can be advantageous because the outlines of specimens tend to show up prominently in darkfield images as bright lines delineating the objects and because the interior structures of specimens show up well for similar reasons. In some cases, the increased contrast provided by darkfield imaging can eliminate the need for staining specimens, which could be vitally useful for certain time critical medical procedures such as pathological examination of resected tissue samples during surgery.

Prior darkfield imaging devices such as conventional darkfield microscopes use complex and expensive components to generate a darkfield image. For example, FIG. 3A is a schematic drawing of portions of a conventional darkfield microscope having a cardioid darkfield condenser. The condenser is structured so that light emerging from is incident at large angles on the object. The objective on the opposite side of the object is selected so that the numerical aperture is sufficiently small to ensure that the objective will not collect the illumination light field in the absence of the object. The optics process the scattered or diffracted light due to the presence of the object, to render a darkfield image. FIG. 3B is a darkfield image of Chlamydomonas generated using the conventional darkfield microscope. FIG. 3B is a bright field image of Chlamydomonas generated using a bright field microscope.

Conventional darkfield microscopes are also difficult to operate and can require extensive training. Since the illumination light field must be excluded from the collection aperture of the objective, it precludes the use of high numerical aperture objectives. Additionally, using conventional darkfield microscopes requires familiarity with their working principles, and the positioning of condenser, sample, and objective demands precision.

BRIEF SUMMARY OF THE INVENTION

Embodiments of the present invention relate to imaging devices. More specifically, certain embodiments relate to a surface wave assisted structures and systems for inducing surface waves to interfere with pre-detection light.

One embodiment is directed to a surface wave assisted system comprising an aperture layer having a surface and an aperture, and a plurality of grooves around the aperture. The plurality of grooves is configured to generate an optical transfer function at the aperture by inducing a surface wave for interfering with transmission of light of a range of spatial frequency.

One embodiment is directed to a surface wave assisted polarization sensor comprising an aperture layer with a surface and an aperture. The surface wave assisted polarization sensor also comprises a first and second pluralities of linear grooves located on opposite sides of the aperture and configured to induce a surface wave for destructively interfering with transmission through the aperture of light of a polarization angle. The surface wave assisted polarization sensor also comprises a light detector configured to detect the polarization angle by measuring intensity of light transmitted through the aperture.

One embodiment is directed to a surface wave assisted system for spectral imaging. The surface wave assisted system comprises a grating structure configured to induce a surface wave for increasing intensity of light of a wavelength transmitted through the grating structure. The surface wave assisted system also comprises a light detecting element configured to receive light transmitted through the grating structure and detect the increased intensity of the light of the wavelength.

One embodiment is directed to a surface wave assisted darkfield aperture system comprising an aperture layer having a surface and an aperture, and a plurality of grooves around the aperture. The plurality of grooves is configured to generate a darkfield at the aperture by inducing a surface wave for destructively interfering with direct transmission of a uniform incident light field received by the aperture.

One embodiment is directed to a broadband surface wave aperture system comprising an aperture layer having a surface and an aperture, a first plurality of grooves around the aperture, and a second plurality of grooves around the aperture. The first plurality of grooves is configured to induce a first surface wave configured to destructively interfere with light of a first range of wavelengths. The second plurality of grooves around the aperture is configured to induce a second surface wave configured to destructively interfere with light of a second range of wavelengths different from the first range of wavelengths.

These and other embodiments of the invention are described in further detail below.

BRIEF DESCRIPTION OF THE DRAWINGS

FIGS. 1A and 1B are schematic drawings of an optofluidic microscope device comprising an opaque or semi-opaque film with an array of apertures.

FIG. 2A is an illustration of an OFM image of the wild-type C. elegans larvae at the first larval stage.

FIG. 2B is an illustration of an OFM image of a dpy-24 mutant.

FIG. 2B is a graph illustrating the aspect ratio of wild-type larvae and dpy-24 mutants.

FIG. 3A is a schematic drawing of portions of a conventional darkfield microscope having a cardioid darkfield condenser.

FIG. 3B is a darkfield image of Chlamydomonas generated using the conventional darkfield microscope.

FIG. 3C is a bright field image of Chlamydomonas generated using a bright field microscope.

FIGS. 4A and 4B are schematic drawings of a DIC microscope, in accordance with one or more embodiments of the invention.

FIG. 4C is a schematic drawing of a DIC microscope scanning a specimen, in accordance with one or more embodiments of the invention.

FIG. 23A is a schematic drawing of a portion of a SWEDA structure with grooves in a linear pattern, according to an embodiment of the invention.

FIG. 23B is a schematic drawing of a portion of a SWEDA structure with grooves in a linear pattern, according to an embodiment of the invention.

FIG. 23C is a simulation of the TM case of a SWEDA structure with grooves in a linear pattern, according to an embodiment of the invention.

FIG. 23D is a simulation of the TE case of the SWEDA structure, which shows the electric-field distributions for the TE wave, which shows that the structure does transmit TE wave significantly, according to an embodiment of the invention.

FIG. 29A is an image of a CMOS pixel of an on-chip implementation of a surface wave enabled pre-detection background suppression scheme, according to an embodiment of the invention.

FIG. 29B is a focus ion image of more than a pixel of a SWEDA-based sensor employing an on-chip implementation of a surface wave enabled pre-detection background suppression scheme, according to an embodiment of the invention.

FIG. 29C is a set of images of the measured optical transmission through the darkfield aperture of the pixel in FIG. 29B, according to an embodiment of the invention.

DETAILED DESCRIPTION OF THE INVENTION

Figure 5:
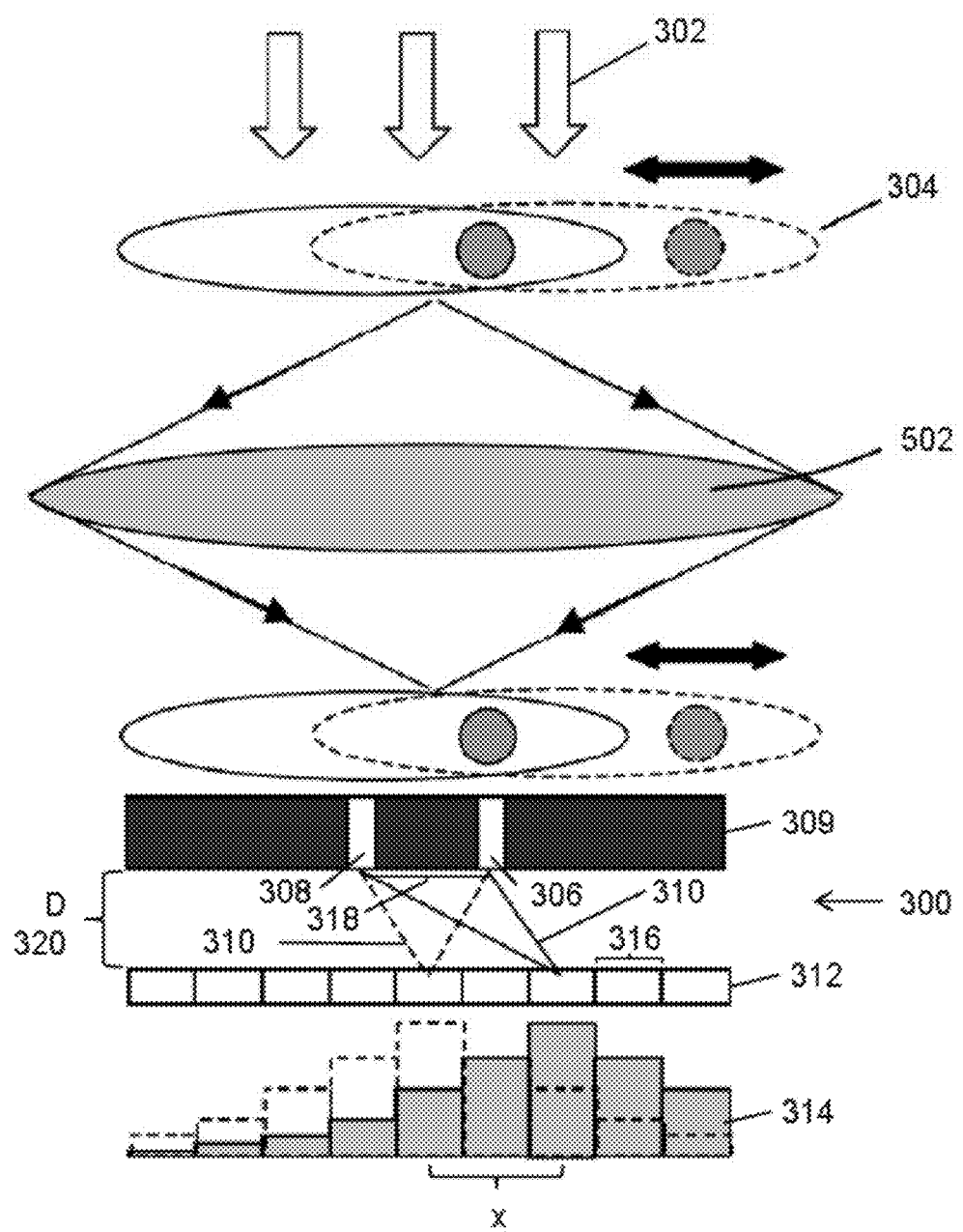
FIG. 5 is a schematic drawing of a DIC microscope, in accordance with one or more embodiments of the invention.

Some embodiments of the invention provide surface wave assisted structures and systems using surface wave assisted structures. These structures and systems have groove or grating structures to induce a surface wave for interfering with incoming light.

I. Differential Interference Contrast (DIC) Microscope/ Light Field Profiler Based on Young's Interference FIGS. 4A and 4B shows the configuration of a DIC microscope based on Young's interference and the operating principle, in accordance with one or more embodiments of the invention.

The DIC microscope 300 consists of two main parts for a Young's interference setup based on two apertures 306 and 308 (i.e., in metal film 309) and a light detector 312 (e.g., CCD [charge-coupled device], CMOS, PSD [photo-sensitive light detector], etc.).

Aperture 1 306 may be used to sample the reference beam from the specimen 304 (object), and aperture 2 308 may be used to sample the sample beam from the specimen 304. If the reference beam and the sample beam pass a homogenous region of the specimen 304, the reference beam and the sample beam carry the same phase. When the reference and sample beams exit from the two apertures 306 and 308, the light intensity distribution 314 of their Young's interference 310 is centered on the light detector 312 (as illustrated in FIG. 4A). However, if the reference beam and the sample beam pass different features in the specimen 304 (i.e., as illustrated by the reference beam passing over the nucleus in FIG. 4B), the beams will carry different phases. Accordingly, when the beams exit from the two apertures 306 and 308, the light intensity distribution of their Young's interference 310 is shifted on the light detector 312. The offset is directly related to the phase difference between the reference beam and the sample beam.

As described herein, Young's interference is used to determine the phase in accordance with $$\Delta \phi \approx \frac{2\pi}{\lambda} \frac{a}{D} x,$$

wherein D is distance 320, a is distance 318, and x is the displacement with respect to the center of the apertures 304, 306.

From the data of light detector 312, the information of the differential phase contrast of the specimen 304 can be easily retrieved. In addition, the amplitude of the sample 304 transmission at that location can be computed by simply summing up all of the signals from the light detector array 312.

To get all of the information of differential phase contrast from the whole specimen 304, one may either scan the DIC microscope 300 across the specimen 304 or scan the specimen 304 across the DIC microscope 300. FIG. 4 illustrates such a scanning of the specimen 304 in accordance with one or more embodiments of the invention.

FIG. 5 illustrates another configuration of a DIC microscope 300 in accordance with one or more embodiments of the invention. As illustrated, an optical system (i.e., lens 502) is used to project the specimen 304 onto the plane of the two interference apertures 306 and 308. The phase difference information of the specimen 304 can be decoded by the Young's interference 310 pattern on the CCD sensor 312. The image of the specimen 304 can either be scanned across the interference apertures 306 and 308 or scan the interference apertures 306 and 308 across the image of the specimen 304 to get all of the information of differential phase contrast from the whole specimen 304.

Figure 6:
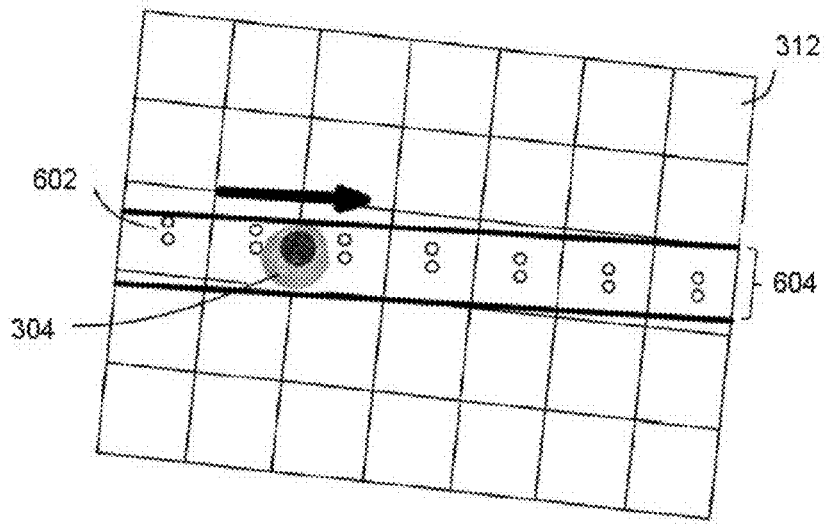
FIG. 6 is a schematic drawing of an on-chip DIC imaging system using an technique, in accordance with one or more embodiments of the invention.

In addition to the above, an OFM technique can be combined with the DIC microscope 300 to implement an on-chip DIC imaging as illustrated in FIG. 6. An example of an OFM can be found in Cui, X., Heng, X., Erickson, D., Psaltis, D., Yang, C. "*Portable optical microscope-on-a-chip*" Photonics West, San Jose, Calif., January 2006, which is hereby incorporated by reference in its entirety for all purposes. In FIG. 6, the DIC-OFM device includes a plurality of apertures 602 in the form of a two parallel single-dimensional arrays of aperture structures. In this case, the aperture structures are aperture pairs. A gap may be located between the aperture layer and the light detector receiving light passing through the apertures. The specimen 304 passes through the fluid channel 604 across the apertures 602. Each DIC microscope 300 can generate a line scan from the signal received from the light detector as the specimen 304 flows across the aperture array through the fluid channel 604. The image can be reconstructed from the line scans.

As illustrated in FIG. 6, the light detector 312 may include a plurality of light detecting elements (e.g., sensor pixels). In this example, the plurality of light detecting elements is in the form of a two dimensional array. In one or more embodiments, a single light detecting element (e.g., sensor pixel) is associated with an aperture pair 602 in the center of each sensor pixel. Further, the fluid channel 604 is oriented at an angle with respect to the pixels. Accordingly, each aperture pair 602 is centered over a light detecting element while the fluid channel 604 is angled over the light detecting elements. Such an arrangement, provides the ability to better determine DIC information about the specimen 304 (e.g., via analysis of the light intensity distribution 314) while the specimen 304 flows across the channel 604.

Figure 7:
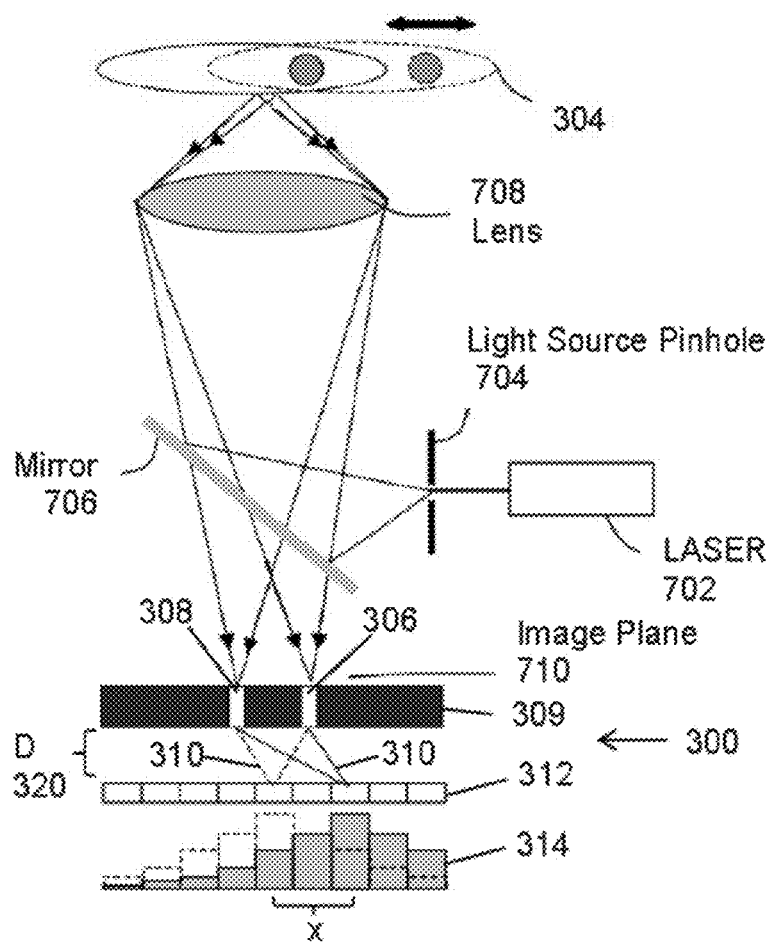
FIG. 7 is a schematic drawing of a confocal microscope technique combined with a DIC microscope to implement a confocal DIC imaging microscope, in accordance with one or more embodiments of the invention.

Embodiments of the invention may also combine the confocal microscope technique with the DIC microscope (described above) to implement a confocal DIC imaging microscope as illustrated in FIG. 7. An example of the confocal microscope technique can be found in Dunn, Wang, Paddock, Hzen, DeVries, Pawley, Parry-Hill, Fellers, and Davidson, "*Introduction to Confocal Microscopy,*" 2007, available from MicroscopyU at http://www.microscopyu.com/articles/confocal/, which is hereby incorporated by reference in its entirety for all purposes. If the DIC microscope (e.g., item 300 of FIG. 3) is applied to the setup similar to a confocal microscope, the interference apertures 306-308 in the DIC microscope 300 can act as a spatial filter as the detector pinhole in confocal microscope.

The difference between the prior microscopes described herein and the confocal DIC imaging microscope of FIG. 7 is that there are two spatial filter pinholes (e.g., apertures 304, 306), which can grab information from two 3D localized spots in the specimen 304 simultaneously. The phase difference information between these two spots also can be decoded by the Young's interference pattern 310 on the light sensor 312. Accordingly, the 3D information of the differential phase contrast may be obtained from the specimen.

As illustrated in FIG. 7, the laser 702 passes through the light source pinhole 704 and is reflected by the mirror 706 and the lens 708 to illuminate the specimen 304. Accordingly, FIG. 7 illustrates a reflective mode microscope since the light that is used to illuminate the specimen plane 304 from the bottom while maintaining the image plane 710 immediately above the apertures 304, 306.

In the above descriptions, the light detector 312 may be described as a CCD sensor. However, a CMOS, a position sensitive device (PSD) or other kinds of photo detectors can be used.

Referring again to FIGS. 4A and 4B, it may be noted that the sensitivity of the differential phase detection in the DIC microscope (described herein) may be determined by the distance 318 between two interference apertures 304, 306, the distance 320 between the interference apertures 304, 306 and the photo detector 312, and the position sensitivity 316 of the photo detector. A spacer or a means/mechanism that provides the desired spacing 320 may be used. Further, the lateral resolution of the DIC microscope 300 may be determined by the distance 318 between the two apertures 304, 306. Proper care in the design should be taken to meet to the requirement of the specific application.

Potential applications of embodiments of the invention include inexpensive high resolution and more capable DIC imaging as well as on-chip DIC imaging devices. In addition, the measurement of phase may be used in various contexts such as an interferometer/DIC microscope or as a Wavefront sensor/Shack Hartmann device.

Using embodiments of the invention, a Gaussian laser beam or an optical vortex may also be profiled. The quantitative measurement of laser beam profiles may be useful for ensuring the efficient and accurate use of lasers in applications ranging from laser machining to fiber optics to laser eye surgery. In addition, precise knowledge of the focal field distribution of high-NA lenses may be important in the design of systems such as confocal laser scanning microscopy and optical serial sectioning microscopy.

Figure 8:
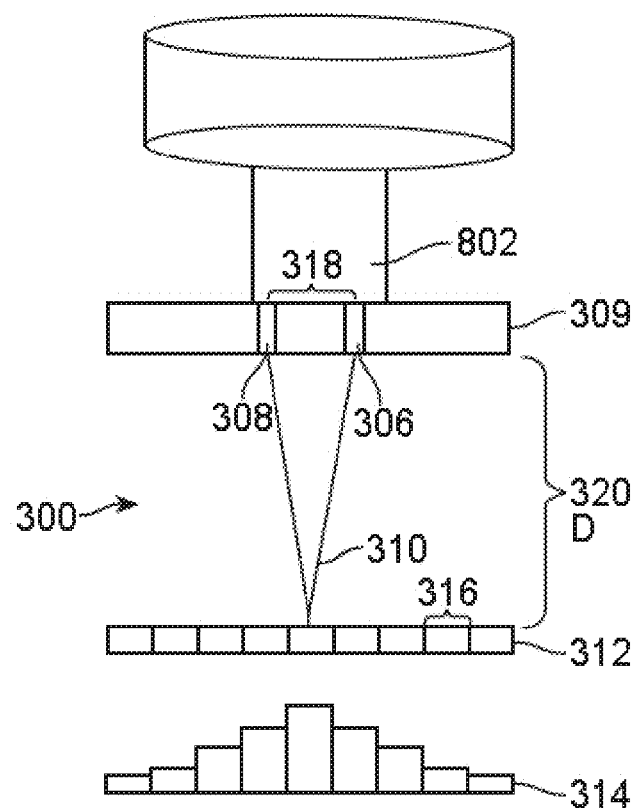
FIG. 8 is a schematic drawing of a single axis on-chip DIC phase beam profiler, in accordance with or more embodiments of the invention.
Figure 9:
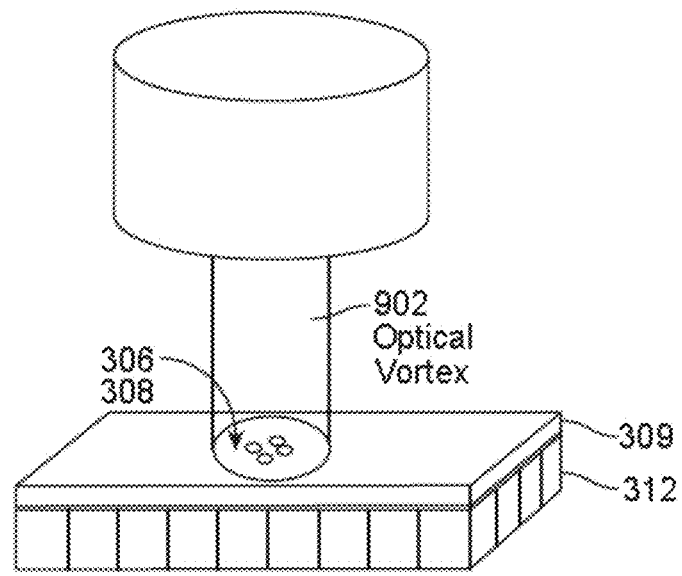
FIG. 9 is a schematic drawing of a dual axes DIC device, in accordance with one or more embodiments of the invention.

FIG. 8 illustrates a single axis on-chip DIC phase beam profiler in accordance with or more embodiments of the invention. Rather than illuminating a specimen as illustrated in FIG. 3-6, a single axis laser beam 802 may be projected onto the apertures 306-308. Four apertures 306-308 may also be used to create a dual axes on-chip DIC phase beam profiler in accordance with one or more embodiments of the invention. FIG. 9 illustrates a dual axis DIC that may be used in accordance with one or more embodiments of the invention. As illustrated the optical vortex 902 from the beam is shown through four apertures onto a light detector 312.

In addition to the above, a high-resolution portable beam profiler may be based on a slanted linear array of apertures, termed a slanted hole array beam profiler (SHArP). Apertures may be holes directly fabricated on sensor such as a metal-coated CMOS imaging sensor. With a single linear scan, the aperture array can establish a virtual grid of sampling points for beam profiling. The size of the apertures can be adjusted to increase/improve resolution. Such a methodology is further described in Xiquan Cui, Xin Heng, Jigang Wu, Zahid Yaqoob, Axel Scherer, Demetri Psaltis, and Changhuei Yang, "*Slanted hole array beam profiler (SHArP)—a high-resolution portable beam profiler based on a linear aperture array*," Optics Letters, Vol. 21, No. 21, Nov. 1, 2006, pp. 3161-3163, which is hereby incorporated by reference in its entirety for all purposes.

In addition, to the above, it may be noted that a DIC microscope may be qualitative and non-linear in nature. In this regard, a DIC image may be a mix of amplitude and phase information. Accordingly, it may be useful to obtain the actual phase, instead of a directional phase gradient. Embodiments of the invention provide a non-iterative and robust phase reconstruction method. Such a method may apply a Fourier-space integration approach that is direct, straightforward and reasonably accurate for images that do not contain discontinuities (e.g., biological phase images). An example of a Fourier-space integration approach can be found in M. R. Arnison, K. G. Larkin, C. J. R. Sheppard, N. I. Smith, and C. J. Cogswell, "*Linear phase imaging using differential interference contrast microscopy*," Journal of Microscopy, Vol. 214, Part I, April 2004, pp. 7-12, which is hereby incorporated by reference in its entirety for all purposes.

Figure 10:
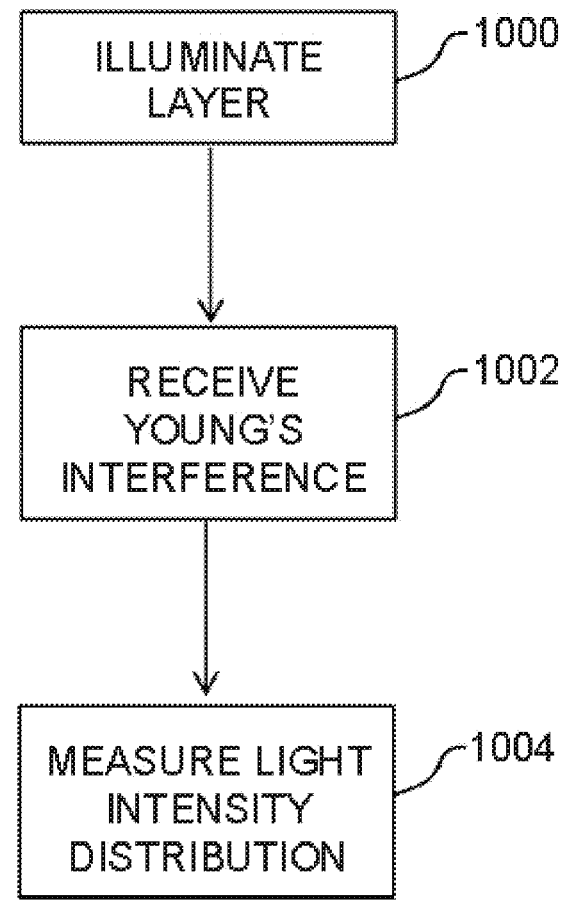
FIG. 10 is a flow chart illustrating a method for determining phase, in accordance with one or more embodiments of the invention.

FIG. 10 is a flow chart illustrating a method for determining phase in accordance with one or more embodiments of the invention. At step 1000, an aperture layer is illuminated. The aperture layer comprises a plurality of apertures. In a microscope embodiment, a specimen may be placed between the illumination source and the aperture layer. Further, the specimen may move across the apertures in the aperture layer (or the microscope can be moved across the specimen). Alternatively, a lens may be used to project the specimen onto a plane of the apertures. In an alternate embodiment (i.e., a beam profiling device), the aperture layer may be illuminated by a laser beam.

At step 1002, the light detector receives the light showing Young's interference, through the apertures.

At step 1004, the light intensity distribution is measured by the light detector. As described above, a specimen may be placed between the illuminating source and the layer and a differential phase contrast of the specimen is determined by the light intensity distribution (i.e., received/measured by the light detector). In a phase beam profiling embodiment, a beam profile of the laser beam is determined based on the light intensity distribution measured by the light detector. It should be noted that a similar embodiments and method may be utilized to produce a light field profiler in accordance with one or more embodiments of the invention.

Alternatively, in an optofluidic DIC microscope embodiment, the specimen may be passed through a fluid channel of a body. In some cases, a surface layer of the fluid channel may be the aperture layer having a plurality of apertures. The apertures may be in the form of an array of groups of light transmissive regions of at least two apertures. The light detector may comprises a two-dimensional (2D) array of light detecting elements with a single corresponding element of the 2D array configured to receive Young's interference from each of the groups of apertures. To create Young's interference, a gap exists between the aperture layer and the light detector. The specimen flows in the fluid channel across the multiple aperture structures and each corresponding light detecting element of the 2D array receives a line scan of the specimen.

In addition to the above, in either phase-beam profiling embodiment or a DIC microscope embodiment, the device may be fabricated/implemented in an on-chip device.

II. Surface Wave Assisted Optofluidic Microscope/Light Field Profiler

Signal transmission can be enhanced and suppressed in devices using an aperture layer with corrugations of grooves around the apertures. Embodiments of the invention use corrugation in the aperture layer in different patterns.

A. Dark Field OFM and Improvement of the Detection Sensitivity

Optical transmission through an aperture or other light transmissive region on a periodically corrugated surface has been examined in the prior art. Both transmission enhancement and suppression have been observed in Lezec, H. J., et al., "*Beaming light from a subwavelength aperture*," Science, 2002, 297(5582), p. 820-822, Ebbesen, T. W., et al., "Extraordinary optical transmission through sub-wavelength hole arrays, Nature," 1998. 391(6668): p. 667-669 and D. Pacifici, et al., "*Quantitative determination of optical transmission through subwavelength slit arrays in Ag films: Role of surface wave interference and local coupling between adjacent slits*," Physical Review B, vol. 77, p. 115411, 2008, which are hereby incorporated by reference in their entirety for all purposes. Henri Lezec and his colleagues used a new model called composite diffracted evanescent waves (CDEWs) to explain the unexpected transmission suppression in Lezec, H. J. and T. Thio, "*Diffracted evanescent wave model for enhanced and suppressed optical transmission through sub-wavelength hole arrays*," Optics Express, 2004, 12(16), p. 3629-3651, which is hereby incorporated by reference in its entirety for all purposes.

Such phenomenon may also be explained by surface waves. The suppression of the optical transmission through an aperture occurs when there is destructive interference between the optical wave coming through the aperture and the optical wave that is channeled in from the peripheral surface waves. A surface wave comprises a surface Plasmon component, a surface scattered component, or other suitable surface wave components, or any suitable combination thereof. In many embodiments, a surface wave consists of a surface Plasmon component and a surface scattered component. A surface Plasmon wave refers to the electromagnetic surface wave existing at the interface between a dielectric and a noble metal. An example of a surface Plasmon wave can be found in S. Maier, "*Plasmonics: fundamentals and applications*," Springer Verlag, 2007, which is hereby incorporated by reference in its entirety for all purposes. An example of evidence of a surface scatterred wave can be found in H. Lezec and T. Thio, "*Diffracted evanescent wave model for enhanced and suppressed optical transmission through subwavelength hole arrays*," Optics express, vol. 12, pp. 3629-3651, 2004, L. Chen, et al., "*Role of radiation and surface plasmon polaritons in the optical interactions between a nano-slit and a nano-groove on a metal surface*," Optics Express, vol. 14, pp. 12629-12636, 2006, G. Gay, et al., "*The optical response of nanostructured surfaces and the composite diffracted evanescent wave model*," Nat Phys, vol. 2, pp. 262-267, 2006, P. Lalanne and J. Hugonin, "*Interaction between optical nano-objects at metallo-dielectric interfaces*," Nature Physics, vol. 2, p. 551, 2006, L. Aigouy, et al., "*Near-field analysis of surface waves launched at nanoslit apertures*," Physical Review Letters, vol. 98, p. 153902, 2007, H. Liu and P. Lalanne, "*Microscopic theory of the extraordinary optical transmission*," Nature, vol. 452, pp. 728-731, 2008, and B. Ung and Y. Sheng, "*Optical surface waves over metallo-dielectric nanostructures: Sommerfeld integrals revisited*," Optics Express, vol. 16, pp. 9073-9086, 2008, which are hereby incorporated by reference in their entirety for all purposes.

Figure 11:
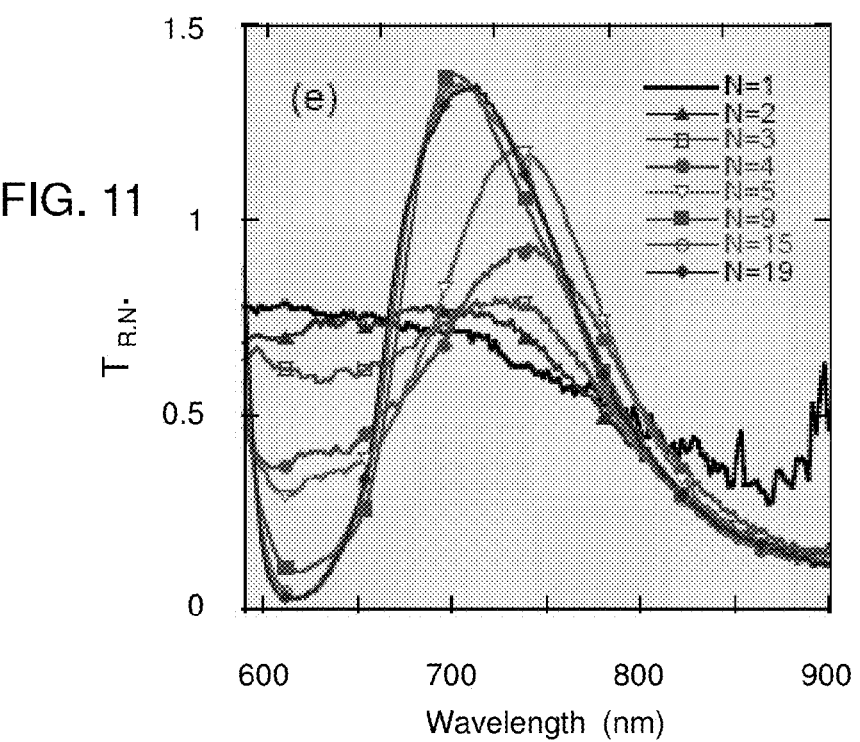
FIG. 11 is a graph of an abnormal transmission of a square aperture array for visible and near-IR light, in accordance with one or more embodiments of the invention.

FIG. 11 illustrates an abnormal transmission of a square aperture array (physically similar to one aperture on a corrugated surface) for visible and near-IR light. The value of N corresponds to the number of apertures in a row and a column. The phenomenon of the transmission suppression can be used in one or more embodiments of the invention based on an OFM setup and can help improve the optical detection.

Figure 12:
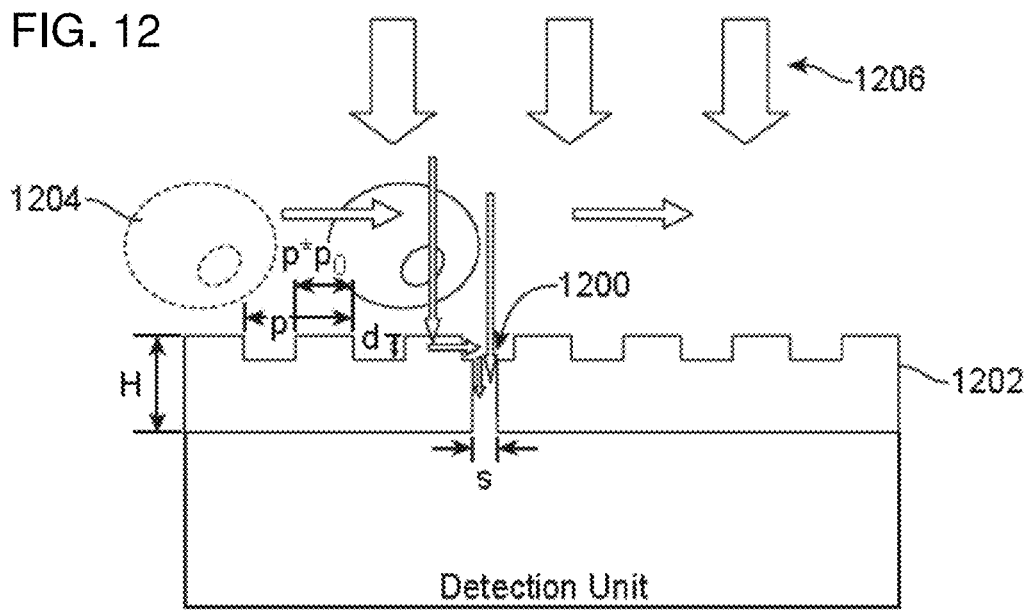
FIG. 12 is a schematic drawing of a corrugated surface an aperture on a layer configured, in accordance with one or more embodiments of the invention.

FIG. 12 illustrates an aperture 1200 with diameter d etched through a corrugated surface 1202 (periodicity or period "p," duty cycle "$p_0$," depth "d", thickness "H"). As illustrated, the aperture 1200 of size s (e.g., diameter) is used as an imaging probe while the specimen 1204 passes through the fluid channel having the corrugated surface 1202. The corrugated surface 1202 can be made in an opaque silver or aluminum film by using electron beam lithography or focused ion beam (FIB). A continuous wave (cw) laser at single wavelength at normal incidence provides the illumination 1206.

The transmission of the aperture 1200 on the corrugated surface 1202 in the visible band and IR band was studied by Lezec et al in Lezec, H. J., et al., "*Beaming light from a subwavelength aperture*," Science, 2002. 297(5582), p. 820-822. At a specific wavelength ($\lambda_0$), optical transmission is at minima and is apparently weaker than that of an isolated aperture (as can be seen in FIG. 11). In the context of OFM, when there is no sample 1204 present, the detector receives a minimum amount of photons and only gives a weak dark field signal.

When a sample 1204 passes over the aperture 1200 array by use of microfluidic driven flow, it will introduce changes in the amplitude and phase of both the optical wave directly through the aperture 1200 and the surface wave on its peripheral. The condition of destructive interference no longer holds, and the transmission increases from the minimum value which indicates the presence of a sample 1204. This detection schema is similar to dark field optical microscopy where the illumination background is originally dark and the introduction of optical discontinuity of the sample 1204 makes it look bright on a dark background. This technique has a signal to noise sensitivity advantage over bright field geometry.

In accordance with one or more embodiments of the invention, a spherical cell 1204 may be used to explain the operations of dark-field OFM. In FIG. 12, a laser source provides a uniform illumination 1206 on the plane of the aperture 1200 region. The parameters of the corrugated surface 1202 are selected such that the transmission of the aperture 1200 is suppressed. As was described above, such suppression is caused by the destructive interference between optical wave transmitted directly through the aperture 1200 and the peripheral surface waves. Therefore, the signal detected by the detection unit underneath the layer/corrugated surface 1202 will be weak. The detection unit can be a CMOS sensor directly attached to the layer 1202 or a microscope relay system that maps the transmission of the aperture 1200 onto a linear sensor array.

Now, consider the situation where a cell 1204 passes over the aperture 1200 by an appropriate microflow driving schema, such as electrokinetics, pressure gradient or dielectrophoresis. When the cell 1204 is far away from the aperture 1200, the cell 1204 has negligible impact on changing the destructive interference condition between the optical wave and the surface wave. Thus, the detector's signal remains weak. However, when the cell 1204 arrives at the aperture 1200, the cell 1204 will change the intrinsic phase of one or both of the two electromagnetic waves. This change is due to the slight optical property discontinuity (e.g. refractive index, absorption coefficient) between the cell 1204 and the medium within which it is suspended. Note that the discontinuity in optical property between cell 1204 and the medium may be subtle and may have little effect in bright field microscope. However, in dark-field OFM, the accumulated phase shift disrupts the original condition of destructive inference, and thus the optical transmission signal will become much stronger, which will be readily registered by the detector as a signal change.

Various schemas may be used to implement one or more embodiments of the invention using dark field microscopy. The goal of such schemas is to create a corrugated surface/grating factor $G_m$ having a defined period (e.g., via an etching and/or fabrication process) such that the surface wave polariton $\vec{K}_{spp}$ is equal to the optical wave on the surface (parallel) $K_{parallel}$:

$$\vec{K}_{spp} = \vec{K}_{parallel} + \vec{G}_m$$

In accordance with the above equations, various schemas may be utilized to optimize the transmission and resolution received via an aperture. Schemas 1-4 below utilize a periodic corrugation on the top surface of the aperture layer (e.g., a metallic film) in an optofluidic microscope. Schema 5 illustrates the use of a periodic corrugation on both the top and bottom surfaces.

It should also be noted that principles described herein may be utilized in a light field profiler.

Schema 1

Figure 13:
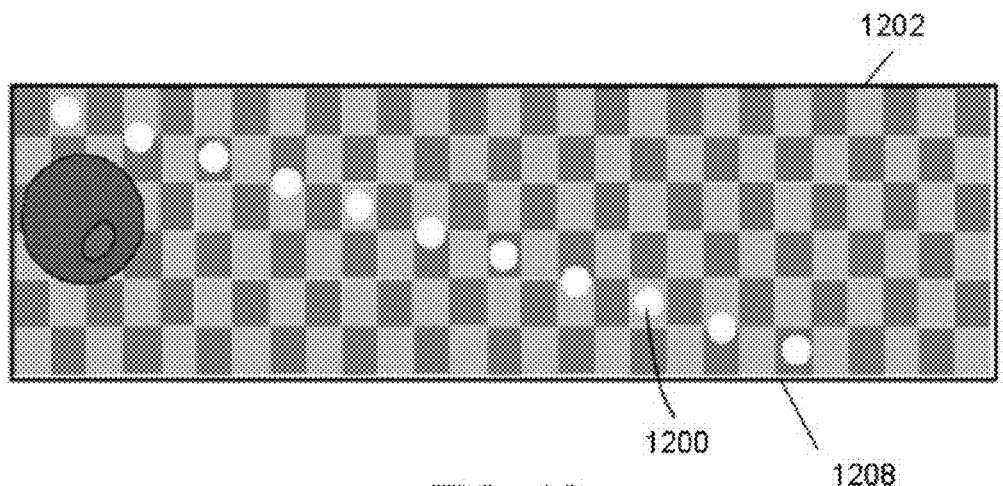
FIG. 13 is a schematic drawing illustrating a schema wherein grey colors schematize surface corrugation that will appear different under a microscope, in accordance with one or more embodiments of the invention.

FIG. 13 illustrates a schema wherein grey colors schematize surface corrugation that will appear different under a microscope. As illustrated, the apertures 1200 are laid down in a slanted fashion on a background of a corrugation surface 1202 (duty cycle of dimples chosen as 50%) with a rectangular lattice 1208. One advantage associated with such a rectangular lattice is that it's fabrication on a relatively large area is simple. As the aperture 1200 sizes are the same, the same "superlattice" structure will work for all of apertures 1200 because the apertures 1200 share the same momentum conservation considerations. Such a mesh checkerboard pattern type of corrugation has been shown to enhance the transmission via the apertures 1200.

Schema 2

Figure 14:
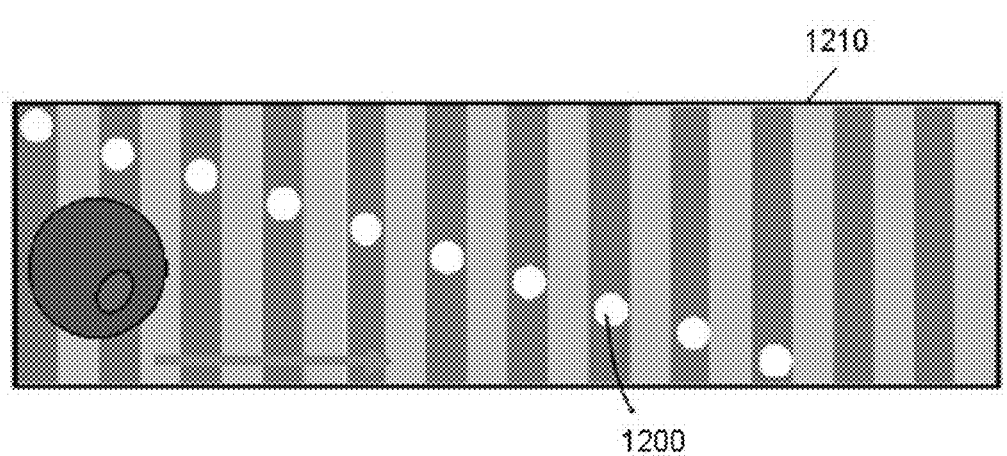
FIG. 14 is a schematic drawing illustrating a schema wherein a two dimensional rectangular lattice-structure (i.e., of FIG. 13) is replaced with a 1D grating structure, in accordance with one or more embodiments of the invention.

FIG. 14 illustrates a schema wherein the two dimensional rectangular lattice-structure 1208 (i.e., of FIG. 13) is replaced with a 1D grating structure 1210. No matter whether surface plasmon waves or surface composite diffracted evanescent waves (CDEWs) are applied to explain optical transmission suppression of the aperture, destructive interference conditions can be satisfied by using 1D grating 1210 and 1D surface waves, as long as the incidence wave does not contain a wave vector component perpendicular to the micro-flow direction. Again, the use of such a 1D grating structure 1210 having a defined period serves to enhance the transmission received through apertures 1200 while providing increased resolution.

Schema 3

Figure 15:
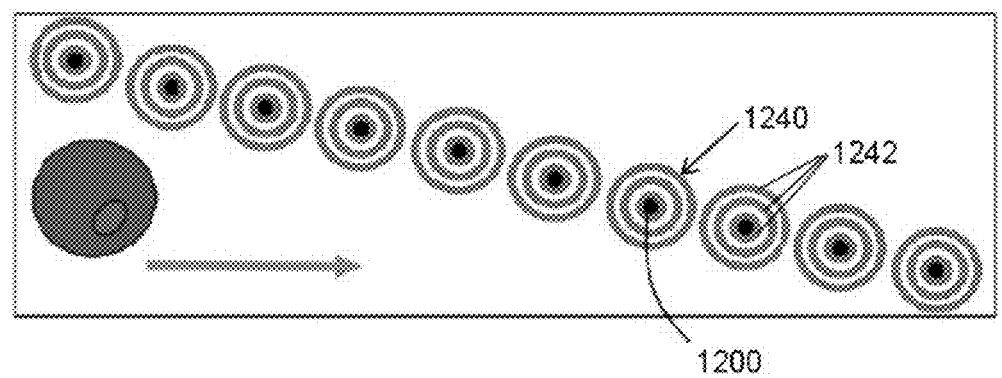
FIG. 15 is a schematic drawing illustrating the use of a corrugated ring structure, in accordance with one or more embodiments of the invention.

It has been shown that the anomalous transmission phenomenon can also be observed in a ring structure with a through-hole at the center of the concentric rings in Lezec, H. J., et al., "*Beaming light from a subwavelength aperture,*" Science, 2002, 297(5582), pp. 820-822. Such a configuration may also be used in dark-field OFM and the physics behind the destructive interference is similar to the two previous cases. This publication is hereby incorporated by reference in its entirety for all purposes. FIG. 15 illustrates the use of such a ring structure 1240 in accordance with one or more embodiments of the invention. Thus, as illustrated in FIG. 15, concentric circle corrugations 1242 are used to enhance the transmission through apertures 1200.

Schema 4

Knowledge of the length of nano-particles can be an invaluable resource. For example, numerous applications of microfluidics based nano-rulers have been useful in biological research, such as measuring the length of the extended DNA molecules and the distance between two fluorescent cells within a microorganism. An example of measuring the length of the extended DNA molecules can be found in Tegenfeldt, J. O., et al., "*Near-field scanner for moving molecules,*" Physical review letters, 2001, 86(7), pp. 1378-1381 and Tegenfeldt, J. O., et al., "*Micro-and nanofluidics for DNA analysis, Analytical and Bioanalytical Chemistry,*" 2004, 378 (7), pp. 1678-1692, which are hereby incorporated by reference in their entirety for all purposes.

Figure 16:
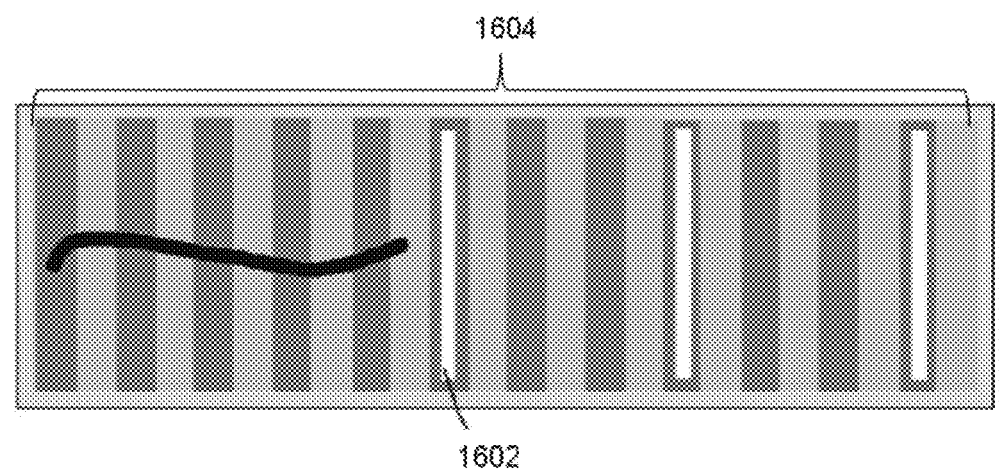
FIG. 16 is a schematic drawing of the use of a microfluidic based nano-ruler, in accordance with one or more embodiments of the invention.

Dark-field OFM can be readily modified for this type of application. It can be applied as a high-resolution ruler or particle sorter in microfluidic settings. FIG. 16 illustrates the use of a microfluidic based nano-ruler in accordance with one or more embodiments of the invention. As illustrated, the size of the slit 1602 can affect the resolution similar to the size of an aperture 1200. In this regard, the smaller the slit or aperture, the higher the resolution. However, as the size of the slit 1200 decreases, the transmission quality decreases. Accordingly, what is needed is the capability to maintain a high resolution (i.e., via a small slit 1602) while enhancing the transmission. A corrugation pattern 1604 such as that illustrated in FIG. 16 serves to enhance the transmission in a desirable manner. In FIG. 16, a corrugation pattern 1604 similar to that used in schema 2 (i.e., FIG. 14) is used.

Schema 5

Figure 17:
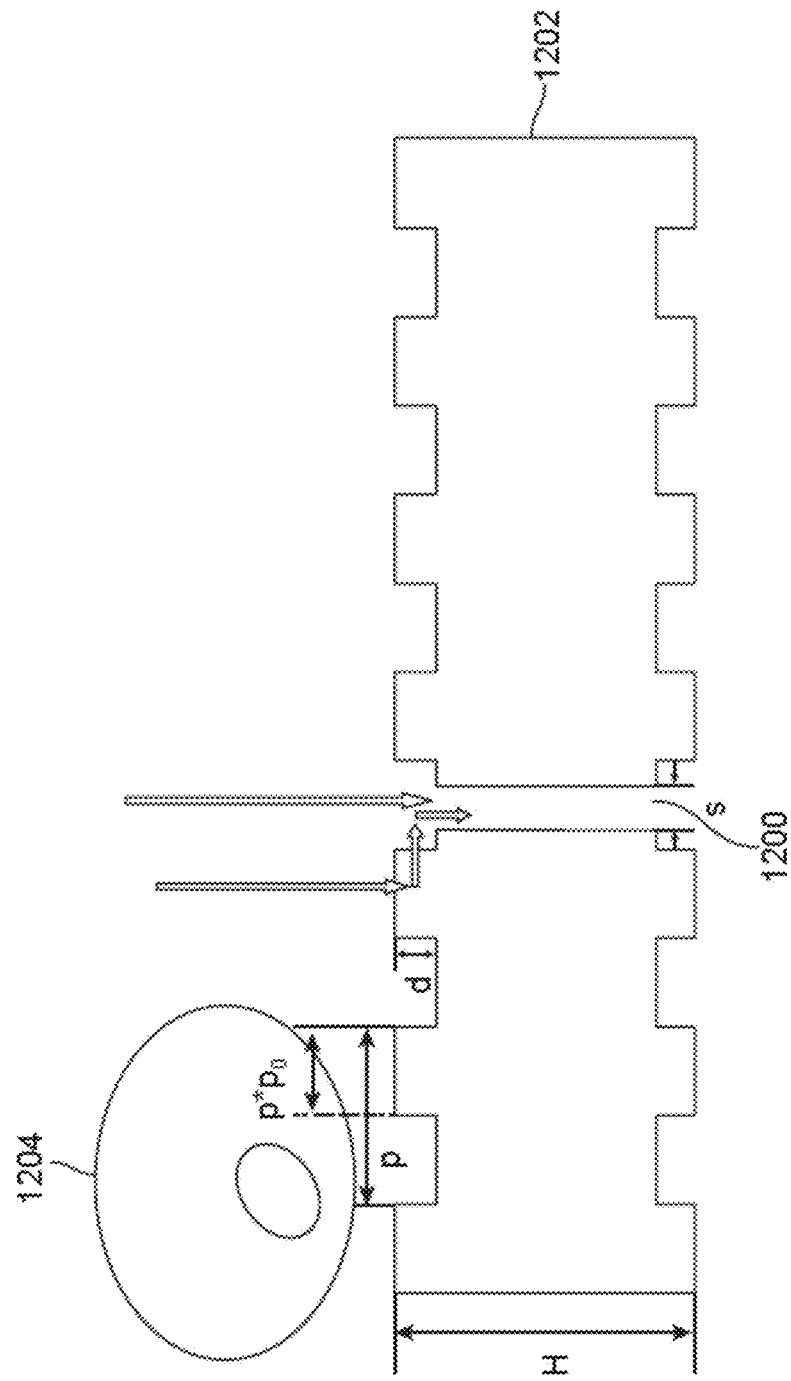
FIG. 17 is a schematic drawing of a periodical configuration fabricated on the top and bottom of a surface containing apertures, in accordance with one or more embodiments of the invention.

In order to facilitate the coupling between surface waves at the top surface and the bottom surface, periodical corrugation can be made on both the bottom and top surfaces as shown in FIG. 17. The parameters used in the design, e.g. d (depth of corrugation), p (period), s (size of aperture), H (height of the aperture layer) and $p_0$ (duty cycle) denote the same features as those in FIG. 12. Making surface corrugation on the bottom surface results in a more directed transmitted light beam can be shown in Lezec, H. J., et al., "*Beaming light from a subwavelength aperture,*" Science, 2002, 297(5582), pp. 820-822. This beam can be much more efficiently collected by an objective lens or a CMOS sensor. The type of device may be made as a free-standing structure, and the fabrication procedure has been demonstrated in Lezec, H. J., et al., "*Beaming light from a subwavelength aperture,*" Science, 2002. 297 (5582), pp. 820-822.

III. Bright Field OFM and Enhancement of Optical Transmission Through a Subwavelength Aperture The surface waves are considered as collective electron excitations, which are characterized by intensive electromagnetic fields confined on the surface of highly conductive metal (e.g. Al, Ag, Au). The interaction of surface waves with probe light is able to enhance the transmission through subwavelength apertures.

In the visible spectral range, the surface waves have a larger momentum (wave number) than propagating light, so the surface waves do not couple to each other efficiently without fine local structures, usually nanostructures. Careful selection of the parameters in FIGS. 12 and 17 can result in strong coupling between light and surface waves, which enhances the transmission through apertures. The well accepted momentum matching formula is:

$$K_{sp} = K_0 + mG_x + lG_y \quad (1)$$

$K_{sp}$ is the wave vector of a surface wave $$K_{sp}(\omega) = \frac{\omega}{c} \sqrt{\frac{\varepsilon_m(\omega)\varepsilon_s}{\varepsilon_m(\omega)+\varepsilon_s}}, \quad (2)$$

$\varepsilon_s$: dielectric medium, $\varepsilon_m$: metal $K_0$ is the wave vector of light in the top dielectric medium.

$$G_x = \frac{2\pi}{L_x}$$

is the 1st order vector in the x direction of the reciprocal lattice of the periodical corrugation.

$$G_y = \frac{2\pi}{L_y}$$

is the 1st order vector in the y direction of the reciprocal lattice of the periodical corrugation.

Note that the above formulas are only approximations for satisfying the surface wave-light resonance condition; the dispersion relation of $K_{sp}$ is modified when the periodical surface corrugation is introduced. However this momentum matching formula works successfully when the corrugation is sufficiently shallow so that the impact on smooth-surface $K_{sp}$ is weak.

Under normal conditions, this light transmission is extremely weak and requires the use of photomultiplier tube (PMT) or avalanche photodiode (APD) detectors for detection. In other words, it precludes the use of a cheap optical detector such as a CMOS sensor as a detector option. Bright field OFM assisted by surface waves aims at making use of the enhancement in optical transmission through apertures (e.g. 100 nm in diameter) to significantly boost a weak transmission, and thereby enable the use of CMOS sensors.

The configurations of bright-field OFM are similar to those of dark-field OFM (see FIGS. 12-17), with only changes in the selection of design parameters (e.g. p, L, d, s, etc.). The resonance condition of surface wave-light coupling is very sensitive to the surrounding medium. Accordingly, the existence of a biological sample breaks down the resonance condition and will immediately change the transmission though the aperture.

Bright field OFM assisted by surface waves is considered very important for high resolution fluorescence imaging. Fluorescence signals carry rich and important biological information. Unfortunately, fluorescence is usually weak and efficient detection is accomplished by using a bulky detector, such as an APD or a PMT with a long integration time. With the surface wave light coupling condition tuned for a specific fluorescence band, the fluorescence signal will be able to efficiently couple into the aperture and be transmitted with an enhanced power.

In accordance with one or more embodiments of the invention, the interaction between surface waves and probing light is facilitated by the introduction of surface corrugations. The interference can be fined tuned for destructive interference condition in dark-field OFM as well as for constructive interference condition in bright field OFM.

Consider the case where an isolated aperture is drilled on a smooth metal surface. The propagation wave scattered by the sample when reaching a subwavelength aperture may not be transmitted efficiently. Only the near field component of the scattered light can efficiently couple with the surface wave. Careful design of structures surrounding the aperture not only enhances the interaction between the surface wave and the scattered light, but also facilitates the coupling of the surface wave to the underneath detector. In other words, the localized (near field) information of the sample can be more effectively coupled by the detector underneath the aperture.

The resolution of the aperture based optical imaging may be compromised to some extent due to the surface wave light coupling. This coupling is quite different from the case where an isolated aperture is used in OFM. Light beaming effect (its physics is approximately explained by equation 1 above) provides a better selection of the direction of probing light in both the far field and near field.

In addition, it may be noted that the interference between the surface wave and the directly transmitted wave can also be arranged to be at other relative phases. In the situation where the two waves are arranged to be 180 degrees out of phase, any change in the relative phase of the two waves will be maximally translated into transmission signal change.

Figure 18:
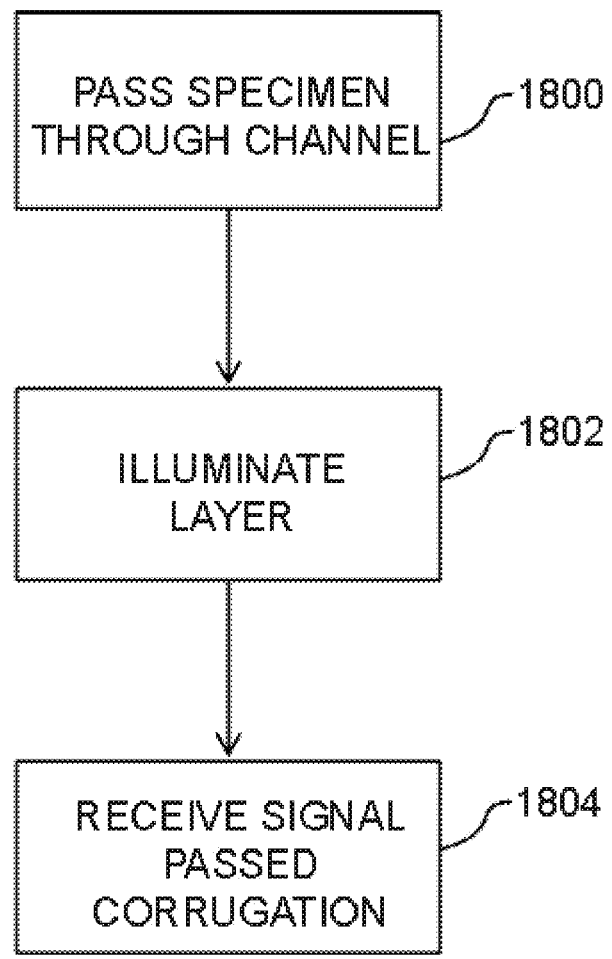
FIG. 18 is a flow chart illustrating a method of enhancing a transmission signal in a surface wave assisted optofluidic microscope, in accordance with one or more embodiments of the invention.

FIG. 18 is a flow chart illustrating the logical flow for enhancing a transmission signal in a surface wave assisted optofluidic microscope in accordance with one or more embodiments of the invention. At step 1800, a specimen is passed through a body comprising a fluid channel having a layer as a surface.

At step 1802, the layer is illuminated. As described above, the layer has at least one aperture that is configured to receive the illumination from an illumination source. Further, a surface wave propagates along the surface. The surface layer can be a metallic film in some cases.

At step 1804, a signal that is based on the illumination passing through the aperture is received on a light detector. In addition, a corrugation is fabricated onto the surface and parameters of the corrugation optimize the signal received on the light detector. Thus, the signal that is received passes across the corrugation thereby enhancing the transmission while maintaining a high resolution. Since the signal is based on the corrugation parameters, such parameters may be tuned to enhance destructive interference in a dark field microscope or may be tuned to enhance constructive interference in a bright field microscope.

The corrugation/corrugation parameters (e.g., grating) may be fabricated in accordance with various different schemas. In one schema, multiple apertures are established in a slanted pattern on the corrugation having a rectangular lattice pattern. In a second schema, multiple apertures are established in slanted pattern on the corrugation having a 1D grating structure pattern. In a third schema, a slanted pattern of multiple apertures are established each in a center of the corrugation defined by concentric rings. In fourth schema, the length of a nanoparticle may be measured based on the signal received on the light detector (i.e., the corrugation and apertures/slits provide a nanoruler structure). In a fifth schema, the corrugation is fabricated onto both a top and bottom of the surface containing the apertures.

The different schemas described herein may be used in combination with the DIC microscopes and phase-beam profilers described above. In this regard, the layer used in the DIC microscopes may also have corrugated surfaces that provide a surface wave-assisted optofluidic microscope.

IV. SWEDA (Surface-Wave-Enabled Darkfield Aperture)

A. Darkfield Imaging

As discussed above, the ability of an optical sensor to detect light signals, especially weak light signals, can be limited by the presence of background light. As such, pre-detection background light suppression providing a darkfield can be important in image enhancement. Conventional darkfield imaging devices such as conventional darkfield microscopes use complex and expensive components to generate a darkfield image. In addition, conventional darkfield imaging devices can be difficult to operate and require operator training.

B. The SWEDA Structure

In certain embodiments, one or more simple SWEDA structures can be used to generate a darkfield for sensing and imaging purposes. A simple SWEDA structure includes a layer (e.g., metallic layer) with at least one surface having grooves around a darkfield aperture (SWEDA). The SWEDA structure operates by cancelling background light before it is transmitted through the darkfield aperture to a light sensor—predetection background cancellation. To function in this way, the features of the SWEDA structure are designed to induce a surface wave that balances and cancels out the direct transmission of light of a uniform light field from an illumination source. When the uniform field is disrupted by, for example, the presence of an object in the field, the balance is upset and light passes through the darkfield aperture. By implementing one or more SWEDA structures onto a light detector, the apertures receiving the uniform light transmit little or no light to the light detector and thereby create a darkfield for the light detector. A sensing device equipped with darkfield apertures can intrinsically cancel background light prior to signal detection, accomplishing darkfield sensing for a coherent light field in a robust, compact, and simple format.

Since the exact balance between the surface wave and direct transmission components is highly delicate and can be easily disrupted by the non-uniformity of the localized light field or light field deviation from normal incidence, the SWEDA structure can be used to suppress background light and allow for darkfield sensing and imaging. In some cases, a SWEDA structure can provide an image contrast enhancement of 27 dB. A detection system that can effectively suppress background light contributions (prior to detection) and allow detection of small signals in extremely compact device architectures can be advantageous for a broad range of applications from on-chip bio-sensing to metrology and microscopy.

In many embodiments, the design features of the SWEDA structure can be optimized to cancel out the direct transmission of light under a uniform light field. In some embodiments, the features can also be optimized to enhance the direct transmission of light through the darkfield aperture under a non-uniform light field. This enhancement will create a higher contrast image. In yet other embodiments, the features of the SWEDA structure can be designed to be highly sensitive to polarized light so that the SWEDA structure can be use in a polarization sensor.

The underlying principle of certain embodiments of the SWEDA structure and other surface wave assisted structures is based on the light interaction between subwavelength features on a metal-dielectric interface. This interaction can be found in T. Ebbesen, et al., "*Extraordinary optical transmission through sub-wavelength hole arrays,*" Nature, vol. 391, pp. 667-669, 1998, T. Thio, et al., "*Enhanced light transmission through a single subwavelength aperture,*" Opt. Lett., vol. 26, pp. 1972-1974, 2001, H. Lezec, et al., "*Beaming light from a subwavelength aperture,*" Science, vol. 297, pp. 820-822, 2002, T. Thio, et al., "*Giant optical transmission of sub-wavelength apertures: physics and applications,*" Nanotechnology, vol. 13, pp. 429-432, 2002, H. Lezec and T. Thio, "*Diffracted evanescent wave model for enhanced and suppressed optical transmission through subwavelength hole arrays,*" Optics express, vol. 12, pp. 3629-3651, 2004, R. Hollingsworth and R. Collins, "*Plasmon enhanced near-field optical probes,*" ed: Google patents, 2005, H. Schouten, et al., "*Plasmon-assisted two-slit transmission: Young's experiment revisited,*" Physical Review Letters, vol. 94, p. 53901, 2005, L. Chen, et al., *"Role of radiation and surface plasmon polaritons in the optical interactions between a nano-slit and a nano-groove on a metal surface,"* Optics Express, vol. 14, pp. 12629-12636, 2006, G. Gay, et al., "*The optical response of nanostructured surfaces and the composite diffracted evanescent wave model,*" Nat Phys, vol. 2, pp. 262-267, 2006, P. Lalanne and J. Hugonin, "*Interaction between optical nano-objects at metallo-dielectric interfaces,*" Nature Physics, vol. 2, p. 551, 2006, L. Aigouy, et al., "*Near-field analysis of surface waves launched at nanoslit apertures,*" Physical Review Letters, vol. 98, p. 153902, 2007, D. Pacifici, et al., "All-*optical modulation by plasmonic excitation of CdSe quantum dots,*" Nature photonics, vol. 1, pp. 402-406, 2007, A. Drezet, et al., "Miniature plasmonic wave plates," Physical Review Letters, vol. 101, p. 43902, 2008, E. Laux, et al., "*Plasmonic photon sorters for spectral and polarimetric imaging,*" Nature Photonics, vol. 2, pp. 161-164, 2008, H. Liu and P. Lalanne, "*Microscopic theory of the extraordinary optical transmission,*" Nature, vol. 452, pp. 728-731, 2008, D. Pacifici, et al., *"Universal optical transmission features in periodic and quasiperiodic hole arrays,*" Optics Express, vol. 16, pp. 9222-9238, 2008, B. Ung and Y. Sheng, "*Optical surface waves over metallo-dielectric nanostructures: Sommerfeld integrals revisited,*" Optics Express, vol. 16, pp. 9073-9086, 2008, and G. Gbur, et al., "*Achieving superresolution in near-field optical data readout systems using surface plasmons,*" Applied Physics Letters, vol. 87, p. 191109, 2005, which are hereby incorporated by reference in their entirety for all purposes.

Surface waves are induced by the subwavelength features on the metal-dielectric interface. Examples of surface waves and their behavior can be found in S. Maier, "*Plasmonics: fundamentals and application,*" Springer Verlag, 2007, Lezec and T. Thio, "*Diffracted evanescent wave model for enhanced and suppressed optical transmission through subwavelength hole arrays,*" Optics express, vol. 12, pp. 3629-3651, 2004, L. Chen, et al., "*Role of radiation and surface plasmon polaritons in the optical interactions between a nano-slit and a nano-groove on a metal surface,*" Optics Express, vol. 14, pp. 12629-12636, 2006, G. Gay, et al., *"The optical response of nanostructured surfaces and the composite diffracted evanescent wave model,"* Nat Phys, vol. 2, pp. 262-267, 2006, P. Lalanne and J. Hugonin, "*Interaction between optical nano-objects at metallo-dielectric interfaces,*" Nature Physics, vol. 2, p. 551, 2006, L. Aigouy, et al., "*Near-field analysis of surface waves launched at nanoslit apertures,*" Physical Review Letters, vol. 98, p. 153902, 2007, H. Liu and P. Lalanne, "*Microscopic theory of the extraordinary optical transmission,*" Nature, vol. 452, pp. 728-731, 2008, and B. Ung and Y. Sheng, "*Optical surface waves over metallo-dielectric nanostructures: Sommerfeld integrals revisited,*" Optics Express, vol. 16, pp. 9073-9086, 2008, which are hereby incorporated by reference in their entirety for all purposes. Appropriately designed grooves around an aperture have been shown to change the total amount of light transmission through the aperture as shown in T. Thio, et al., "Enhanced light transmission through a single subwavelength aperture," Opt. Lett., vol. 26, pp. 1972-1974, 2001, T. Thio, et al., "*Giant optical transmission of sub-wavelength apertures: physics and applications*," Nanotechnology, vol. 13, pp. 429-432, 2002, H. Lezec and T. Thio, "*Diffracted evanescent wave model for enhanced and suppressed optical transmission through subwavelength hole arrays*," Optics express, vol. 12, pp. 3629-3651, 2004, G. Gay, et al., "*The optical response of nanostructured surfaces and the composite diffracted evanescent wave model*," Nat Phys, vol. 2, pp. 262-267, 2006, P. Lalanne and J. Hugonin, "*Interaction between optical nano-objects at metallo-dielectric interfaces*," Nature Physics, vol. 2, p. 551, 2006, D. Pacifici, et al., "*All-optical modulation by plasmonic excitation of CdSe quantum dots*," Nature photonics, vol. 1, pp. 402-406, 2007, and E. Laux, et al., "*Plasmonic photon sorters for spectral and polarimetric imaging*," Nature Photonics, vol. 2, pp. 161-164, 2008, which are hereby incorporated by reference in their entirety for all purposes.

The behavior of a groove-based SWEDA structure and other surface wave assisted structures can be intuitively explained as follows. Surface waves are charge density waves that can be induced and sustained in certain types of materials (e.g., metals). Optical waves and surface waves have substantially different dispersion relationships. Yet, optical waves can be coupled into surface waves and vice-versa by matching their energy and momentum using grooves in the SWEDA structure or other surface wave assisted structures. This wave coupling on the aperture structures can be intuitively explained as follows. When light falls on the patterned groove pattern, it couples into a surface wave. By choosing a groove periodicity (i.e., distance between grooves) such that the surface wave launched at each groove adds up in phase, a strong propagative surface wave can be generated that is directed towards the aperture. The surface wave can then be converted back to a propagating optical wave at the central aperture. In essence, the groove structure serves as an antenna for light collection and uses the surface wave to transport the collected optical power to the aperture.

Embodiments of SWEDA structures provide one or more technical advantages. Generally, embodiments of SWEDA structures are advantageous because they provide a simple, compact, and relatively inexpensive design for effectively generating a darkfield. In one embodiment, a SWEDA structure has been shown to have a darkfield suppression factor of at least 1000. One advantage of embodiments is that the SWEDA structure is simple and compact, and easily adapted to being used on various sensing/imaging devices in a broad range of applications from on-chip bio-sensing to metrology and microscopy. For example, the SWEDA structure can be fabricated onto a sensor chip (e.g., CMOS sensor chip) which is easily implemented by plugging it into an imaging device (e.g., standard microscope). Another advantage of certain embodiments is that the SWEDA structure suppresses the background signal before detection by the sensor, so that a sensing/imaging device employing the SWEDA structure does not need an exotic and specialized condenser, or other expensive and bulky components to create a darkfield. Since the SWEDA structure alters the illumination light field, the collection optics of an imaging device employing the SWEDA structure can be unchanged. In addition, an operator using this imaging device employing the SWEDA structure(s) would not require extensive training on using the darkfield capabilities.

A SWEDA structure includes an opaque or semi-opaque aperture layer with a darkfield aperture surrounded by a plurality of grooves (e.g., corrugation). The grooves may be defined in the aperture layer or in a separate layer from the aperture layer. The plurality of grooves can be in any suitable pattern such as a circular groove pattern, a linear groove pattern, a rectangular groove pattern, an oval groove pattern, a checkerboard groove pattern, etc. Due to its circular symmetry nature, a SWEDA structure with grooves in a circular groove pattern can provide a polarization-independent behavior for signal detection and imaging. That is, a SWEDA structure having grooves in a circular groove pattern can suppress bright normal-incidence background regardless of the incident light field's polarization state. On the other hand, a SWEDA structure with grooves in a linear groove pattern can be highly sensitive to the polarization state of the incident light.

C. SWEDA Structure with a Circular Groove Pattern

Figure 19:
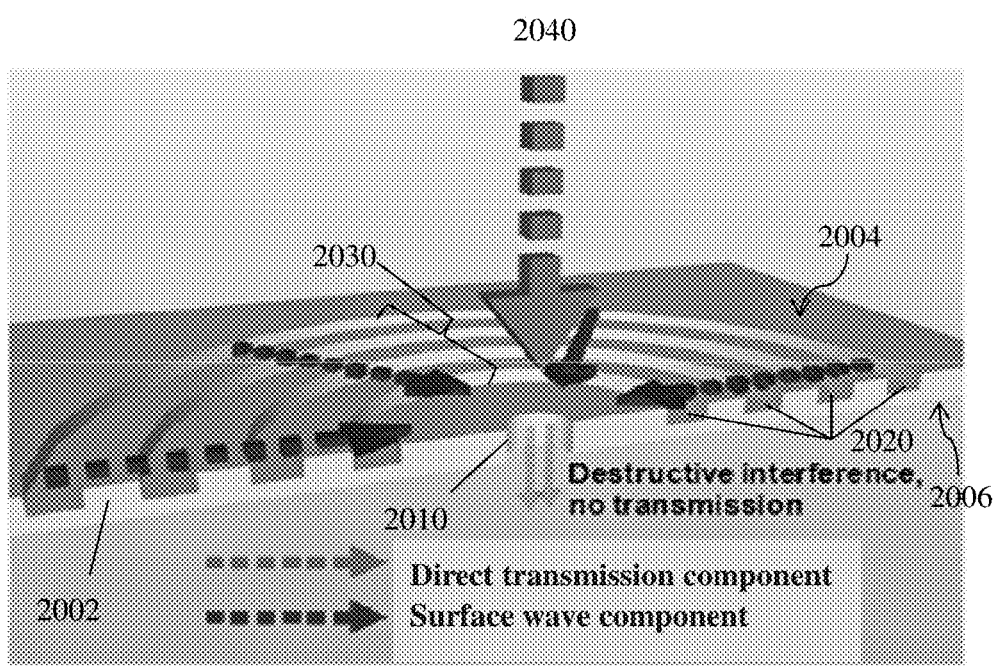
FIG. 19 is a schematic drawing of a SWEDA structure with a circular groove pattern, according to embodiments of the invention.

FIG. 19 is a schematic drawing of a SWEDA structure 2000 with a circular groove pattern, according to an embodiment of the invention. In this illustration, the SWEDA structure 2000 comprises an opaque or semi-opaque aperture layer 2002 having a first surface 2004 and a second surface 2006. The aperture layer 2002 has a darkfield aperture 2010 surrounded by a plurality of circular grooves 2020 forming a (groove pattern) corrugation 2030 in the first surface 2004. An illumination source 2040 provides a uniform incident light field to the first surface 2004. In this illustration, the surface wave component destructively interferes with the direct transmission component cancelling it out so that no light is transmitted through the darkfield aperture 2010. Although the SWEDA structure 2000 of this example is shown to have grooves 2020 only on the first surface 2004, in other embodiments the SWEDA structure 2000 can have grooves 2020 on a second surface 2006, or on both first and second surfaces 2004 and 2006. Due to the polarization-independent nature of the circular-groove based SWEDA, it can be used to suppress background light regardless of the polarization state of the incident light field.

An aperture layer 2002 of embodiments can refer to an opaque or semi-opaque layer having at least a first surface 2004 and a second surface 2006 and at least one aperture (e.g., a darkfield aperture 2010). The aperture layer 2002 of embodiments also includes one or more grooves 2020 around the aperture 2010. In other embodiments, the grooves 2020 may be in another layer separate from the aperture layer 2002. Grooves 2020 may be defined in the first surface 2004, in the second surface 2006, or in both the first and second surfaces 2004 and 2006.

The aperture layer 2002 can be made of any suitable material(s). For example, the aperture layer 2002 may be a metallic layer. In another example, the aperture layer 2002 may consist of a metallic layer over a transparent plate (e.g., a glass plate). The aperture layer 2002 can have any suitable dimensions (thickness, length, width). The thickness of the aperture layer 2002 can be any suitable thickness such as, for example, 30, 20 or 10 microns. In some cases, the type of material used in the aperture layer 2002 can affect roughness of the aperture layer 2002 and the sharpness of the features in the aperture layer 2002 which can affect the darkfield suppression factor.

As used herein, an aperture such as the darkfield aperture 2010 refers to any suitable light transmissive region of any suitable size (e.g., 1 nm, 10 nm, 20 nm etc.) and any suitable cross sectional shape (e.g., circular, rectangular, oval, C-shaped, etc.). In many cases, an aperture is a hole. In some of these cases, the hole can be at least partially filled with a transparent material.

Although a single aperture is shown in illustrated embodiments of SWEDA structures 2000 or other surface wave assisted structures, other embodiments may include multiple apertures in the aperture layer 2002 of the aperture structures. Using multiple apertures can increase the amount of light transmitted through the aperture structure, which can increase light collection efficiency. In one embodiment, a SWEDA structure 2000 has multiple C-shape apertures to increase light collection efficiency. An example of a C-shaped aperture can be found in X. Shi, et al., "*Ultrahigh light transmission through a C-shaped nanoaperture*," Optics letters, vol. 28, pp. 1320-1322, 2003, which is hereby incorporated by reference in its entirety for all purposes.

A groove 2020 can refer to a furrow or channel defined in a surface. Each groove 2020 can have any suitable cross sectional shape and have any suitable cross-section dimensions. Although the grooves 2020 in many illustrated embodiments are shown to have a rectangular cross-sectional shape, the grooves 2020 in other embodiments may have other suitable cross-sectional shapes, such as a semi-circular cross-section, oval cross-section, triangular cross-section, etc. Each groove 2020 can also have dimensions of any suitable value. Groove depth, d, can refer to the depth of a groove 2010. Groove depth, w, can refer to the width of a groove 2010. Groove length, l, can refer to the length of a groove 2010 such as a length of a linear groove 2010. Groove diameter, D, can refer to the diameter of a circular groove 2010.

A groove pattern or plurality of grooves 2030 can refer to the arrangement of the grooves around a particular aperture in the aperture structure (e.g., SWEDA structure 2000 or other surface wave assisted structure). The groove pattern 2030 can be any suitable pattern such as a circular groove pattern (e.g., groove pattern shown in FIG. 19), a linear groove pattern (e.g., groove pattern shown in FIG. 14), a rectangular groove pattern, an oval groove pattern, a checkerboard groove pattern (e.g., groove pattern shown in FIG. 13), etc. Each set of adjacent grooves in a groove pattern 2030 can be separated by the same distance or can be separated by any suitable distance. The groove pattern 2030 can have any suitable number of grooves 2020 (e.g., 2, 3, 4, 5, 10, 20, etc.).

An illumination source 2040 can refer to any suitable device or other source of light such as LED, laser, white light source with a color filter, etc. The light provided by illumination source 2040 can be of any suitable wavelength and intensity. Also, the light can include polarized and/or unpolarized light. Suitable illumination sources 2040 are naturally and commercially available. In some embodiments, the illumination source 2040 can be a component of the device employing the SWEDA structure 2000 or other surface wave assisted structure. In other embodiments, the illumination source 2040 can be a separate from the device employing a SWEDA structure 2000 or other surface wave assisted structure. The illumination source 2040 can be placed in any suitable location and positioned in any suitable direction to provide appropriate light or incidence angle to the SWEDA structure 2000 or other surface wave assisted structure. In some embodiments, multiple illumination sources 2040 provide light in one or more directions. In other embodiments, a single illumination source 2040 provides light in a single direction.

Figure 20:
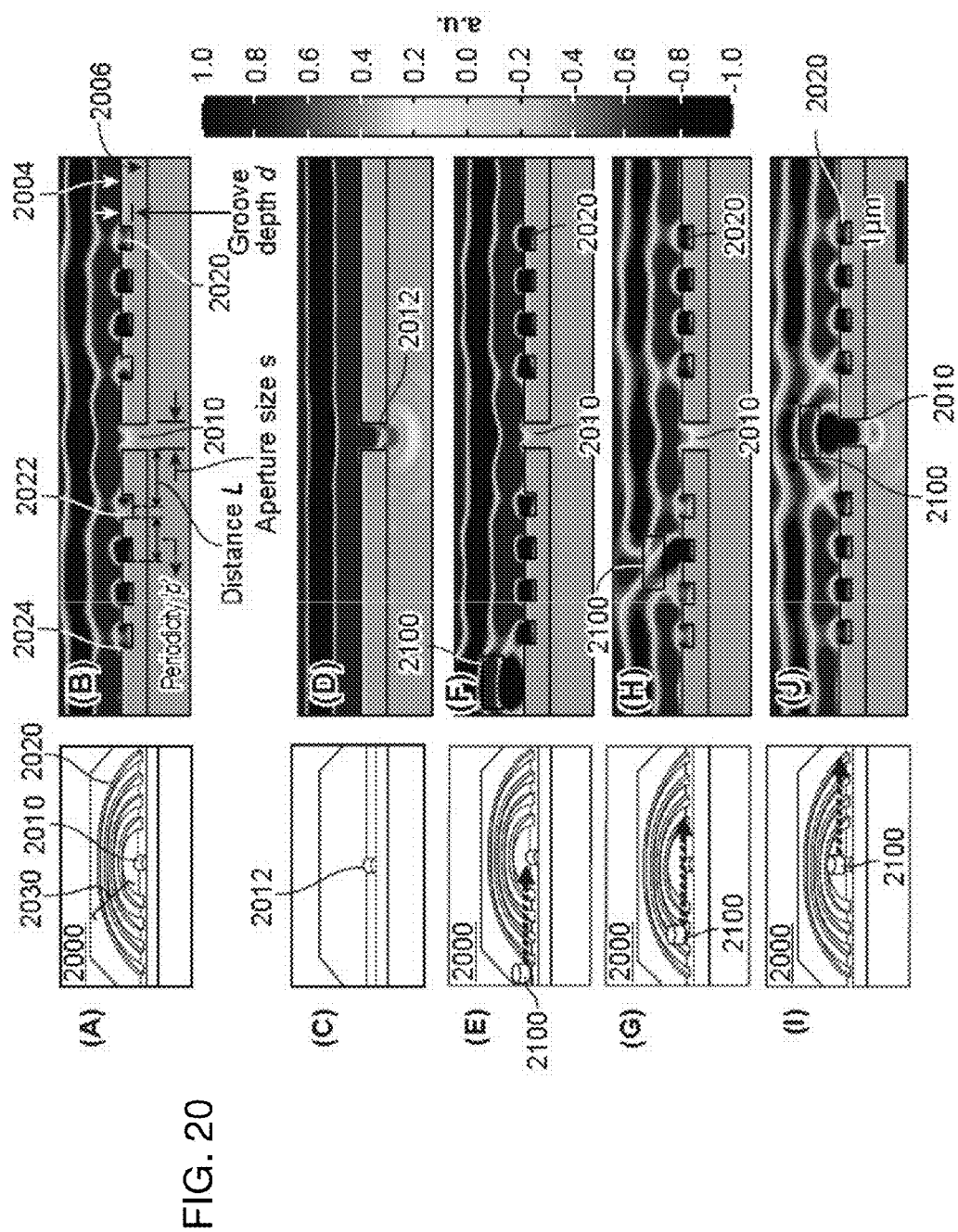
FIG. 20(A) is a schematic drawing of a portion of a SWEDA structure with a circular groove pattern, according to an embodiment of the invention.
FIG. 20(B) is a simulation of the real part of the light field around the SWEDA structure in FIG. 20(A) under uniform incident light.
FIG. 20(C) is a schematic drawing of a portion of a simple single aperture.
FIG. 20(D) is a simulation of the real part of the light field around the simple single aperture of FIG. 20(C) under uniform incident light.
FIGS. 20(E), 20(G) and 20(I) are schematic drawings showing the translation of a cylindrical dielectric object (scatterer) across a first surface of the SWEDA structure of FIG. 20(A) from the outermost groove to the darkfield aperture, according to an embodiment of the invention.
FIGS. 20(F), 20(H) and 20(J) are schematic drawings showing the translation of a cylindrical dielectric object across a first surface of the SWEDA structure of FIG. 20(A), according to an embodiment of the invention.

FIG. 20(A) is a schematic drawing of a portion of a SWEDA structure 2000 with a circular groove pattern 2030, according to an embodiment of the invention. FIG. 20(B) is a simulation of the real part of the light field around the SWEDA structure in FIG. 20(A) under uniform incident light, according to an embodiment of the invention. FIG. 20(B) also shows some of the design features of a SWEDA structure 2000. SWEDA structure 2000 comprises a darkfield aperture 2010 having a darkfield aperture size ("s"). The SWEDA structure 2000 also includes circular grooves 2020 that form a plurality of grooves 2030 around the darkfield aperture 2010. The plurality of grooves 2020 comprises four circular grooves 2020 including an innermost groove 2022 and an outermost groove 2024. The plurality of grooves 2020 also comprises a number of grooves ("n") equal to 4. In other cases, the SWEDA structure 2000 can have any number of grooves (e.g., 2, 5, 10, 20, etc.). Each circular groove 2020 has a groove depth ("d"). The plurality of grooves 2020 also has a groove periodicity or period ("p"), which can refer to the distance between adjacent grooves 2020. Although the illustrated example shows a constant distance, other embodiments may have varying distance between adjacent grooves 2020. The SWEDA structure 2000 also has a distance ("L") between the centerline of the innermost groove 2022 and the outer edge of the darkfield aperture 2010.

In many embodiments, the design features of the SWEDA structure 2000 or other surface wave assisted structures can be adjusted to modify the system characteristic(s) of the aperture structure. In some cases, the design features can be optimized to maximize selected system characteristic(s) of the aperture structure. Some examples of system characteristics can include darkfield suppression factor, enhancement factor polarization sensitivity, imaging resolution, light collection efficiency, and optical transfer function. The darkfield suppression factor refers to the ratio of the total power transmission through a simple hole (without grooves) to the total power transmission through a darkfield aperture 2010 under a uniform light field. The enhancement factor can refer to the ratio of the total power transmission through the aperture to the total power transmission through a simple hole under a non-uniform light field. Another example of a system characteristic is a geometrical restriction such as overall SWEDA structure size to ensure a compact design, darkfield aperture size, groove depth, or periodicity. These geometric restrictions may be based on fabrication limitations.

The following four design parameters (features) primarily impact system characteristics (performance) of the SWEDA structure 2000 or other surface wave assisted structures: 1) groove periodicity p and groove depth, d, 2) number of grooves n in the aperture structure 2000, 3) aperture size, s, and 4) distance, L, between the centerline of the innermost groove 2022 and the outer edge of the darkfield aperture 2010.

Groove periodicity or period, p, can refer to the distance between adjacent grooves 2020 in the SWEDA structure 2000 or other surface wave enabled grooved structure. The groove periodicity can be a constant value between all the grooves 2020 in a plurality of grooves 2030 in some cases. In other cases, the groove periodicity may vary between grooves in a plurality of grooves 2030. For example, a plurality of grooves may have a gradually increasing/decreasing changing periodicity. Groove periodicity, p and groove depth, d can be adjusted to control the magnitude (amplitude) of the surface wave coupled in the SWEDA structure 2000. For example, the SWEDA structure 2000 can be designed so that the groove periodicity p is equal to a multiple (1, 2, etc.) of the wavelength of the surface wave to maximize the magnitude. In other examples, the groove periodicity p can be adjusted to be a distance more than or less than a multiple of the wavelength of the surface wave in order to finely tune the amplitude of the surface wave component to exactly match the amplitude of the direct transmission component. In other embodiments, other factors may be considered in selecting the groove periodicity and groove depth such as fabrication restraints.

The number of grooves, n, can refer to the number of grooves 2010 in a plurality of grooves 2030 of a particular SWEDA structure 2000 or other surface wave assisted structure. The number of grooves, n, in the plurality of grooves 2030 can also be adjusted to control the magnitude (amplitude) of the surface wave coupled into the aperture structure. The magnitude of the coupled surface wave increases as a function of the number of grooves, n. The number of grooves, n, also determines the size of the overall SWEDA structure 2000 or other surface wave assisted structure. In some cases, the size of the overall aperture structure can be limited by the density of aperture structures needed to provide a required image resolution. Moreover, a smaller size of the aperture structure may be desired for compactness considerations. These factors and other suitable factors can be considered and/or weighted in determining the number of grooves, n, in the SWEDA structure 2000 or other surface wave assisted structure.

Aperture size, s, can refer to a dimension of the aperture. For example, the aperture size, s, can refer to a diameter of a circular aperture. In another example, aperture size, s, can refer to the length or width of a rectangular aperture. Although circular apertures are shown in many illustrated embodiments, other shaped apertures can be used in other embodiments. The aperture size, s, can be adjusted to control the magnitude (amplitude) of the direct transmission component. In addition, the aperture size, s, can also be restricted so that the direct light transmission is not multi-moded. Multimode light transmission can significantly complicate the destructive interference balancing act since destructive interference between the surface wave component and the direct transmission component would have to be achieved for all modes. These factors and other suitable factors can be considered and/or weighted in determining the aperture size, s.

The distance, L, can refer to the distance between the centerline of the innermost groove 2022 of the groove pattern 2030 and the outer edge of the aperture. The distance, L can determine the phase of the surface wave and thus, the phase difference between the surface wave induced and the direct transmission components. To accomplish exact cancellation of the components, the distance, L, can be selected so that the surface wave is 180 degrees out-of-phase with the direct transmission component.

In addition to these four design parameters, other design parameters can affect the system characteristics. In some cases, the type of groove pattern can affect the system characteristics. For example, the selection of a linear groove pattern can increase polarization sensitivity and/or lower darkfield suppression factor. In other cases, the type of cross-sectional profile of the grooves 2020 can also affect the system characteristics. For example, certain cross-sectional profiles do not have a sharp edge as grooves 2020, and it can be used to tune the surface wave component. However, from the fabrication point of view, the profile of the grooves 2020 is not as easy to control as other parameters. In some cases, the width and length of the grooves can also affect the system characteristics.

In some exemplary embodiments, the design features of the SWEDA structure 2000 or other surface wave assisted structure are optimized to maximize the darkfield suppression factor to generate the most effective darkfield. In these embodiments, the features of the SWEDA structure 2000 are optimized so that the surface wave component induced by the plurality of grooves 2020 exactly balances and mutually cancels the direct transmission component of the illumination source 2040. This design maximizes the suppression factor and can result in a near-zero transmission through the darkfield aperture 2010 under uniform normal-incidence illumination from the illumination source 2040. Under non-uniform illumination, the balance between the components is disrupted and light is transmitted through the darkfield aperture 2010. In one embodiment, the features of the SWEDA structure 2000 are optimized to maximize the darkfield suppression factor and maximize the enhancement factor during non-uniform illumination conditions. In this way, the amplitude of the light transmitted through the object 2100 can be increased to provide greater contrast, which is advantageous for weak signal transmission. In another embodiment, the features of the SWEDA structure 2000 are also optimized to be sensitive to the polarization of light.

For example, the design features (parameters) of the SWEDA structure 2000 can be optimized to maximize the darkfield suppression factor by selecting design features that induce a surface wave with an amplitude equivalent (balanced) to that of the direct transmission component, and 180 degrees out of phase from the direct transmission component. In one case, the amplitude of the surface wave can be modified by changing the periodicity p and groove depth d. The aperture size s can then be selected so that the amplitude of the surface wave component is equal to the amplitude of the direct transmission component. The distance L between the innermost groove 2022 and the darkfield aperture 2010 can then be selected so that the surface wave is 180 degrees out-of-phase with the direct transmission component. In this way, the geometrical features of the SWEDA structure 2000 can be selected so that the surface wave will balance the direct transmission component under a uniform light field from an illumination source 2040. Since this condition critically depends on an exact balance of the two mentioned components, a small change in spatial distribution of the input light field intensity or phase will disrupt the destructive interference condition and permit significant light transmission through the aperture 2010. For example, an object 2100 located between the SWEDA structure 2000 and the illumination source 2040 can cause heterogeneity in the light field due to scatter which can disrupt the non-transmission condition allowing/enhancing light transmission through the darkfield aperture 2010. In this way, the design features can produce the highest suppression factor and optimal darkfield.

In the context of high sensitivity optical signal detection, the advantage of a SWEDA structure 2000 with a high suppression factor can be easily appreciated. This SWEDA structure 2000 can effectively suppress a uniform normal-incidence light from reaching the underlying sensor and instead only permit highly localized light field variations or light fields at non-zero incidence angles to pass through and be detected. As such, the underlying sensor no longer needs to contend with background light and its associated noise fluctuation terms. The bit depth can also be optimized and devoted to the detection of the weaker light field variations. Used in an appropriate manner, such devices can potentially allow for greater signal detection sensitivity in weak-signal-buried-in-high-background scenarios. This method also enables a new way to build darkfield microscopes on the sensor level that does not rely on elaborate bulky optical arrangements.

In some embodiments, a simulation program or a suitable algorithm can be used to map out the interplay of the design parameters of the SWEDA structure 2000 or other surface wave assisted structures to one or more system characteristics. For example, the simulation program or algorithm can model the SWEDA structure 2000 (or other surface wave assisted structure) and determine the behavior of the light field at the SWEDA structure 2000 (or other surface wave assisted structure) due to an illumination source 2040 and/or interfering object (specimen). Exemplary simulation programs are commercially available. An example of a commercially available simulation program is CST Microwave Studio® simulation program. In one embodiment, the simulation program can be used to determine an optimal set of design parameters that will maximize/minimize one or more system characteristics (e.g., suppression factor).

In an exemplary embodiment, a simulation program was used to simulate a SWEDA structure 2000 having a set of circular grooves 2020 around a darkfield aperture 2010. The simulations were used to optimize the design parameters to maximize the suppression factor. In one case, a set of optimal design parameters was determined that maximized the suppression factor to about 6640 where the incident light field has a nominal wavelength of 738 nm. These optimal design parameters were distance (between aperture and innermost groove) L=774.3 nm, period p=560 nm, thickness of gold=340 nm, darkfield aperture size s=300 nm, groove depth d=140 nm, and refraction index of the dielectric substrate=1.5. An example of a SWEDA structure 2000 having these optimal design parameters is shown in FIGS. 20(A), 20(E), 20(G) and 20(I). The simulations of the electric field distributions around the SWEDA structure 2000 having these optimal design parameters are shown in FIGS. 20(B), 20(F), 20(H) and 20(J). FIG. 20(C) is a schematic drawing of a simple single aperture 2012. The simulation of the electric field distribution of the simple single aperture 2012 under a uniform light field is shown in FIG. 20(D).

Referring again to FIGS. 20(A) and 20(B), the illustrated SWEDA structure 2000 is under a uniform light field so that little to no light is transmitted through the darkfield aperture 2010 due to the destructive interference of the surface wave and the direct transmission components. For comparison purposes, FIG. 20(C) is a schematic drawing of a portion of a simple single aperture 2010. FIG. 20(D) is a simulation of the real part of the light field around the simple single aperture 2010 of FIG. 20(C) under uniform incident light. In comparison to the SWEDA structure 2000 in FIG. 20(D), the simulation in FIG. 20(D) shows significant transmission through the single aperture 2012. In some cases, the transmission through the simple single aperture 2012 of FIG. 20(C) can be about 1200 times larger than the transmission through the darkfield aperture 2010 in the SWEDA structure 2000 of FIG. 20(A).

FIGS. 20(E), 20(G) and 20(I) are schematic drawings showing the translation of a cylindrical dielectric object 2100 (scatterer) across a first surface 2004 of the SWEDA structure 2000 of FIG. 20(A) from the outermost groove 2024 to the darkfield aperture 2010, according to an embodiment of the invention. FIGS. 20(F), 20(H) and 20(J) are schematic drawings showing the translation of a cylindrical dielectric object 2100 across a first surface of the SWEDA structure 2000 of FIG. 20(A), according to an embodiment of the invention. In this example, the dielectric object 2100 has the following dimensions: radius 300 nm, thickness 200 nm, displacement height 300 nm, and permittivity 2.25. In other embodiments, the dielectric object 2100 can have any suitable dimensions.

Figure 21:
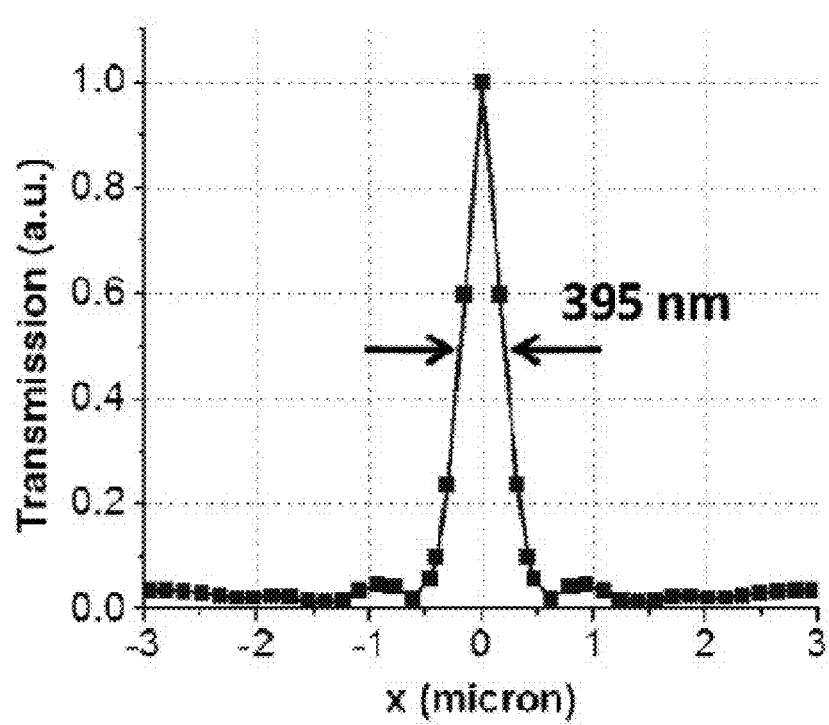
FIG. 21 is a graph of the transmission signal curve from the SWEDA structure as the scattering cylindrical dielectric object moves across a first surface of the SWEDA structure, according to an embodiment of the invention.

FIG. 21 is a graph of the transmission signal curve from the SWEDA structure as the scattering cylindrical dielectric object 2100 moves across a first surface 2004 of the SWEDA structure 2000, according to an embodiment of the invention. The graph shows the transmission through the darkfield aperture 2010 as a function of the distance of the dielectric object 2100 from the centerline of the darkfield aperture 2010. As shown in FIGS. 20(J) and 21, the SWEDA structure 2000 begins to transmit light significantly when the dielectric object 2100 is present directly above the darkfield aperture 2010. In this position, the dielectric object 2100 is significantly perturbing the direct transmission component and consequently, disrupting the delicately balanced destructive interference condition. The presence of the dielectric object 2100 adjacent to the grooves 2020 also perturbs the distribution around the center aperture 2010 to a certain extent as well, as shown in FIGS. 20(E) and 20(H). However, the impact is much less significant as shown in FIG. 20(F). This can be well appreciated by noting that the generation of a surface wave occurs over the entire area associated with the grooves 2020 and localized changes of the light field over the area have a diminished impact on the overall surface wave component. As a whole, this simulation indicates that the SWEDA structure 2000 is maximally sensitive to light field heterogeneity directly above the darkfield aperture 2010 (SWEDA).

Figure 22A:
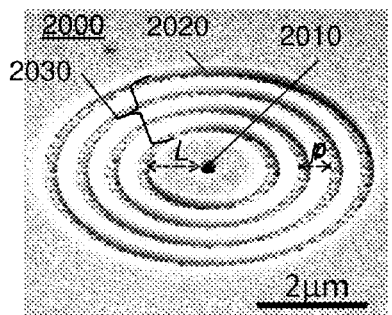
FIG. 22A is a scanning electron microscope image of a fabricated SWEDA structure having a circular groove pattern, according to an embodiment of the invention.

In one example, the affect of distance, L, on transmission was tested for a SWEDA structure 2000 having a circular groove pattern 2030 of an embodiment. In this example, SWEDA structures 2000 were fabricated by focus ion beam milling. The SWEDA structures 2000 in this embodiment has the optimal design parameters of periodicity p=560 nm, layer (gold) thickness=340 nm, darkfield aperture size s=300 nm, groove depth d=140 nm, and refraction index of the dielectric substrate=1.5, and a distance L ranging from 540 to 1020 nm. A simple single hole 2012 without the groove structure and having the same diameter as the darkfield aperture 2010 was also fabricated and tested as a control. A tunable wavelength laser was used as the illumination source 2040. The transmissions through the apertures were collected by an inverted microscope with a 20× objective lens. FIG. 22A is a scanning electron microscope (SEM) image of a typical SWEDA structure 2000 fabricated in this example, according to an embodiment of the invention.

Figure 22B:
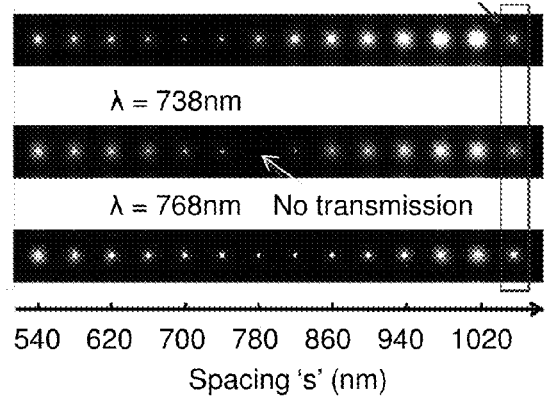
FIG. 22B includes the optical transmission images of thirteen (13) fabricated SWEDA structures and the reference simple single hole at normal incidence for three wavelengths: $\lambda=708$ nm, $\lambda=738$ nm and $\lambda=768$ nm, as a measure of distance L, according to an embodiment of the invention.
Figure 22C:
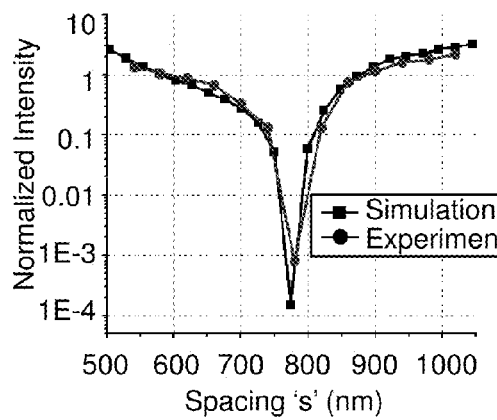
FIG. 22C is a plot of simulated and experimental transmission intensity at wavelength of 738 nm for SWEDA structures, having distance, L, ranging from 540 to 1020 nm., according to an embodiment of the invention.

FIG. 22B shows the optical transmission images of thirteen (13) fabricated SWEDA structures 2000 and the reference simple single hole 2012 at normal incidence for three wavelengths: λ=708 nm, λ=738 nm and λ=768 nm, as a measure of distance, L, according to an embodiment of the invention. As illustrated, the distance, L impacts the transmission of the SWEDA structures 2000. For each wavelength tested, a SWEDA structure 2000 with a different distance, L, had a minimum transmission. FIG. 22C is a plot of simulated and experimental transmission intensity at wavelength of 738 nm for SWEDA structures 2000 having distance, L, ranging from 540 to 1020 nm. From this plot, both the fabricated and simulated SWEDA structures 2000 with a distance, L=780 nm exhibited the desired near-zero transmission characteristics. The fabricated SWEDA structure 2000 had a measured suppression factor of 1230. In other words, this fabricated SWEDA 2000 structure transmitted 1230 times less light than an unadorned simple hole 2012 of size equal to that of the darkfield aperture 2010. Any discrepancy in the darkfield suppression factor between the fabricated and simulated SWEDA structures 2000 can be due to fabrication imperfections. Such imperfections could be mitigated by employing a sacrificial layer during fabrication to help preserve the sharpness of edges as described in J. Leen, et al., "*Improved focused ion beam fabrication of near-field apertures using a silicon nitride membrane*" Optics Letters, vol. 33, pp. 2827-2829, 2008, which is hereby incorporated by reference in its entirety for all purposes.

Figure 22D:
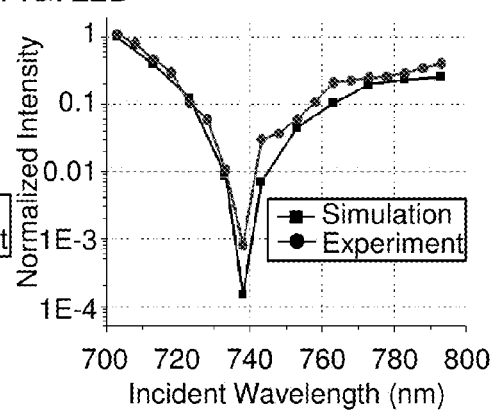
FIG. 22D is a plot of the normalized optical transmission signals of the SWEDA structure having a distance, L=780 nm at normal incidence for three wavelengths: $\lambda=708$ nm, $\lambda=738$ nm and $\lambda=768$ nm, according to an embodiment of the invention.
Figure 22E:
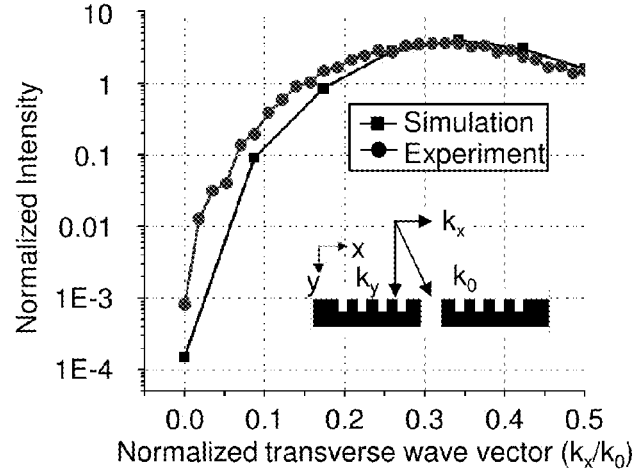
FIG. 22E is a plot of the normalized optical transmission signals as a function of normalized traverse wave vector ($k_x/k_0$), according to an embodiment of the invention.

FIG. 22D is a plot of the normalized optical transmission signals of the SWEDA structure 2000 having a distance, L=780 nm at normal incidence for three wavelengths: λ=708 nm, λ=738 nm and λ=768 nm, according to an embodiment of the invention. This plot shows a single minimum transmission for each wavelength and the transmission increasing monotonically away from this minimum. FIG. 22E is a plot of the normalized optical transmission signals as a function of normalized traverse wave vector ($k_x/k_0$), according to an embodiment of the invention. FIG. 22E represents the system transfer function of the SWEDA 2000 and shows that the SWEDA structure 2000 rejects the normal incident plane wave component and transmits other components with efficiency as dictated by this transfer function.

The ability to fully suppress a coherent background light as exhibited by embodiments of circular-groove based SWEDA structures 2000 can be useful for small signal detections in metrology applications. It is especially applicable in detection scenarios where the overall background intensities fluctuate with time. As our background subtraction occurs at the individual pixel level, SWEDA technology removes the need for balanced detection schemas. The pre-detection background subtraction, which is a light cancellation process, is also intrinsically more sensitive than post-detection cancellation schemas that are susceptible to intrinsic detection statistical variations. The inclusion of chemical reagents in the darkfield aperture 2010 can also turn such a SWEDA structure 2000 into a high-sensitivity sensor that can react to small refractive index changes of the reagents.

D. SWEDA Structure with Linear Groove Pattern

Embodiments of SWEDA structures 2000 with grooves in a linear groove pattern 2030 can be highly sensitive to the polarization state of the incident light. In some cases, SWEDA structures 2000 having linear groove patterns 2030 can be designed to serve as a highly compact and highly efficient polarization sensor.

FIG. 23A is a schematic drawing of a portion of a SWEDA structure 2000 with grooves 2010 in a linear pattern, according to an embodiment of the invention. The SWEDA structure 2000 includes a layer having a plurality of eight linear grooves 2020, four on each side of a central darkfield aperture 2010. Other embodiments can have more or fewer linear grooves 2020.

FIG. 23A illustrates that incoming TM polarized light can be collected and converted into a surface wave by the periodic grooves 2020 and then be recoupled into propagating light through the central aperture 2010. TM polarized light refers to light where the electric field is perpendicular to the groove structure. TE polarized light refers to light where the electric field is along the groove structure 2030. FIG. 23B illustrates that the incoming TE polarized light cannot be as effectively coupled into surface waves and transmission is induced in the absence of destructive interference.

FIG. 23C is a simulation of the TM case of a SWEDA structure 2000 having a linear groove pattern, according to an embodiment of the invention. The simulation shows the real part of the electric-field at λ=750 nm. In this embodiment, the SWEDA structure 2000 has optimal design parameters of distance L=658 nm, periodicity p=658 nm, layer (gold) thickness=340 nm, darkfield aperture size s=300 nm, groove depth d=140 nm, and refraction index of the dielectric substrate=1.5. In this embodiment, the TM darkfield suppression factor of the simulated SWEDA structure 2000 of this embodiment was 35,400. The TM case is described in Maier, S., "*Plasmonics: fundamentals and applications,*" Springer Verlag, 2007, which is hereby incorporated by reference in its entirety for all purposes. FIG. 23D is a simulation of the TE case of the SWEDA structure 2000 of FIG. 23C. The simulation shows the real part of the magnetic field at λ=750 nm. The simulation predicts the polarization extinction ratio of the two orthogonal polarization states is 42500. FIG. 23D also shows the electric-field distributions for the TE wave, from which can be shown the structure does transmit TE wave significantly, according to an embodiment of the invention.

The difference between the TM and TE cases also verifies the surface-wave-enabled mechanism of the linear-groove based SWEDA, since the surface wave can only be induced efficiently for TM polarization. From the simulations shown in FIGS. 23C and 23D, the linear-groove based SWEDA structure 2000 provides a polarization extinction ratio of 42500 for the two orthogonal polarization states.

In some exemplary embodiments, a SWEDA structure 2000 with grooves in a linear groove pattern can be used as a polarization sensor. Examples of such embodiments can be found in Section IV (F)(5). Since the polarization state of light will change during the interaction with chiral materials, this SWEDA structure 2000 of these embodiments can find some applications in on-chip detection of some chiral materials such as sugar, proteins and DNA as can be found in G. Fasman, Circular dichroism and the conformational analysis of biomolecules: Plenum Pub Corp, 1996, and in K. Minakawa, et al., "*Microchamber Device Equipped with Complementary Metal Oxide Semiconductor Optical Polarization Analyzer Chip for Micro Total Analysis System,*" Jpn. J. Appl. Phys., vol. 48, p. 04C192, 2009, which are hereby incorporated by reference in their entirety for all purposes.

Figure 24A:
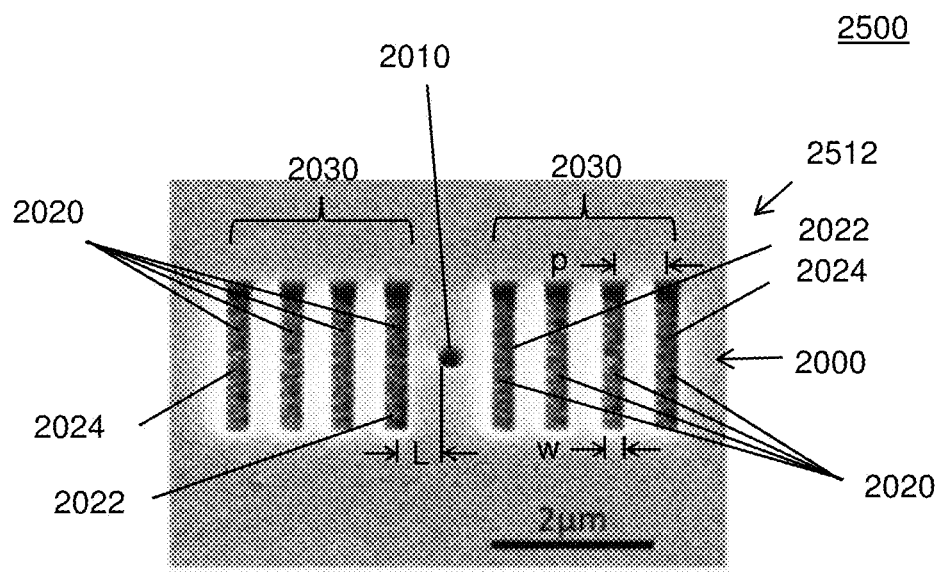
FIG. 24A is a scanning electron microscope image of a typical fabricated SWEDA structure with a linear groove pattern, according to an embodiment of the invention.
Figure 24B:
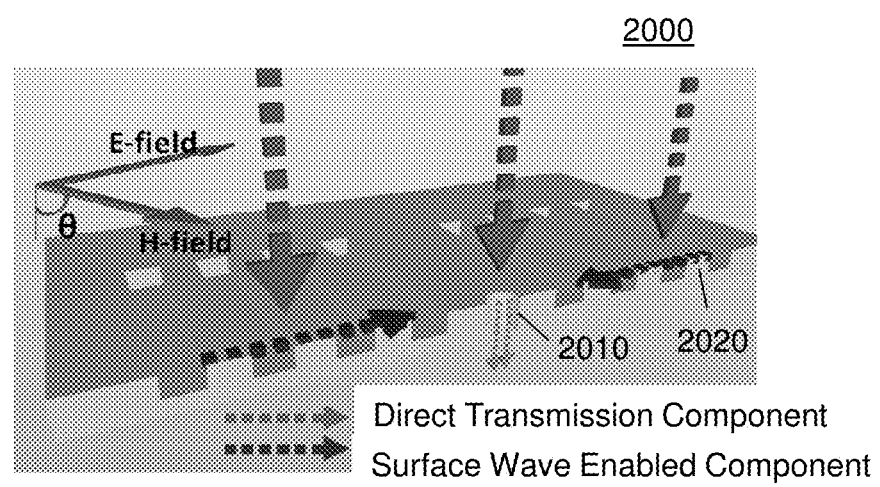
FIG. 24B is a schematic drawing of light incident with a polarization angle ("θ") on a SWEDA structure having a linear groove pattern, according to an embodiment of the invention.
Figure 24C:
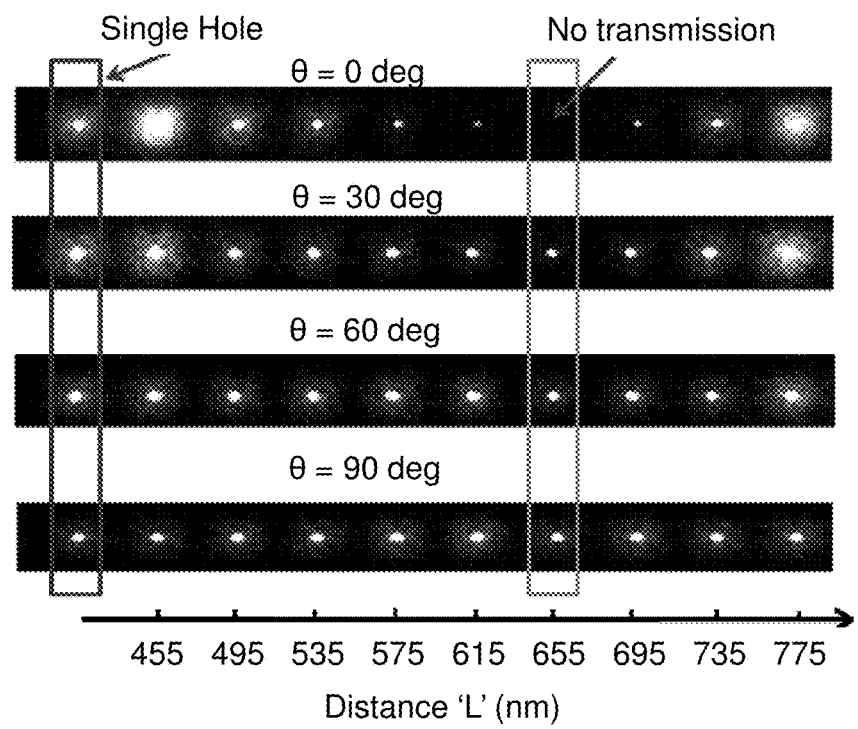
FIG. 24C shows the optical transmission images the nine (9) SWEDA structures having a linear groove pattern for different polarization angles at wavelength of 750 nm and the reference simple single hole at normal incidence for four different polarization angles: θ=0 degrees; θ=30 degrees; θ=60 degrees; and θ=90 degrees, according to an embodiment of the invention.

FIG. 24A is a SEM image of a fabricated SWEDA structure 2000 with a linear groove pattern, according to an embodiment of the invention. The SWEDA structure 2000 is part of a pixel of a SWEDA-based polarization sensor with high polarization sensitivity of an embodiment of the invention. The details of the pixel are described in Section IV (F)(5). FIG. 24B is a schematic drawing of light incident with a polarization angle ("θ") on a SWEDA structure 2000 having a linear groove pattern, according to an embodiment of the invention.

In one demonstration, the affect of distance L on transmission was tested for nine SWEDA structures 2000 having a linear groove pattern fabricated by FIB milling. The nine SWEDA structures 2000 had distances, L ranging from 455 nm to 775 nm. FIG. 24 shows the optical transmission images of the nine (9) SWEDA structures 2000 having a linear groove pattern for different polarization angles at wavelength of 750 nm and the reference simple single hole 2012 at normal incidence for four different polarization angles: θ=0 degrees; θ=30 degrees; θ=60 degrees; and θ=90 degrees, according to an embodiment of the invention.

Figure 24D:
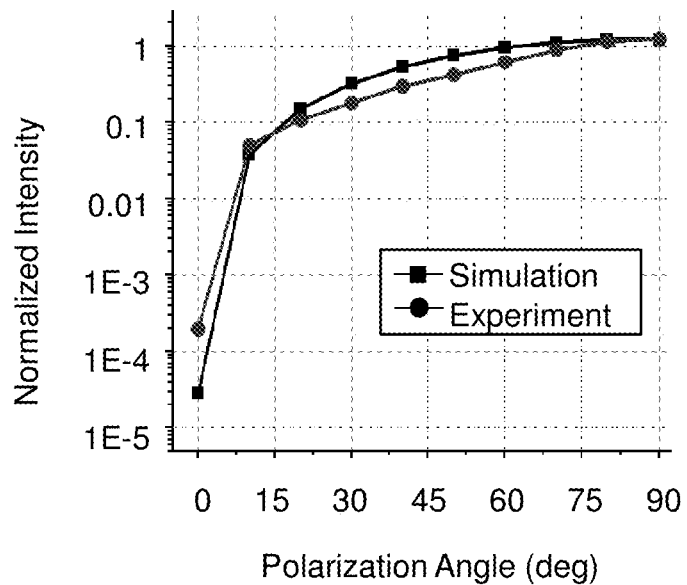
FIG. 24D is a graph of the normalized optical transmission signals of the SWEDA structures with a linear groove pattern plotted as a function of polarization angle, in accordance with an embodiment of the invention.

FIG. 24D is a graph of the normalized optical transmission signals of a SWEDA structure 2000 with a linear groove pattern plotted as a function of polarization angle, in accordance with an embodiment of the invention. In one case, the measured polarization extinction ratio for TE and TM incidence was 6100 so that that the amount of TE light transmission through the linear-groove based SWEDA structure 2000 is 6100 times higher than the TM case. Such a high extinction ratio positively indicates that the linear-groove based SWEDA structure 2000 can serve as a highly compact and highly efficient polarization sensor.

E. SWEDA Structure for Boosting Detection Sensitivity

Some embodiments of SWEDA structures 2000 can be designed with optimal design features to improve detection of signals, especially weak signals. In these embodiments, the design features are optimized to increase the amplitude of the direct transmission component. For example, the size of the darkfield aperture 2010 may be increased. In one exemplary embodiment, a SWEDA structure 2000 can be designed with optimal design features to both generate a darkfield under a uniform light field and boost the direct transmission signal under a non-uniform light field.

In one embodiment, a SWEDA structure 2000 having an optimized circular groove pattern was used to perform raster-scanning in a relay microscope. A uniform light field of intensity of about 0.2 W/cm² from a 738 nm laser was transmitted through each specimen. A 1:1 relay microscope was used to project a virtual image of the specimen onto the optimized circular-groove based SWEDA structure 2000. An example of a 1:1 relay microscope can be found in X. Cui, et al., "Quantitative differential interference contrast microscopy based on structured-aperture interference," Applied Physics Letters, vol. 93, p. 091113, 2008, which is hereby incorporated by reference in its entirety for all purposes. The specimen was raster scanned. The light transmission through the darkfield aperture 2010 was measured at each point of the scan. A darkfield image was generated by compiling the collected data. A similar image was taken with a standard microscope for comparison.

Figure 25:
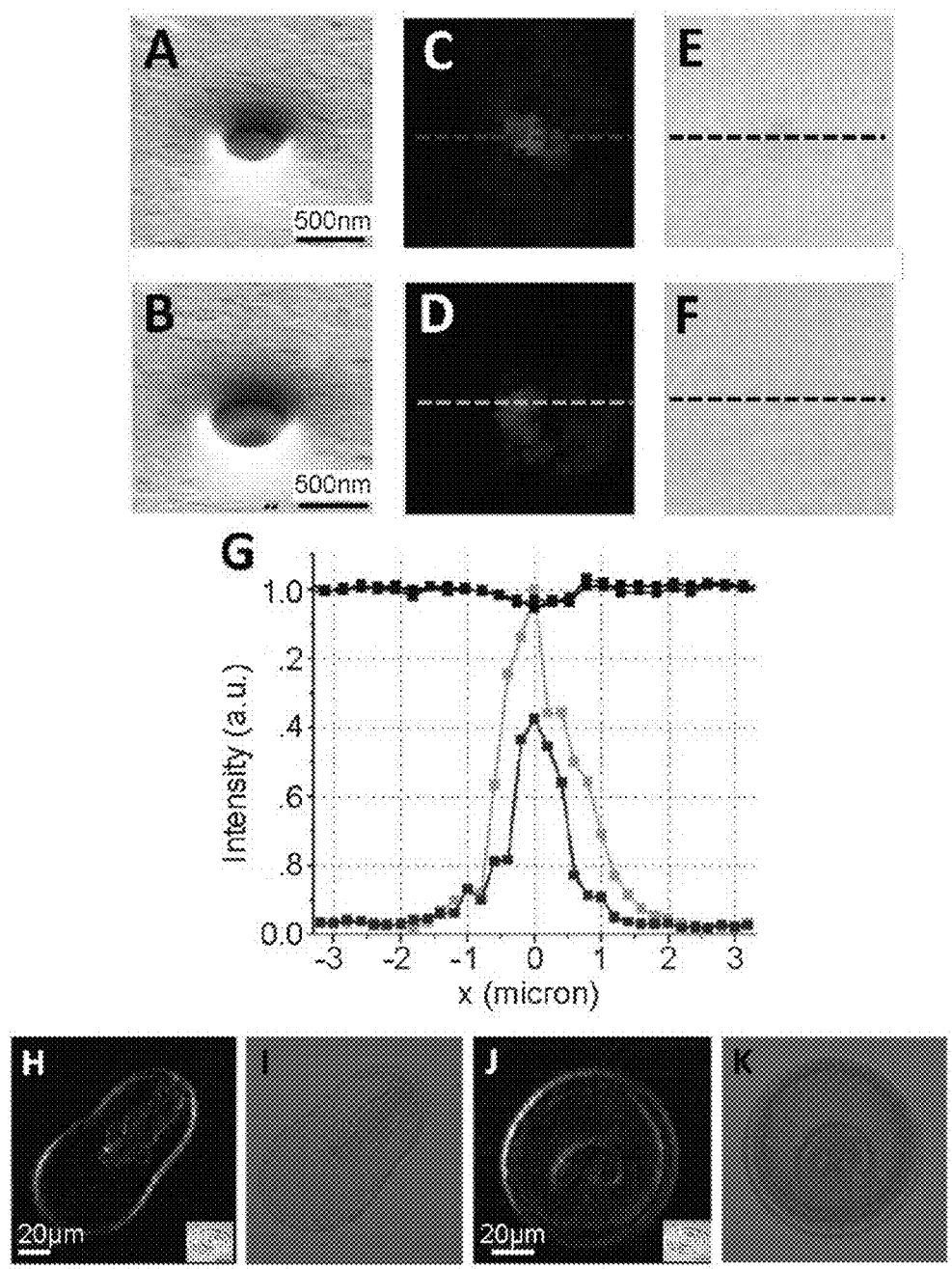
FIGS. 25A and 25B are scanning electron microscope images of the 175 and 250 nm pits respectively, in accordance with an embodiment of the invention.
FIGS. 25C and 25D are images taken of the 175 and 250 nm pits using a SWEDA-based raster-scanning device, in accordance with an embodiment of the invention.
FIGS. 25E and 25F are images of the 175 and 250 nm pit samples taken using a conventional camera with the same complementary metal-oxide-semiconductor (CMOS) chip under the same illumination condition as the SWEDA collected images in FIGS. 25C and 25D.
FIG. 25G is a graph of the signal traces of the intensity readings across a centerline of the two pits for the SWEDA-based device, according to an embodiment of the invention and the conventional camera.
FIGS. 25H and 25J are SWEDA-based raster-scanned images of starfish embryos, according to an embodiment of the invention.
FIGS. 25I and 25K are images of the starfish embryos taken by a conventional bright field microscope.

In one case, a specimen was prepared of ITO-coated glass slide that was marked with shallow pits of radius of 175 nm and 250 nm via the FIB. FIGS. 25A and 25B are scanning electron microscope images of the 175 and 250 nm pits respectively, in accordance with an embodiment of the invention. FIGS. 25C and 25D are images taken of the 175 and 250 nm pits using a SWEDA-based raster-scanning device, in accordance with an embodiment of the invention. FIGS. 25E and 25F are images of the 175 and 250 nm pit samples taken using a conventional camera with the same CMOS chip under the same illumination condition as the SWEDA collected images in FIGS. 25C and 25D.

FIG. 25G is a graph of the signal traces of the intensity readings across a centerline of the two pits for the SWEDA-based device of an embodiment of the invention and the conventional camera. The measured image contrast (signal/background) enhancement is approximately 25 dB for the 175 nm pit and approximately 27 db for the 250 nm pit. The data acquired for the SWEDA-based device was normalized on the same scale. The conventional camera data was normalized versus the average background signal. The background intensity associated with the SWEDA-based device data was low and the contributive signals from the pits were well discernible. In fact, the contributive signals were sufficiently well-resolved that allows them to be used to quantify their relative strengths for the two pits. In comparison, the high background intensity of the conventional camera images combined with the associated noise masked the scattering contributions from the pits.

FIGS. 25H and 25J) are SWEDA-based raster-scanned images of starfish embryos, according to an embodiment of the invention. FIGS. 25I and 25K are images of the starfish embryos taken by a conventional bright field microscope. The SWEDA-based device images shown in FIGS. 25H and 25J have a dark background. In addition, the edge and interior of the starfish embryos appeared brighter in the SWEDA images shown in FIGS. 25H and 25J and darker in the control image shown in FIGS. 25I and 25K. That is, the device employing the SWEDA structure 2000 generated an image with a dark background while producing an image where the edge and interior of the starfish embryo appears brighter, with higher contrast as opposed to the control image which is darker with less contrast. This is again consistent with a darkfield image as sample locations with substantial scattering will appear brighter in a darkfield image than a simple transmission microscope.

In some embodiments a circular-groove based SWEDA structure 2000 can be employed to perform darkfield microscopy imaging at the sensor level. As explained in sections above, the underlying principle of a microscope employing a SWEDA structure 2000 is different from that of a conventional darkfield microscope. Conventional darkfield microscopy depends on oblique illumination and a relatively small objective angle of collection to screen out the uniform background via a fairly sophisticated bulk optical arrangement. The ability of a circular-groove based SWEDA structure 2000 to screen out uniform background presents a more direct approach.

In many embodiments, SWEDA structures 2000 have features that are optimized for single wavelength operations. In other embodiments, a SWEDA structure 2000 can include a multibeam interference that can operate over a broad range of wavelengths. In these embodiments, the features of the SWEDA structure 2000 with the multibeam interference can be optimized to operate for a broad range of wavelengths.

In many embodiments, the SWEDA structures 2000 are designed with symmetric features to block out only uniform light at normal incidence. In other embodiments, the SWEDA structure may have asymmetric features such as a darkfield aperture and/or grooves with asymmetric structure that can screen out light at other incidence angles.

In some embodiments, SWEDA structures 2000 can be fabricated on top of a CCM or CMOS sensor pixels. The small size and substantially planar design of SWEDA structures 2000 of certain embodiments can make such implementation particularly suited for foundry fabrication.

In one embodiment, an array of SWEDA structures 2000 can replace an array of simple light transmissive regions in an OFM device—a low-cost, lensless and high resolution microscopy approach, to accomplish darkfield microscopy imaging on a chip. Examples of OFM devices can be found in X. Cui, et al., "Lensless high-resolution on-chip optofluidic microscopes for Caenorhabditis elegans and cell imaging," Proceedings of the National Academy of Sciences, vol. 105, p. 10670, 2008 and X. Heng, et al., "Optofluidic microscopy—method for implementing a high resolution optical microscope on a chip," Lab on a Chip, vol. 6, pp. 1274-1276, 2006, which are hereby incorporated by reference in their entirety for all purposes. The use of SWEDA structures 2000 in this embodiment is especially appropriate as both the OFM device and SWEDA structure implementation are well suited for semiconductor mass-fabrication. In fact, it is difficult to envision a more compact and cost-effective approach for incorporating darkfield ability than in an OFM system.

In some exemplary embodiments, a SWEDA structure 2000 exactly balances the surface-wave-induced component and direct light transmission component in a destructive interference manner. In one embodiment, the SWEDA structure 2000 acts effectively as a tiny interferometer (~6 microns or less) that can be fabricated on a single metal substrate and which has excellent stability. In many cases, SWEDA structures 2000 exhibit little to no significant performance drift over an entire operation. Further, since SWEDA structures are planar or substantially planar in many cases, they can be mass produced in a semiconductor foundry.

F. SWEDA-Based Implementations and Applications

SWEDA structures 2000 of embodiments can be implemented in various forms into SWEDA-based systems for various applications. For example, SWEDA-based systems of embodiments can include a SWEDA-based sensor that can effectively suppress the background prior to sensor detection and allow detection of weak signals in extremely compact architectures. These SWEDA-based systems can be advantageous for a broad range of applications from on-chip biosensing to metrology and microscopy. In an exemplary implementation, one or more SWEDA structures 2000 can be fabricated onto a sensor chip (e.g., CMOS sensor chip). The resulting on-chip device can be easily implemented by plugging it into an existing imaging device (e.g., standard microscope) to generate a darkfield microscope. In one case, the sensor chip can be patterned with a grid of tightly spaced circular groove based SWEDA structures 2000 that can be used as the microscope camera. The darkfield microscope can employ a laser as an illumination source 2040 in some cases.

In embodiments, the concept of the SWEDA structure 2000 can apply to optical isolation in an ultra-compact format, polarization control in semiconductor lasers, wavefront detection, extending depth of field of the type II aperture based imaging device, and perspective imaging by customizing the optical transfer function on the pixel level. An example of a semiconductor laser can be found in N. Yu, et al., "*Semiconductor lasers with integrated plasmonic polarizers,*" Applied Physics Letters, vol. 94, p. 151101, 2009, which is hereby incorporated by reference in its entirety for all purposes. An example of a type II aperture based imaging device can be found in X. Heng, et al., "*Characterization of light collection through a subwavelength aperture from a point source,*" Optics express, vol. 14, pp. 10410-10425, 2006, which is hereby incorporated by reference in its entirety for all purposes. An example of perspective imaging can be found in R. Ng, et al., "*Light field photography with a handheld plenoptic camera,*" Computer Science Technical Report CSTR, vol. 2, 2005, which is hereby incorporated by reference in its entirety for all purposes.

1. SWEDA-Based System

Figure 26:
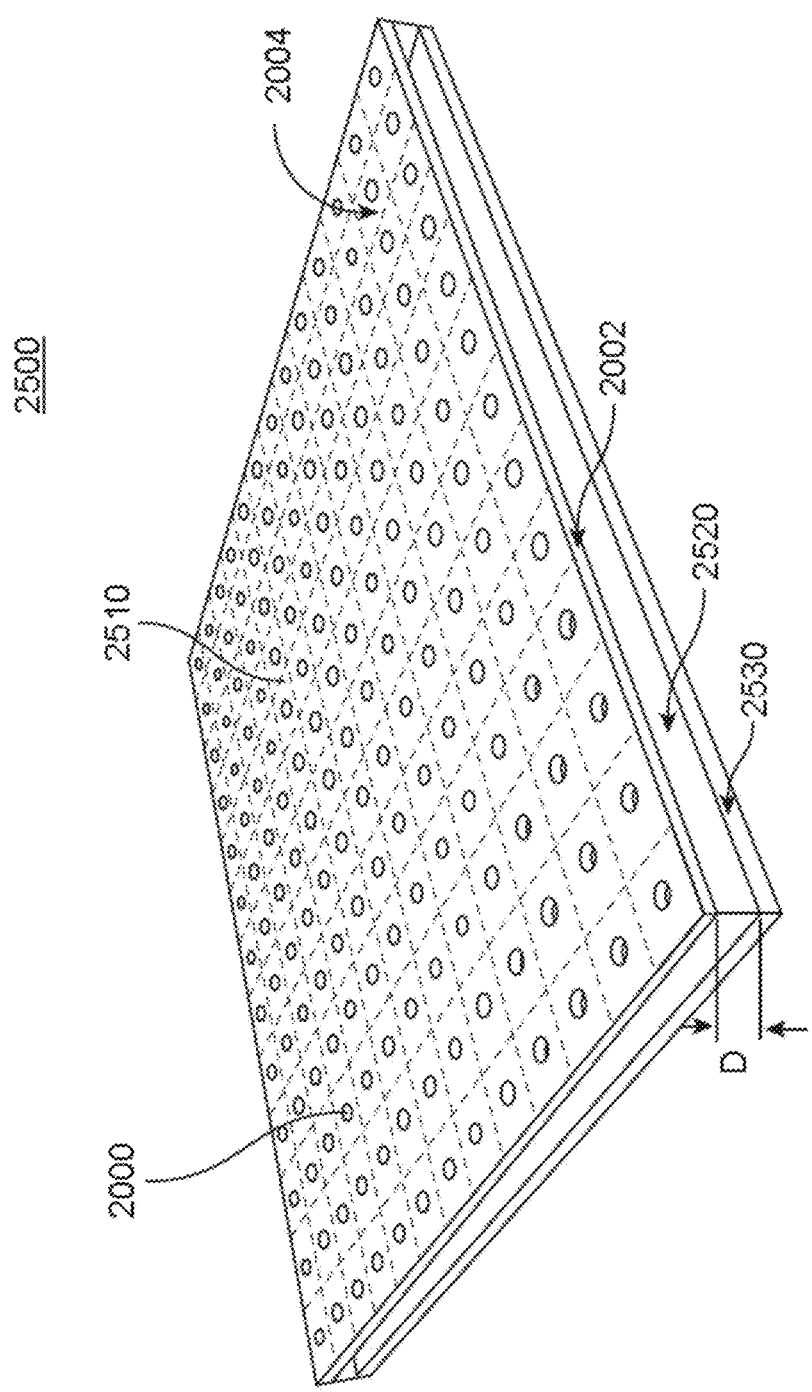
FIG. 26 is a schematic drawing of a SWEDA-based system having a SWEDA-based sensor, according to an embodiment of the invention.

FIG. 26 is a schematic drawing of a SWEDA-based system 2500 having a SWEDA-based sensor 2510, according to an embodiment of the invention. The SWEDA-based sensor 2510 comprises an aperture layer 2002, a light detector layer 2530, and an optional transparent layer 2520 between the aperture layer 2002 and the light detector layer 2530. Other embodiments of the SWEDA-based sensor 2510 do not have the transparent layer 2520.

The aperture layer 2002 is located at a distance D away from the light detector layer 2530. The optional transparent layer 2520 between the light detector layer 2530 and the aperture layer 2002 can include one or more layers of transparent material such as water or a viscous polymer (e.g., SU-8 resin), or can be a vacuum or gas-filled space. In embodiments without the transparent layer 2520, the aperture layer 2002 may be located directly on the light detector layer 2530.

The aperture layer 2002 includes a first surface 2004 and a second surface 2006 (not shown). The aperture layer 2002 also includes one or more SWEDA structures 2000 arranged in a two dimensional array in the first surface 2004. Other dimensions can be used. Also, the SWEDA structures 2000 may be located in the second surface 2006 or in both first and second surfaces 2004 and 2006 in other embodiments. In the illustrated example, the aperture layer 2002 is made of silver and has a thickness of 350 nm. In other cases, the aperture layer 2002 can be made of gold plated glass plate or other suitable material with suitable thickness. Although a two-dimensional array is shown in this embodiment, any suitable arrangement of SWEDA structures 2000 can be used in other embodiments of a SWEDA system 2500. Some examples of suitable arrangements include a one-dimensional array, multiple one-dimensional arrays, a set of circular rings of SWEDA structures 2000, etc. In addition, any suitable number of SWEDA structures 2000 can be used in the SWEDA system 2050. Further, any suitable spacing between SWEDA structures 2000 can be used.

The light detector layer 2530 includes any suitable light detector (e.g., photosensor such as a CMOS image sensor) capable of measuring the distribution of light received through the darkfield apertures 2010 in the SWEDA structures 2000 and capable of generating signals with wavefront data about the intensity, wavelength, wavefront slope, phase gradient in one or more orthogonal directions, and/or other information about the light being detected. The signals may be in the form of electrical current that results from the photoelectric effect. Some examples of suitable devices include a charge coupled device (CCD) or a linear or two-dimensional array of photodiodes (e.g., avalanche photodiodes (APDs)). A suitable light detector could also be a CMOS or photomultiplier tubes (PMTs). Other suitable light detectors are commercially available.

The light detector layer 2530 comprises one or more light detecting elements 2532. The light detecting elements 2532 can be of any suitable size (e.g., 1-4 microns) and any suitable shape (e.g., circular or square). The light detecting elements 2530 can be arranged in any suitable form such as a one-dimensional array, a two-dimensional array, and a multiplicity of one-dimensional and/or two-dimensional arrays. The arrays can have any suitable orientation or combination of orientations. In some cases, the light detecting elements 2530 can be arranged in the same form as the darkfield apertures 2010 and correspond to the darkfield apertures 2010.

In one embodiment, sensor chips with SWEDA-based sensors 2510 having broad-bandwidth SWEDA structures 2000 can be used in place of the standard camera sensor to accomplish sensor level darkfield imaging. Such sensor chips, in combination with a coherent light source, can transform a standard microscope into a darkfield microscope that is simpler and less expensive than current darkfield microscopes. Such sensor chips can also be used to enable edge-detection imaging in machine vision applications if the illumination source employed is coherent.

In embodiments, a SWEDA-based system 2500 can be a tuned or calibrated. In some cases, the illumination from the illumination source of a SWEDA-based system 2500 can be a modified to have a direct transmission component with the same amplitude and phase of a surface wave(s) induced by one or more SWEDA structures 2000 in the SWEDA-based system 2500. In these cases, the phase and amplitude of the direct transmission component may match the phase and amplitude of the surface wave component. In one case, the incident angle of the illumination of the illumination source 2040 is tuned to have the amplitude and phase that is similar to the surface wave induced by the existing SWEDA structure 2000. For example, the incident angle can be modified in small increments until a predetermined or measurable improvement is made in the darkfield. In some cases, this technique can be used to fine tune a SWEDA-based device 2500 with already fabricated SWEDA structures 2000. In one exemplary embodiment, this technique can be used to calibrate a SWEDA-based device 2500. This technique can be used alone or in combination with the method of modifying the design features of the SWEDA structure 2000 to induce a surface wave which is equal to the direct transmission of an illumination source.

2. Fabricating SWEDA Structures, SWEDA-Based Sensor, and Other Surface Wave Assisted Structures SWEDA structures 2000, SWEDA-based sensors 2510 having SWEDA structures 2000, and other surface wave assisted structures and sensors of embodiments can be fabricated in any suitable manner. An exemplary method of fabricating a SWEDA-based sensor 2510 having a single SWEDA structure 2000 according to an embodiment can be described with reference to FIGS. 27A-27D. This method can also be used to fabricate other surface wave assisted structures and associated pixels of embodiments. In these figures, the darkfield aperture 2010 is a hole. Any suitable combination of well know processes including etching, lamination, and photo lithography can be used to fabricate the SWEDA structures 2000 and SWEDA-based sensors 2510, and other surface wave assisted structures and sensors of embodiments.

In some cases, the aperture layer 2002 may consist of a metal layer and a transparent plate (e.g., a glass plate). In these cases, the metal layer can be evaporated onto the transparent surface of the transparent plate in some embodiments. Alternatively, the aperture layer 2002 can be of any other suitable opaque or semi-opaque layer.

Figure 27A:
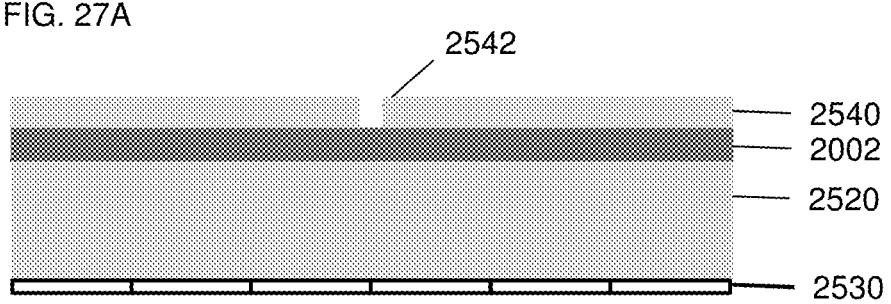
FIGS. 27A, 27B, 27C, and 27D illustrate a process of fabricating a SWEDA-based sensor, according to an embodiment of the invention.

As shown in FIG. 27A, a first photo resist layer 2540 having a hole 2542 is placed on the aperture layer 2002 (e.g. a gold layer), according to an embodiment of the invention. A transparent layer 2520 is attached to the aperture layer 2000. Also, a light detector 2530 including discrete light detecting elements is attached to the transparent layer 2530.

An etching process or other suitable process is used to form a darkfield aperture 2010 in the aperture layer 2002. Any suitable process such as standard electron beam lithography can be used to generate the hole in the first photo resist layer 2540. In other embodiments, etching need not be used. For example, laser ablation can be used to form darkfield aperture 2010 in the aperture layer 2002.

Figure 27B:
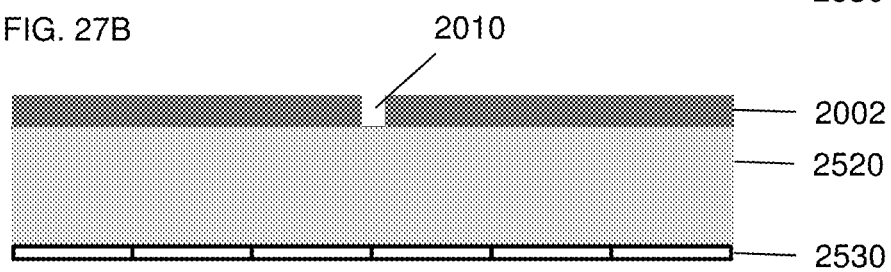
Figure 27C:
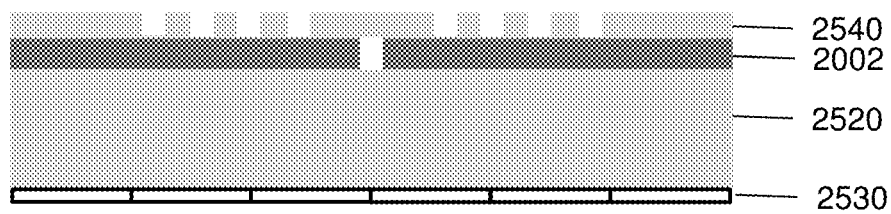

In FIG. 27B, the photo resist layer 2540 is removed. In FIG. 27C, a new second photo resist layer 2550 is deposited on the aperture layer 2002. Any suitable type of transparent or semi-transparent material can be used in the first and second photo resist layers 2540 and 2550. The second photo resist layer 2550 includes channels through the layer that are in the shape of the desired grooves 2020 of the SWEDA structure 2000.

Figure 27D:
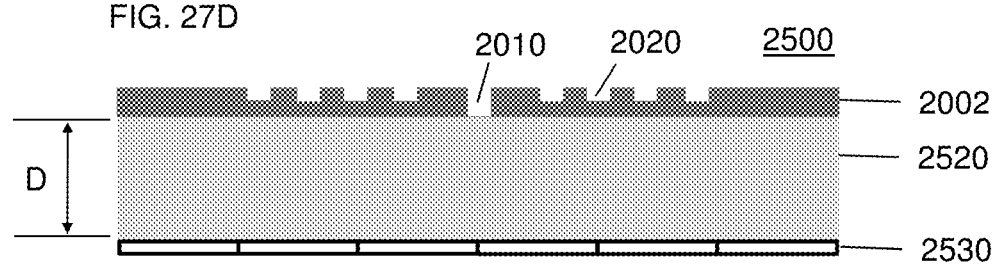

An etching process can be used to form the grooves 2020 in the aperture layer 2002. In FIG. 27D, the second photo resist layer 2550 is removed, forming the SWEDA-based sensor 2500, according to an embodiment of the invention. The SWEDA-based sensor 2500 comprises the SWEDA structure 2000, the light detector 2530 and the transparent layer 2520 between the light detector 2530 and the aperture layer 2002.

In one embodiment, a sacrificial layer (e.g., a 100 nm thick silicon nitride layer) can coat the aperture layer 2002. The first and second photo resist layers 2540 and 2550 can be deposited onto of this sacrificial layer. After the darkfield aperture 2010 and the grooves 2020 are created, the sacrificial layer can be removed. By employing the sacrificial layer, the SWEDA structure 2000 may have sharper features. In some cases, the SWEDA structure 2000 of this embodiment can provide better system characteristics such as a higher darkfield suppression factor.

3. SWEDA-Based Pixel Level Applications for High Sensitive On-Chip Chemical or Bio Detection Systems Miniaturization and integration are two key features of current device engineering. The use of CMOS integrated circuits (CMOS IC) in biological and biomedical applications is a good example of this engineering trend. A variety of CMOS IC based analytical instruments have been developed in the past years, such as the optofluidic microscope, the magnetic cell manipulation system, microarray platform for DNA and protein analysis and diagnostics, and microelectrode arrays for monitoring cell activity. Compared with the clinical bulky, high power consumption platform, the sensor chip based instruments meet the growing need for the handheld, miniaturized, and highly automated devices for the biological testing at the point-of-care. Among the various applications of the CMOS IC instruments, one major category is the on-chip sensing and imaging system-based on a CMOS image sensor. Coupled to a microfluidic platform for sample delivery and confinement, CMOS image sensors or other image sensors offer the promise of achieving higher speed, lower power consumption, and higher level integration in a portable lab on-chip format than conventional systems. However, the detection of a weak optical signal using an image sensor can be easily confronted by an overwhelming background. One familiar example is the completely invisibility of the stars during the day time due to the overwhelming brightness of the sun. Although such a high background can be subtracted by a postprocessing algorithm, the noise of the background cannot be subtracted due to its statistic nature. The case becomes even worse if the signal is weaker than the noise fluctuation of the background, and as such, it put a critical limit on various image sensor based on-chip detection devices.

To deal with this issue, embodiments use a surface wave enabled pre-detection background suppression scheme that can be used to increase the SNR during the detection of a weak optical signal. In these embodiments, an outer layer of the image sensor (e.g., CMOS image sensor), an aperture layer covering the image sensor, or a transparent layer over the aperture layer can be patterned with grooves around an aperture designed to provide pre-detection background suppression.

Figure 28A:
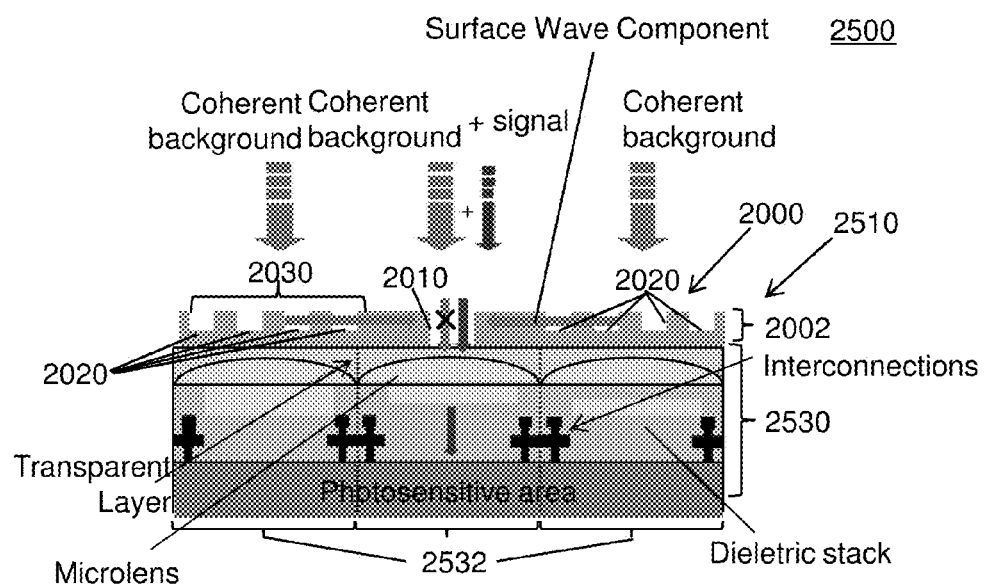
FIG. 28A is a schematic drawing of a cross sectional view of a portion of the SWEDA-based system that employs pre-detection background suppression, according to an embodiment of the invention.
Figure 28B:
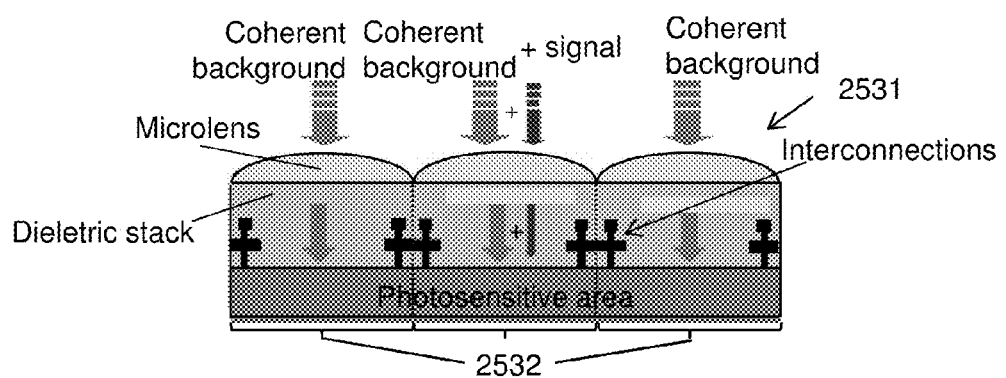
FIG. 28B is a schematic drawing of a cross sectional view of a portion of an unpatterned single image pixel of an imaging sensor (e.g., CMOS imaging sensor) having light detecting elements.
Figure 28C:
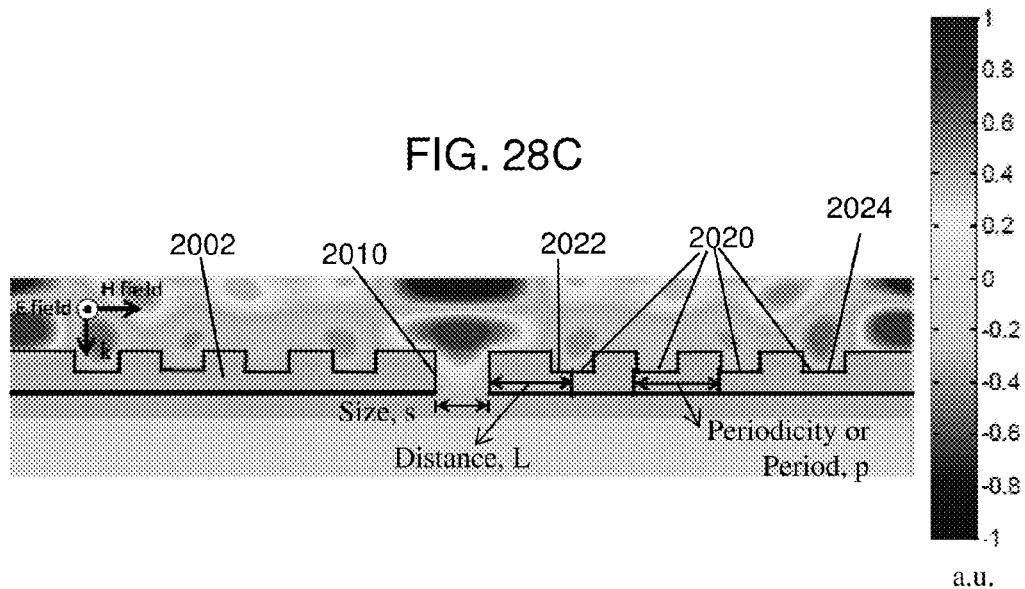
FIG. 28C is a simulation of the electric field distribution at the SWEDA structure of FIG. 28A, according to an embodiment of the invention.

FIGS. 28A-28C illustrate an example of an embodiment of a SWEDA-based system 2500 that uses a pre-detection background suppression scheme. FIG. 28A is a schematic drawing of a cross sectional view of a portion of the SWEDA-based system 2500 that employs pre-detection background suppression, according to an embodiment of the invention. The SWEDA-based system 2500 includes a single pixel of a SWEDA-based sensor 2510. The pixel comprises a SWEDA structure 2000 having an aperture layer 2002. The aperture layer 2002 is patterned with grooves 2020 around a darkfield aperture 2010. The SWEDA-based sensor 2510 also comprises a light detector layer 2530 having light detecting elements 2532 (e.g., image sensor pixels) for receiving light through the darkfield aperture 2010. In some cases, the aperture layer 2002 may be an outer patterned layer of an image sensor. The light detector layer 2530 is a multi-layered structure comprising a transparent layer (e.g., a Polymethyl methacrylate (PMMA) layer), a dielectric stack layer having interconnections, and a photosensitive layer (e.g., silicon substrate layer). The transparent layer optionally includes microlenses. The interconnections can refer to structures or devices for connecting the dielectric stack layers at adjacent light detecting elements 2532. A dielectric stack layer can refer to one or more layers of dielectric material and optionally layers of other material(s). The light detector layer 2530 may omit layers or include other layers in other embodiments.

FIG. 28A illustrates the incoming coherent background component, the signal component, and the surface wave enable component along the surface of the aperture layer 2002. The signal component may be induced by an object located proximal the darkfield aperture 2010. In this example, the surface wave enabled component cancels out the coherent background component at the aperture 2010 above the light detector layer 2530 to provide pre-detection background suppression of the coherent background component and the light detector layer 2530 receives only the signal component.

As a comparison, FIG. 28B is a schematic drawing of a cross sectional view of a portion of an unpatterned single image pixel of an imaging sensor 2531 (e.g., CMOS imaging sensor) having light detecting elements 2532. The imaging sensor 2531 is a multi-layered structure comprising a layer including microlenses, a dielectric stack layer having interconnections, and a photosensitive layer (e.g., silicon substrate layer). The imaging sensor 25310 may omit layers or include other layers in other embodiments. For example, one embodiment may omit the microlenses. In FIG. 28B, the image sensor 2531 receives both the incoming coherent component and the signal component.

Figure 28D:
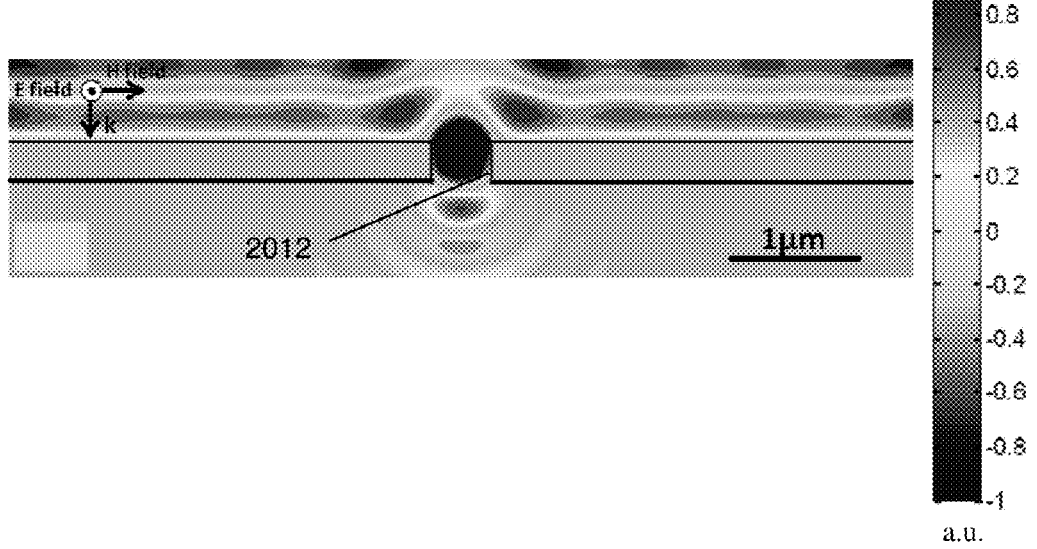
FIG. 28D is a simulation of an electric field distribution at a single hole.

FIG. 28C is a simulation of the electric field distribution at the SWEDA structure 2000 of FIG. 28A, according to an embodiment of the invention. FIG. 28C illustrates that the incidence of the coherent background on the SWEDA structure 2000 results in zero transmission. FIG. 28C also includes some of the design features of the SWEDA structure 2000. The SWEDA structure 2000 includes an aperture layer 2002 patterned with grooves around a darkfield aperture 2010. The darkfield aperture 2010 has a darkfield aperture size ("s"). The grooves 2020 include an innermost groove 2022 and an outermost groove 2024. In this example, the grooves 2020 have a constant groove periodicity ("p") between adjacent grooves 2020. The SWEDA structure 2000 also has a distance ("L") between the centerline of the innermost groove 2022 and the outer edge of the darkfield aperture 2010. For comparison, FIG. 28D is a simulation of the electric field distribution around an unpatterned aperture layer of FIG. 28B. In both FIGS. 28C and 28D, there is no object inducing a signal component. In FIG. 28D shows the incidence of the coherent background on a single hole induces significant transmission.

FIGS. 29A, 29B, and 29C show an on-chip implementation of a surface wave enabled pre-detection background suppression scheme, according to an embodiment of the invention. FIG. 29A is an image of a CMOS pixel. FIG. 29B is a focus ion image of more than a pixel of a SWEDA-based sensor 3510 employing the surface wave enabled pre-detection background suppression scheme. The pixel includes a SWEDA structure 2000 with a plurality of grooves 2030 including four circular grooves 2020. The grooves 2020 are centered around a darkfield aperture 2010. The SWEDA structure 2000 of the pixel covers a 3×3 grid of light detecting elements 2532 for receiving and measuring light through the darkfield aperture 2010. In this example, the pixel size is about 5 μm*5 μm.

FIG. 29C is a set of images of the measured optical transmission through the darkfield aperture 2010 of the pixel in FIG. 28B and through a reference simple single hole for coherent background of wavelengths: λ=760 nm, λ=775 nm and λ=790 nm. For the coherent background of 775 nm, the transmission through the darkfield aperture 2010 is close to zero. The measured suppression ratio is about 1100 where the suppression ratio is the ratio of transmission of simple single hole/transmission of the SWEDA structure 2000. Based on the high suppression ratio of embodiments, the SWEDA-based sensor 2510 may be able to provide an improved platform than the conventional CMOS based detection devices for on-chip weak signal detection. The SWEDA-based sensor 2510 using this surface wave enabled pre-detection background suppression scheme combines the high sensitivity of surface wave sensing and the feasibility of image sensor (e.g., CMOS image sensor).

Since the pixel size can be about 5 μm*5 μm for the pixel shown in FIG. 28B, the packing density of the SWEDA-based sensor 2510 can be as high as $10^6$ sensing elements per centimeter square for this embodiment. An example a SWEDA-based sensor 2510 with this packing density is shown in FIG. 26. A SWEDA-based system 2500 having this SWEDA-based sensor 2510 with this density and employing this scheme may be able to provide a new class of non-expensive, hand-held, high throughput, real time, label free sensing systems.

Figure 30:
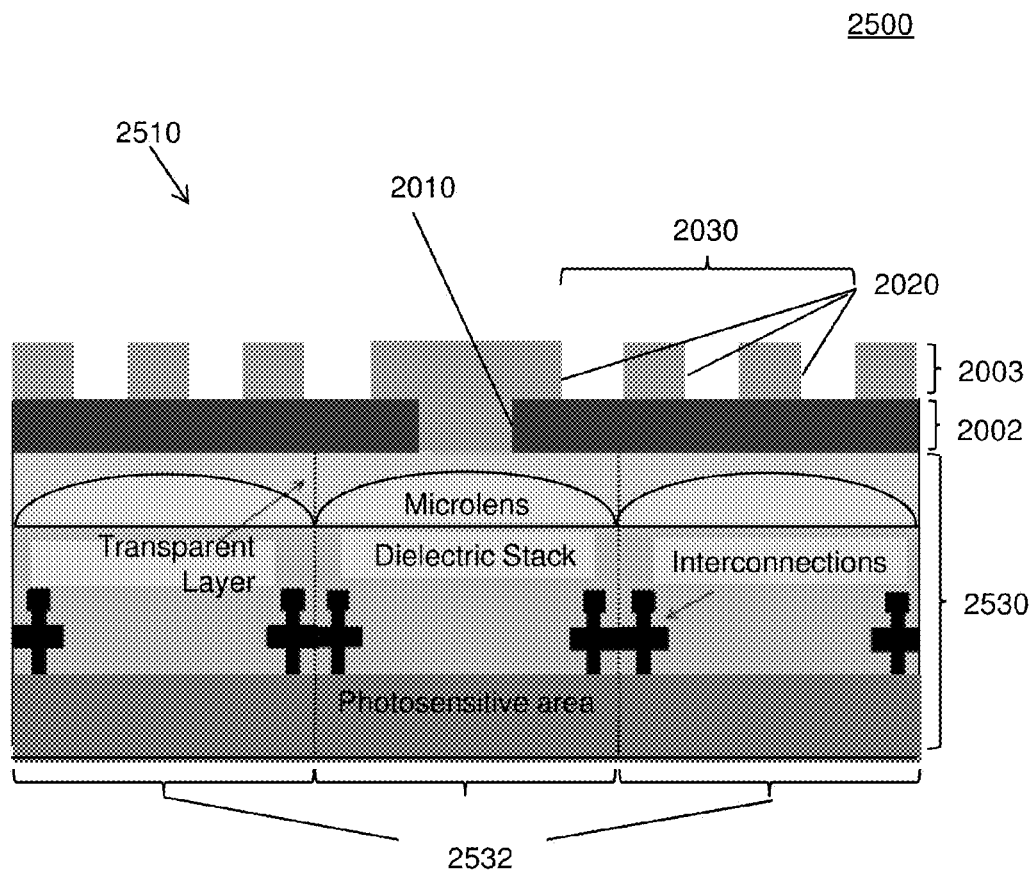
FIG. 30 is a schematic drawing of a cross sectional view of a portion of another example of a SWEDA-based system having a SWEDA-based sensor that employs the pre-detection background suppression scheme, according to an embodiment of the invention.

FIG. 30 is a schematic drawing of a cross sectional view of a portion of another example of a SWEDA-based system 2500 having a SWEDA-based sensor 2510 that employs the pre-detection background suppression scheme, according to an embodiment of the invention. The illustrated example in FIG. 30 includes a single pixel of the SWEDA-based sensor 2510. The pixel has a transparent layer 2003 with the plurality of grooves 2030, an aperture layer 2002 having a darkfield aperture 2010, and a light detector layer 2530. The aperture layer 2002 lies between the transparent layer 2003 and the light detector layer 2530. The light detector layer 2530 includes light detecting elements 2532 (e.g., image sensor pixels) for receiving and measuring light through the darkfield aperture 2010. The SWEDA-based system 2500 of FIG. 30 is a modification of the system shown in FIG. 29A. In FIG. 30, the grooves 2020 are not defined in the aperture layer 2002 as they are in FIG. 29A. Instead, the grooves 2020 in FIG. 30 are in a transparent photoresist layer 2003 outside the aperture layer 2002. This modification may greatly simplify the fabrication process and achieve a better control of the depth of the groove structure than the fabrication of the system shown in FIG. 29A.

A transparent layer 2003 can refer to a layer of one or more suitable transparent materials (e.g., a photoresist material). The transparent layer 2003 has first and second outer surfaces. The transparent layer 2003 may include one or more grooves 2020 defined in the first outer surface, in the second outer surface, in both first and second outer surfaces, or through the transparent layer 2003. The grooves 2020 may be located around an aperture in a separate aperture layer 2002 in some cases. The transparent layer 2003 has dimensions (e.g., thickness, length, width). The thickness of the aperture layer 2002 can be any suitable thickness such as, for example, 30, 20 or 10 microns. In some cases, the type of material used in the transparent layer 2003 can affect roughness of the aperture layer 2002 and the sharpness of the features in the transparent layer 2003, which can affect the surface waves induced by any grooves in the surface.

4. Broadband SWEDA

Figure 31A:
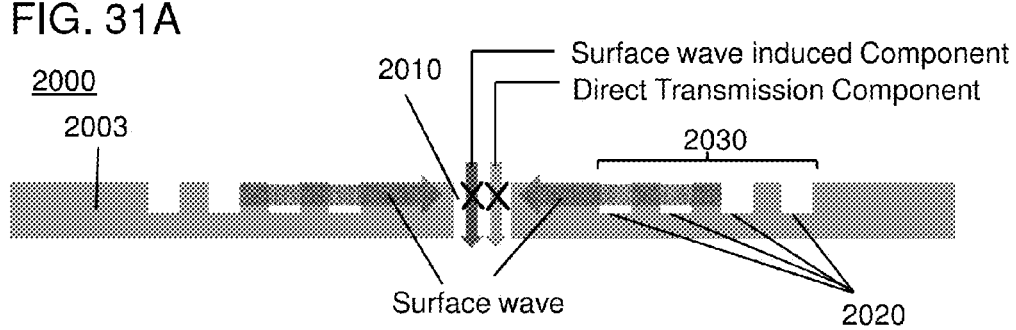
FIG. 31A is a schematic drawing of a cross sectional view of a SWEDA structure that uses the two-beam interference scheme, according to an embodiment of the invention.

The SWEDA structures 2000 of embodiments employ a two-beam interference scheme. Under this scheme, a plurality of grooves 2030 is designed to induce a surface wave component that destructively interferes with a single coherent background component. FIG. 31A is a schematic drawing of a cross sectional view of a SWEDA structure 2000 that uses the two-beam interference scheme, according to an embodiment of the invention. The SWEDA structure 2000 includes an aperture layer 2002 with a single set (plurality) of circular grooves 2030 around a darkfield aperture 2010. In the illustrated example, the groove period, p, (i.e., distance between grooves 2010) of the set of grooves 2030 is a constant value. That is, the distance between adjacent grooves 2010 in the plurality of grooves 2030 is constant. FIG. 31A also shows a direct transmission component (e.g., background component) and a surface wave induced component induced by the grooves 2030. In this example, the surface wave induced component and cancels out the direct transmission component.

Figure 31B:
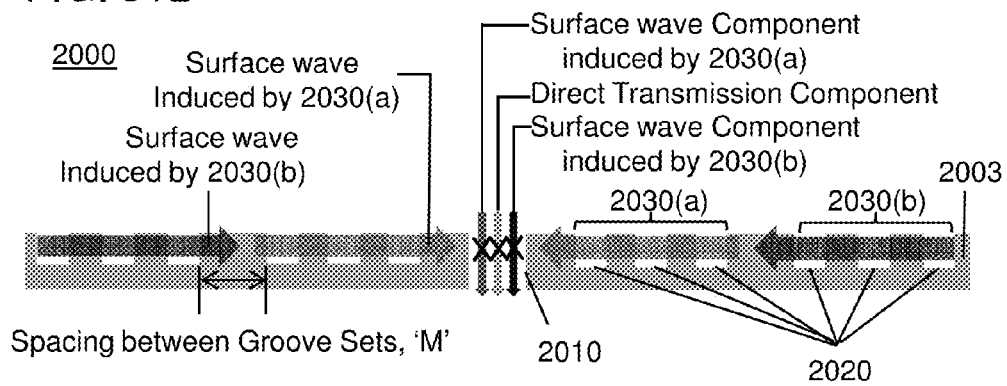
FIG. 31B is a schematic drawing of a cross sectional view of a broadband SWEDA structure, according to an embodiment of the invention.

FIG. 31B is a schematic drawing of a cross sectional view of a broadband SWEDA structure 2000, according to an embodiment of the invention. A broadband SWEDA structure refers to a SWEDA structure that can induce multiple surface waves components that can cancel incoming background light of a broader range of wavelengths. The broadband SWEDA structure 2000 of FIG. 31B has a broader destructive interference bandwidth than the example shown in FIG. 31A. FIG. 31B illustrates a more sophisticated design of the SWEDA structure 2000 than the example shown in FIG. 31A. The aim of the design in FIG. 31B is to broaden the destructive interference bandwidth for the SWEDA structure 2000.

The design in FIG. 31B still includes only a single groove periodicity to not increase the parameter space to much. However, the SWEDA structure 2000 includes an aperture layer 2002 with two sets of circular grooves 2030(a) and 2030(b) around a darkfield aperture 2010 and an additional spacing, M, between the two sets of circular grooves 2030(a) and 2030(b). Any number (2, 3, 4, etc.) of sets of grooves 2030 can be used in other embodiments. FIG. 31B also shows a direct transmission component and two surface wave induced components induced by the two sets of circular grooves 2030(a) and 2030(a). In this example, two surface wave induced components of different wavelength bands cancel out the direct transmission component.

Figure 31C:
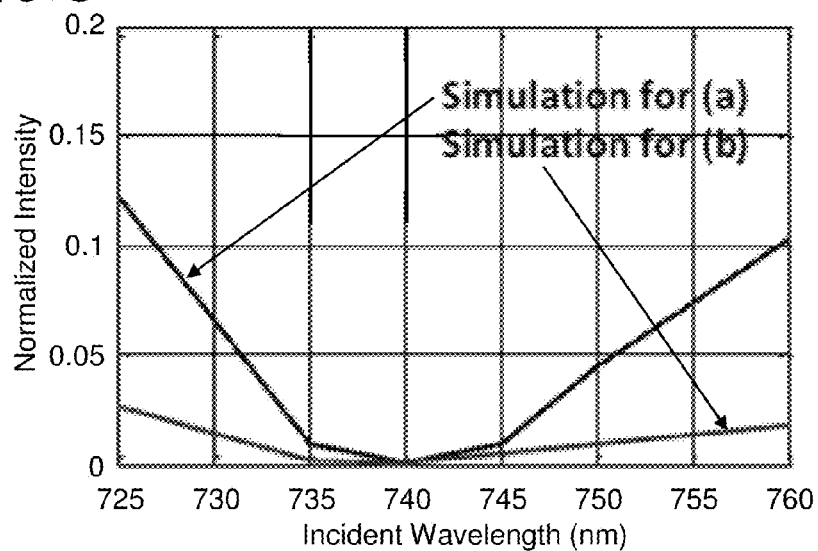
FIG. 31C is a graph of the simulation of the spectrum response of the SWEDA structures shown in FIGS. 31A and 31B, according to an embodiment of the invention.

FIG. 31C is a graph of the simulation of the spectrum response of the SWEDA structures 2000 shown in FIGS. 31A and 31B, according to an embodiment of the invention. The graph shows that the simulation ("Simulation for (a)") of the design in FIG. 31A has an almost zero normalized intensity of transmission for incident light of wavelength, λ of 740 nm and about 0.02 normalized intensity of transmission for incident light of wavelengths of 735 nm and 745. The simulation shows the normalized intensity of transmission of incident light increasing rapidly for wavelengths outside the narrow bandwidth between 735-745 nm. The graph also shows that the simulation ("Simulation for (b)") of the broadband design in FIG. 31B. These simulated results show a low normalized intensity for a much broader range of wavelengths. These simulations show that the broadband SWEDA structure 3000 design in FIG. 31B may have a better spectrum performance than the design in FIG. 31A.

In addition to using multiple sets of grooves 2030 and modifying the spacing, M, between the sets of grooves, other design parameters may be modified to increase the bandwidth of the SWEDA structure 2000. For example, the period, p, can be modified to have a non-constant value such as a gradually increasing/decreasing period. As another example, the size (e.g., width and/or depth) of the grooves 2010 can be modified.

Figure 32A:
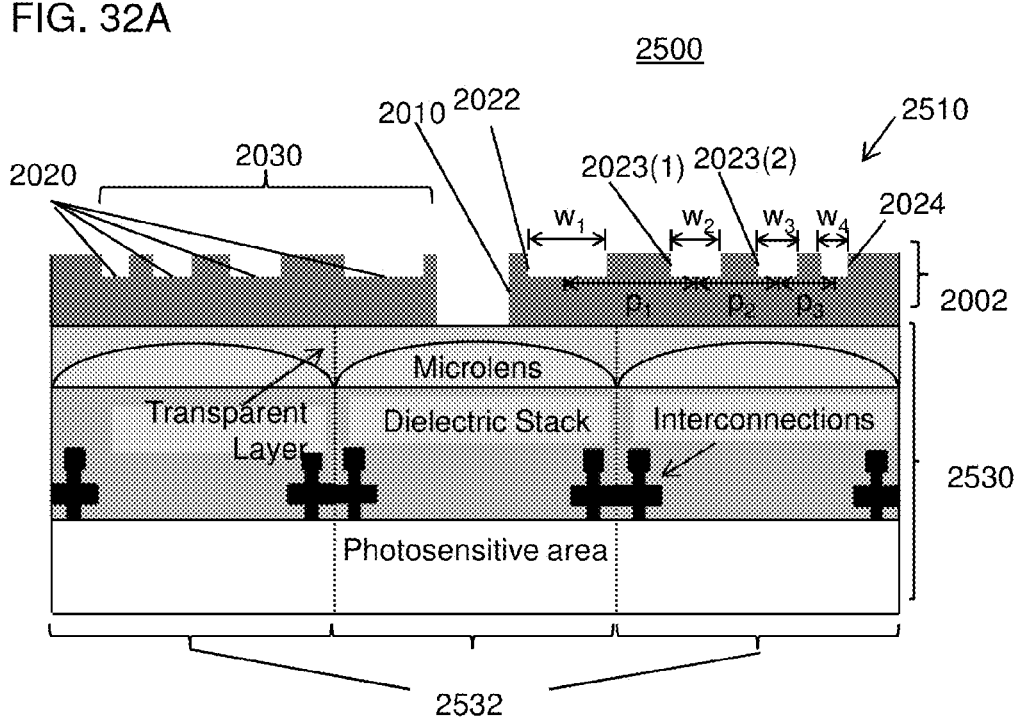
FIG. 32A is a schematic drawing of a cross-sectional view of a SWEDA system including a single pixel of a SWEDA-based sensor having a broadband SWEDA structure with a gradually changing groove structure, according to an embodiment of the invention.

FIG. 32A is a schematic drawing of a cross-sectional view of a SWEDA system 2500 including a single pixel of a SWEDA-based sensor 2510 having a broadband SWEDA structure 2000 with a gradually changing groove structure 2030, according to an embodiment of the invention. The pixel includes an aperture layer 2002 with a darkfield aperture 2010 and a light detector layer 2530 having light detecting elements 2532. The aperture layer 2002 includes the gradually changing groove structure 2030 with grooves 2020 having gradually changing periods, p, and gradually changing widths, w. The gradually changing groove structure 2030 includes an innermost groove 2022, an outermost groove 2024, and two inner grooves 2023(1) and 2023(2). The periods, $p_1$, $p_2$, and $p_3$, between adjacent grooves 2020 in the gradually changing groove structure 2030 are gradually decreasing from the innermost groove 2022 to the outermost groove 2024. The associated widths, $w_1$, $w_2$, $w_3$, and $w_4$ of the grooves 2020 are also decreasing from the innermost groove 2022 to the outermost groove 2024. As such, there are multiple surface wave components that can be induced by the gradually changing groove structure 2030. Adjacent grooves 2020 with different periods may induce different surface wave components. Each of the induced surface wave components corresponds to a specific wavelength.

Figure 32B:
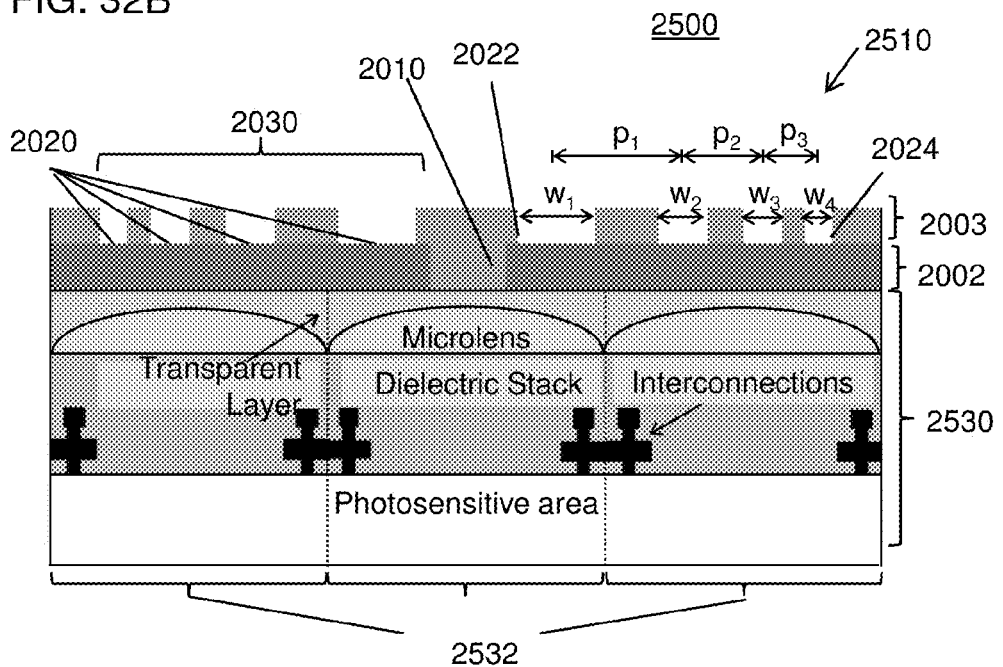
FIG. 32B is a schematic drawing of a cross-sectional view of a SWEDA system including a single pixel of a SWEDA-based sensor having a broadband SWEDA structure with a gradually changing groove structure, according to an embodiment of the invention.

FIG. 32B is a schematic drawing of a cross-sectional view of a SWEDA system 2500 including a single pixel of a SWEDA-based sensor 2510 having a broadband SWEDA structure 2000 with a gradually changing groove structure 2030, according to an embodiment of the invention. The SWEDA-based sensor 2510 includes an aperture layer 2002 with a darkfield aperture 2010 and a light detector layer 2530 having light detecting elements 2532. In this example, the pixel includes an additional layer 2003 of transparent photoresist, an aperture layer 2002 having a darkfield aperture 2010, and a light detector layer 2530 and an aperture layer 2002 between the light detector layer 2530 and the transparent layer 2003. In this pixel, the additional transparent layer 2003 defines the gradually changing groove structure 2030. This pixel is a modification of the system shown in FIG. 32A. In FIG. 32B, the grooves 2020 are not defined in the aperture layer 2002 as they are in FIG. 32A. Instead, the grooves 2020 in FIG. 32B are defined in a transparent photoresist layer 2003 outside the aperture layer 2002. Such a modified scheme may provide additional freedom to precisely control the dimensions (e.g., depth and width) of the grooves and may greatly simplify the fabrication process.

5. SWEDA-Based Polarization Sensor

Some remarkable properties of surface waves (e.g., Plasmon surface waves) have been a subject of intensive study in past years. For example, the extraordinary optical transmission of a two-dimensional subwavelength hole array, the beaming effect of a single hole surrounded by a circular groove, the plasmonic sorter, the plasmonic wave plate, etc. Such remarkable properties of surface waves may possibly bridge the gaps between photonics, biochemical sensing and CMOS based electronics technologies. Recently, several papers (e.g., "*Theory of optical transmission through elliptical nanohole arrays*," Phys. Rev. B 76, 085409 (2007)) have addressed the polarization issue of the surface Plasmon wave based light transmission. It has been shown that elliptical or rectangular apertures can behave like polarizers, following the Malus law of absorption. However, polarization selective ratios of conventional structures are normally less than 50. The polarization-selective ratio of such reported conventional apertures is determined by the difference of the coupling efficiency of the two orthogonal polarizations. Normally, one of the polarizations induces local surface waves and enhances the transmission, while the orthogonal polarization state cannot. The enhancement factor of one polarization state in such conventional structures put a theoretical limit on the polarization selective ratio.

Referring back to FIG. 24A, the SWEDA structure 2000 of the illustrated example is part of a pixel of the SWEDA-based polarization sensor 2512. The SWEDA-based polarization sensor 2512 includes the SWEDA structure 2000 having a central aperture 2010 and a first and second plurality of linear grooves 2030. Each linear groove is oriented in the same direction and has the same dimensions (length, depth, width, etc.). Each plurality of linear grooves 2030 is located at the same distance to either side of the central aperture 2010. Both first and second pluralities of linear grooves 2030 have the same constant periodicity, p. Although the illustrated examples shows each plurality of periodical grooves 2030 having four linear grooves 2010, any suitable number of grooves 2010 can be used. In addition, the linear grooves 2010 of embodiments may vary in dimension. The SWEDA structure 2000 lies over a light detector layer 2530 (not shown). In the illustrated example, the four linear grooves 2010 include an innermost groove 2022 and an outermost groove 2024. The SWEDA structure 2000 includes a distance, 'L,' between the central hole 2010 and the innermost groove 2022. The SWEDA-based polarization sensor 2512 shown in FIG. 24A may accomplish ultrahigh polarization selectivity (sensitivity) in a robust, compact and simple format.

In the SWEDA-based polarization sensor 2512 shown in FIG. 24A, incoming transverse magnetic (TM) polarized light (electric-field is perpendicular to the groove structures) is collected and converted into surface waves by the periodical linear grooves 2010, which may then may be recoupled into propagating light through the central aperture 2010.

Figure 33A:
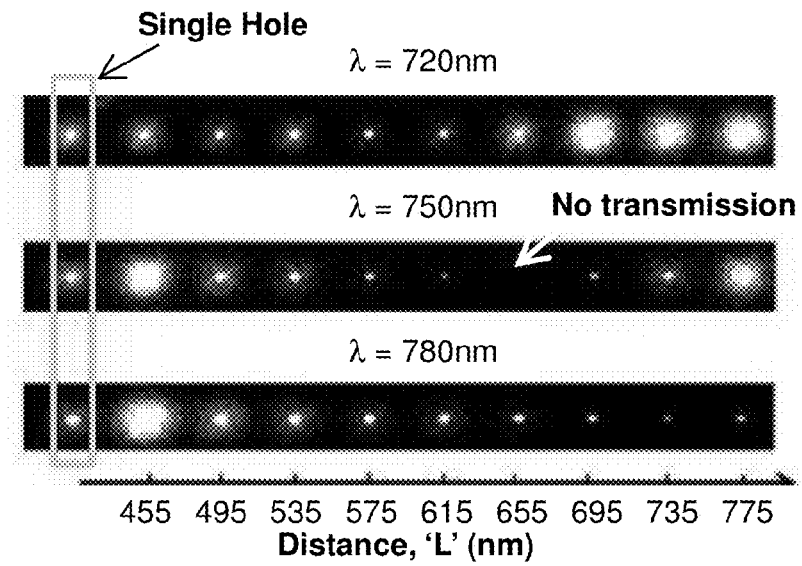
FIG. 33A is a diagram of measured optical transmission images through the central aperture of a pixel of nine SWEDA-based polarization sensors with different distances, 'L,' and through a reference simple single hole under normal incidence illumination for three wavelengths: λ=720 nm, λ=750 nm and λ=780 nm, according to an embodiment of the invention.

FIG. 33A includes measured optical transmission images through the central aperture 2010 of a pixel of nine SWEDA-based polarization sensors 2512 with different distances, 'L,' and through a reference simple single hole under normal incidence illumination for three wavelengths: λ=720 nm, λ=750 nm and λ=780 nm, according to an embodiment of the invention. FIG. 33A shows the sixth SWEDA-based polarization sensor 2700 at λ=750 having a transmission through the central aperture 2710 of close to zero, according to an embodiment of the invention. This shows that the surface wave assisted optical component and the direct transmission component at the central aperture 2710 can cancel or approximately cancel each other, resulting in near-zero transmission under uniform TM illumination.

Figure 33B:
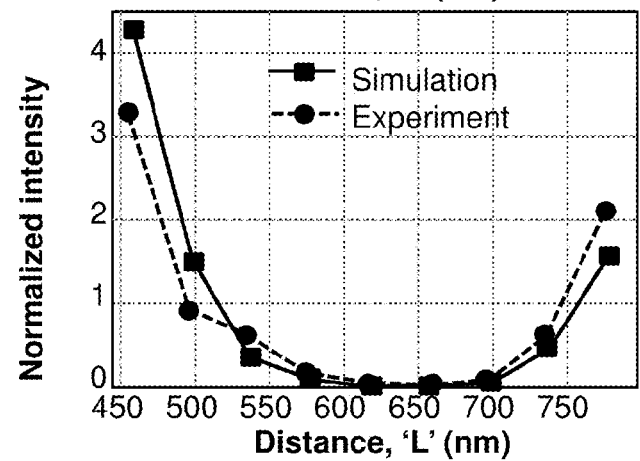
FIG. 33B is a graph including the experimentally measured normalized optical transmission intensity signals through the central aperture of pixels of different SWEDA-based polarization sensors having different distances, 'L,' ranging from 455 nm to 775 nm (left to right), according to an embodiment of the invention.
Figure 33C:
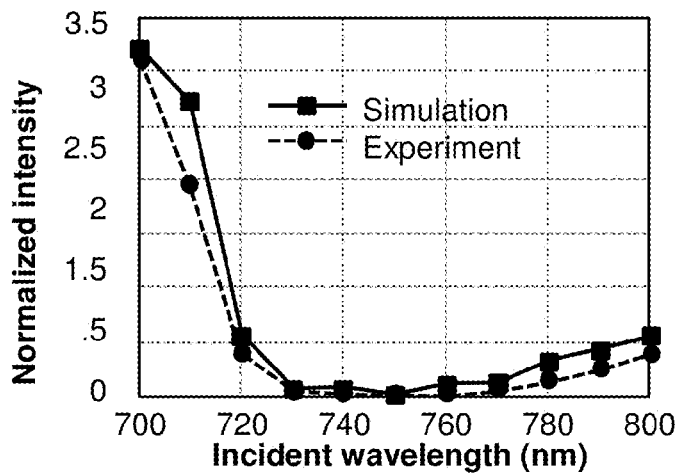
FIG. 33C is a graph including the measured (experimental) normalized optical transmission intensity signals for the optimized SWEDA-based polarization sensor having a distance, 'L,' of 655 nm at different incident wavelengths, according to an embodiment of the invention.

FIG. 33B is a graph including the experimentally measured normalized optical transmission intensity signals through the central aperture 2010 of pixels of different SWEDA-based polarization sensors 2512 having different distances, 'L,' ranging from 455 nm to 775 nm (left to right), according to an embodiment of the invention. The graph in FIG. 33B also includes the simulated normalized intensities for comparison. The measured and simulated normalized intensities from the SWEDA-based polarization sensors 2512 of FIG. 33B were normalized by the intensity of a simple single hole (signal from the single hole was set to unity). Based on the graph, the SWEDA-based polarization sensor 2512 having a distance, 'L,' of 655 nm appears to have the lowest normalized intensity. The measured suppression factor for this optimized SWEDA-based polarization sensor 2512 is 5080. FIG. 33C is a graph including the measured (experimental) normalized optical transmission intensity signals for the optimized SWEDA-based polarization sensor 2512 having a distance, 'L,' of 655 nm at different incident wavelengths, according to an embodiment of the invention.

Figure 34A:
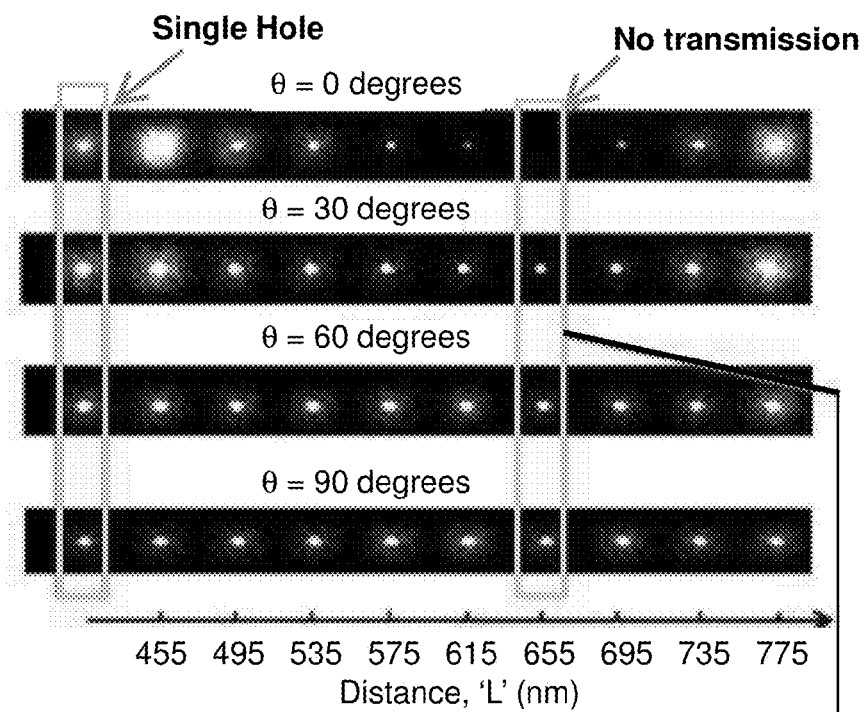
FIG. 34A are measured optical transmission images through the central aperture of a pixel of nine SWEDA-based polarization sensors with different distances, 'L,' and through a reference simple single hole, for four polarization angles: θ=0, 30, 60, and 90 degrees, according to an embodiment of the invention.
Figure 34B:
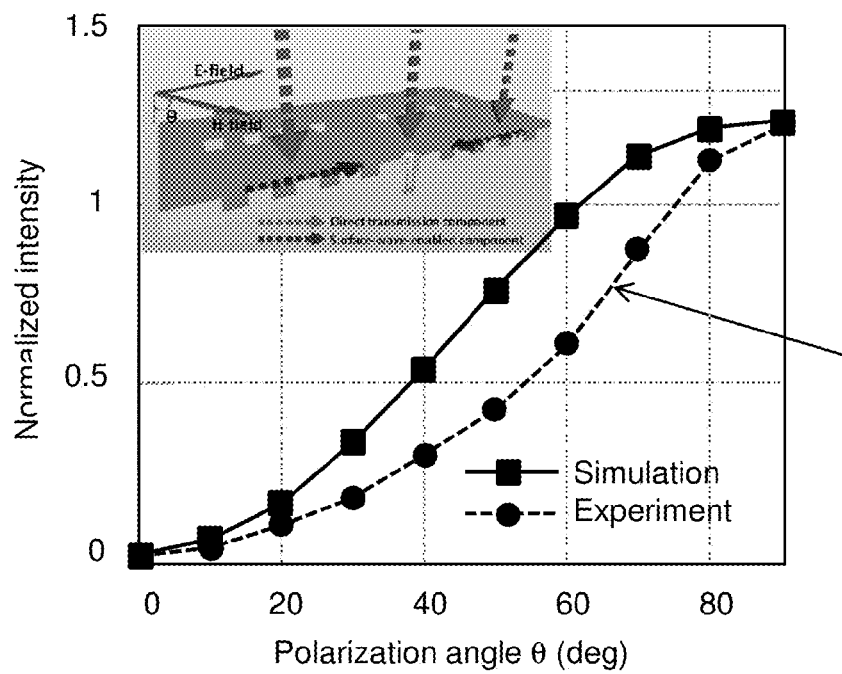
FIG. 34B is a graph of the experimentally measured normalized optical transmission signals through the central aperture of the SWEDA-based polarization sensor having a distance, 'L,' of 655 nm for different polarization angles, θ, according to an embodiment of the invention.

FIG. 34A are measured optical transmission images through the central aperture 2010 of a pixel of nine SWEDA-based polarization sensors 2512 with different distances, 'L,' and through a reference simple single hole, for four polarization angles: θ=0, 30, 60, and 90 degrees, according to an embodiment of the invention. FIG. 34B is a graph of the experimentally measured normalized optical transmission signals through the central aperture 2010 of the SWEDA-based polarization sensor 2512 having a distance, 'L,' of 655 nm for different polarization angles, θ, according to an embodiment of the invention. The measured polarization extinction ratio for TE and TM incidence is 6100.

In FIGS. 33A and 33C, the surface wave assisted optical component and the direct transmission component at the central aperture 2710 of a SWEDA-based polarization sensor 2512 cancel each other resulting in near-zero transmission under uniform TM illumination at λ=750. On the other hand, the surface wave coupling efficiency for TE (transverse electric) polarized light is much smaller than for the TM wave. Since the destructive interference condition (i.e. near-zero transmission) depends on an exact or nearly exact balance of the surface wave assisted optical component and the direct transmission component, a small change in the surface wave assisted component can disrupt the destructive interference condition and permit significant light transmission through the aperture 2710 in the TE case. This is shown in FIG. 34B where a small change in the polarization angle, θ in the graph causes significant change in the intensity of light transmitted thought the central aperture 2010. The observed selective ratios for two orthogonal polarization states is 6100, which is about 2 orders of magnitude larger than the previous results "Theory of optical transmission through elliptical nanohole arrays," Phys. Rev. B 76, 085409 (2007). Since small changes in the polarization angles, θ can cause large changes in intensity, the SWEDA-based polarization sensor 2512 of embodiments is highly sensitive to changes in polarization angles.

The SWEDA-based polarization sensor 2512 of embodiments can effectively act as an interferometer that operates on the principle of exact destructive interference. That is, minor changes to the polarization angle of the incident light can disrupt the destructive interference condition and cause large changes in the measured intensity of light transmitted through the central aperture. Each pixel of the SWEDA-based polarization sensor 2512 can measure a polarization angle based on the intensity of light received and measured through the central aperture 2710 by the light detector layer 2530. For example, a SWEDA-based polarization sensor 2512 can be calibrated to determine a calibration curve of the measured intensity of light at different polarization angles of incident light. The SWEDA-based polarization sensor 2512 can then be used to measure a polarization angle based on the calibration curve. As the overall size of this interferometer is small (~5 microns) and fabricatable on a single substrate (e.g., metal substrate), this structure has excellent stability and can be directly fabricated onto each pixel of the conventional CCD or CMOS sensor 2531 (shown in FIG. 28B). It is also worth noting that there is in principle no theoretical limit to how close the SWEDA-based polarization sensor's 2512 polarization-selective ratio can approach infinite.

V. Additional Surface Wave Assisted Structures and Systems (e.g., Pixel-Level Surface Wave Assisted Devices)

Additional surface wave assisted structures and systems (e.g., pixel-based devices) for specific applications are described in this Section. One example of a surface wave assisted structure is a pixel-level optical-transfer-function (OTF) design based on a surface-wave-interferometry aperture (SWIA) structure. A SWIA structure can refer to an aperture layer having an aperture and a plurality of (concentric) circular grooves around the central aperture. The plurality of circular grooves is defined in the aperture layer or in a separate layer of the SWIA structure. A SWIA-based sensor pixel sensor can refer to a SWIA structure lying over a light detector layer such as a CMOS light detector array. Another example of a surface wave assisted system is a grating structure system that can be used for spectral imaging. Each pixel of the grating structure system has a grating structure designed to provide resonance for a specific wavelength of light to a corresponding light detecting element.

A. OTF Design of Surface Wave Interference Aperture (SWIA) and SWIA-Based Pixel (SWIP)

An OTF characterizes the response of an imaging system as a function of spatial frequency of the input signal. Modification of OTF (sometimes referred to as spatial filtering) is of fundamental importance in modern imaging and vision system designs. In conventional systems, the implementation of spatial filtering is typically achieved by inserting a mask (phase, amplitude or both phase and amplitude) into the Fourier plane of a 4f system, or by using a spatial light modulator (SLM) to modify the phase and amplitude in real time. While these implementation methods allow for good control of OTF, these conventional methods come with the associated cost of sophisticated bulk optical arrangement.

The design of OTF can be performed in a compact format using SWIA structure(s) 3000 of embodiments. The SWIA structures 3000 of these embodiments can make use of surface wave interference to modify the spatial response of the central aperture to create different types of OTF designs (e.g., notch, highpass, and lowpass filters, etc.). The SWIA structures 3000 can act as a compact interferometer where the incident light within a certain range of spatial frequency will be reflected back due to destructive interference. In these embodiments, the design of the OTF can be achieved by modulating the transmission of the SWIA structure 3000. The SWIA structure 3000 can also be directly incorporated at the pixel level onto a modern image sensor such as a CMOS active pixel sensor design, creating a scheme for on-chip OTF design that is more compact and robust than those of conventional systems having bulk optics. Some details of SWIA structures of embodiments can be found in Zheng, G., Want, Yingmin, Yang, Changhuei, "*Pixel level optical-transfer-function design based on surface-wave interferometry aperture*," Optics Express, Vol. 18, No. 16, Aug. 2, 2010, p. 16499, which is hereby incorporated by reference in its entirety for all purposes. OTF designed SWIA sensors can be used in numerous applications such as optofluidic microscopy, wavefront detection, darkfield imaging, computational photography, etc.

Figure 35:
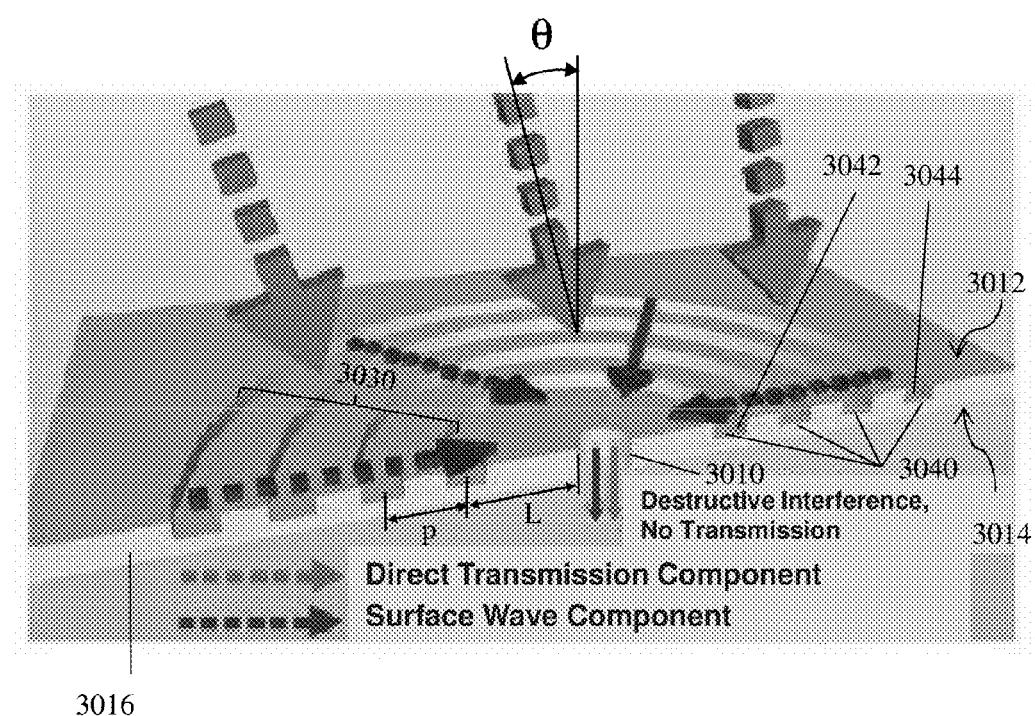
FIG. 35 is a schematic drawing of a SWIA structure, according to an embodiment of the invention.

FIG. 35 is a schematic drawing of a SWIA structure 3000, according to an embodiment of the invention. The SWIA structure 3000 includes an opaque or semi-opaque aperture layer 2003 having a first surface 2004 and a second surface 2006. The aperture layer 2003 has a central aperture 3010. In FIG. 35, the aperture layer 2003 also defines a plurality of circular grooves 2030 around the central aperture 3010. In other embodiments of the SWIA structure 3000, the plurality of circular grooves 2030 may be defined in a separate layer from the aperture layer 2003. Although the plurality of circular grooves 2030 is shown in FIG. 35 to be defined only in the first surface 2004, the plurality of circular grooves 2030 can be defined in the second surface 2006 or in both first and second surfaces 2004 and 2006 in other embodiments. In FIG. 35, the plurality of circular grooves 2030 includes four circular grooves 2020 of a constant rectangular cross-sectional shape and constant dimensions. The plurality of circular grooves 2030 can have another suitable number of circular grooves 2020 and/or another cross-sectional shape in other embodiments. The plurality of circular grooves 2030 includes an innermost groove 2022 and an outermost groove 2024. The period between adjacent grooves 2020 in the plurality of circular grooves 2030 can be constant or variable, and can have any suitable value. In FIG. 35, the plurality of circular grooves 2030 is shown to have a constant value period, 'p' between all adjacent grooves 2020 in the plurality of grooves 2030. The SWIA structure 3000 also has a distance, 'L,' defined between the outside of the aperture 2010 and the centerline of the innermost groove 2022.

SWIA structures 3000 of embodiments differ from other surface wave assisted aperture structures mainly in two aspects. First, SWIA structures 3000 employ a relatively large central aperture 3020 and smaller groove period, p, in comparison with some other surface wave assisted aperture structures of embodiments. Some examples of suitable sizes of the central aperture of the SWIA structures 3000 are in the range of 250-350 nm. Some examples of suitable periods of the SWIA structures 3000 are in the range of 500-800 nm. The large central aperture 3010 can increase the direct light transmission component. The smaller groove period, p, can reduce the surface wave coupling. Through judicious design adjustment of the size, s, of the central aperture 3010 and the period of the grooves, p, a SWIA structure 3000 can be designed to have a direct transmission component equal to the strength of the surface wave component. Such a design leads to a strong interference between these two components, providing a means for modifying the spatial response of the aperture. Second, SWIA structures 3000 of embodiments are designed for a given OTF based primarily on adjusting the phase difference between the direct transmission and surface wave induced components.

FIG. 35 illustrates the working principle of the SWIA structure 3000. In FIG. 35, an incoming plane wave illuminates the SWIA structure with a certain incident angle, $\theta$. The incoming incidence light (with a certain transverse wave vector) is coupled into surface waves by the plurality of circular grooves 2030. In FIG. 35, there are two wave components at the center of the opening of the aperture 3010: 1) the direct transmission component of the incoming wave; and 2) the surface wave component induced by the plurality of circular grooves 2030. The surface wave component interferes with the direct transmission component modifying the spatial response. A destructive interference point can be met by matching the amplitude of the direct transmission component through the aperture 3010 and the surface wave induced component, and arranging the phase shift between the two components to be 180 degrees. Phase shift is primarily governed by the distance, L. The destructive interference point can result in zero transmission through the aperture 3010 and can produce a node in the OTF curve. The principle of the OTF designed SWIA structure 3000 is based on tuning this destructive interference point by adjusting the spacing, L, between the central aperture 3010 and the innermost groove 2022, and/or other suitable design parameters. For a conventional circular hole, only a direct transmission component can be induced and the spatial response of the transmission follows the cosine function as a first order approximation.

FIG. 35 also shows that OTF design can be accomplished in a compact form using a SWIA structure 3000. The SWIA structure 3000 makes use of surface wave interference to modify the spatial response of a conventional aperture. The SWIA structure 3000 can also be directly incorporated onto a light detector array (e.g., CMOS active pixel sensor array) for a pixel-level design. The pixel-level design creates a new scheme for on-chip OTF engineering that is much more compact and robust than those previously achievable options with bulk optical arrangements.

In embodiments, the design parameters of a SWIA structure 3000 can be adjusted (tuned) to generate a spatial response of a selected OTF design such as a notch filter, a highpass filter, or a lowpass filter. In essence, the SWIA structure 3000 acts as a compact interferometer where the incident light within a certain range of spatial frequency will be reflected back due to destructive interference. For a highpass OTF design, the spacing, L, between the aperture 3010 and the innermost groove 2024 can be adjusted so that the two components (direct transmission component and surface wave component in FIG. 35) are 180 degrees out of phase from each other under light incidence with a low spatial frequency (small incidence angles). As such, the two components may destructively interference and result in no light transmission through the aperture 3010 in the presence of low spatial frequency light incidence (i.e. creating a node at the spatial-response curve). The same principle applies to lowpass and notch OTF filter designs. By further altering the distance, L, the destructive interference point can be moved out to create a notch filter and a low-pass OTF filter. The notch, highpass, and lowpass OTF filter designs are based on the response of a single simple hole.

Figure 36:
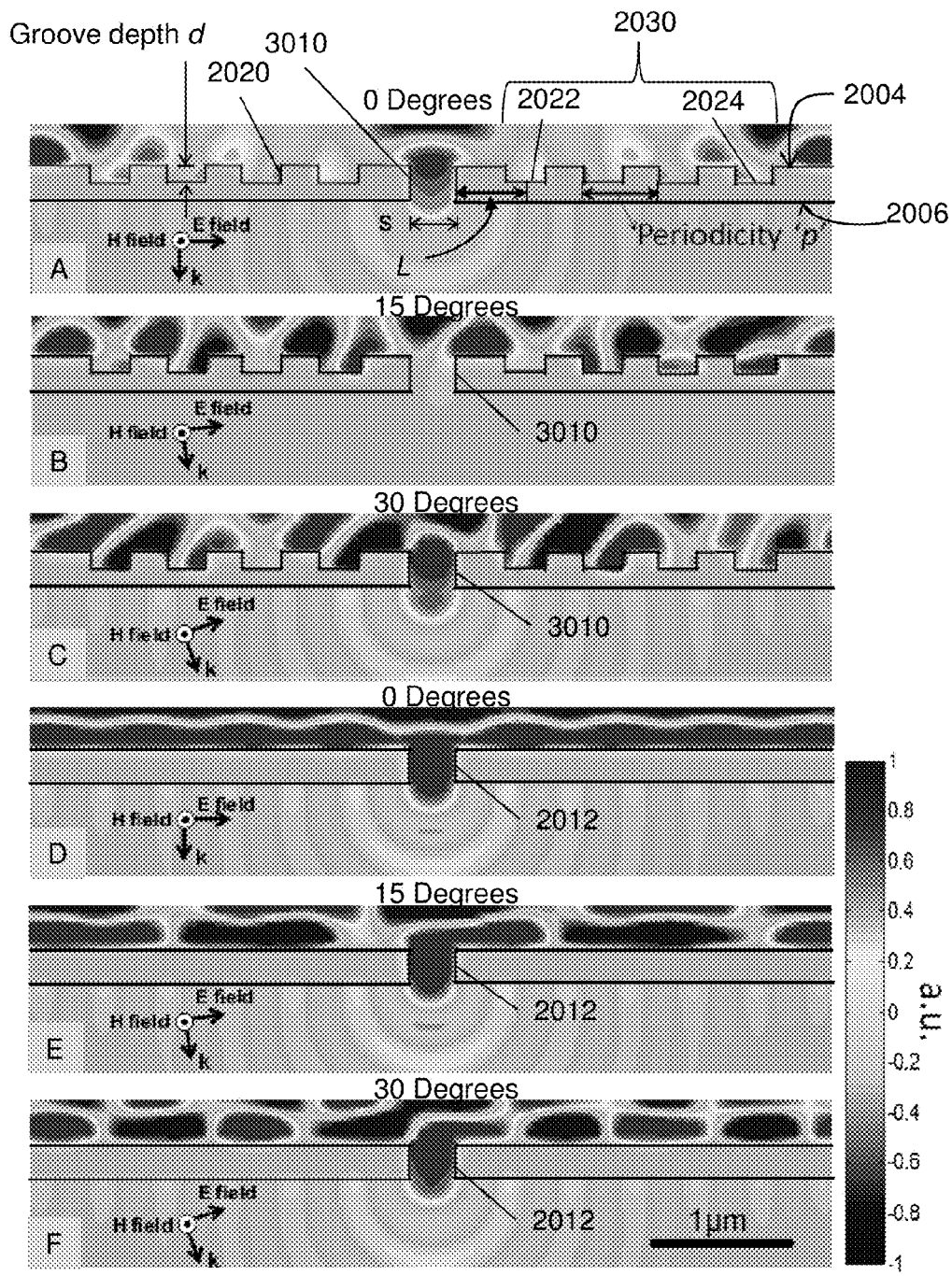
FIGS. 36A, 36B, and 36C illustrate a set of simulations of the real part of the magnetic field distributions around the SWIA structure with the optimal design parameters under 0, 15, and 30 degrees light incidence, according to the embodiment.
FIGS. 36D, 36E, and 36F are simulations of the distributions around a single hole under 0, 15, and 30 degrees light incidence for reference.

In one embodiment, the design parameters of a SWIA structure 3000 may be adjusted to optimize the OTF designed SWIA structure 3000 to be a notch filter where a 15 degree incidence produces a node in the OTF curve. FIGS. 36(a), 36(b), and 36(c) illustrate a set of simulations of the real part of the magnetic field distributions around the SWIA structure 3000 with the optimal design parameters under 0, 15, and 30 degrees light incidence, according to the embodiment. The simulations were performed at a nominal wavelength, $\lambda=740$ nm. The parameters of the SWIA structure 3000 are: L=540 nm, p=560 nm, aperture layer thickness=340 nm, aperture diameter, s=300 nm, groove depth=140, and refractive index of dielectric substrate is 1.5. FIGS. 36D, 36E, and 36F are simulations of the distributions around a single hole under 0, 15, and 30 degree light incidence for reference.

As shown in FIGS. 36A, 36B, and 36C, the transmission of the SWIA structure 3000 with optical design parameters drops to zero at 15-degree incidence. Since different incident angles correspond to different spatial frequency components, the SWIA structure 3000 in FIGS. 36A, 36B, and 36C is a notch OTF filter where the 15-degree incidence component produces a node in the OTF curve. Compared to the case of the single hole without grooved structures shown in FIGS. 36D, 36E, and 36F, the SWIA structure 3000 provides a sharp gradient response of the incident angles at the region from 0 to 15 degrees. This property of the SWIA structure 3000 can be used in wavefront detection, where the intensity can be mapped to the incidence angle of the incoming light field above the aperture 3010. Since the node of the OTF curve can be changed by adjusting the distance, L, between the central hole 3010 and the innermost groove 2022, the design of a lowpass and highpass OTF filter can be accomplished by tuning the node to the desired spatial frequency component by adjusting the distance, L, of the SWIA structure 3000.

Figure 37A:
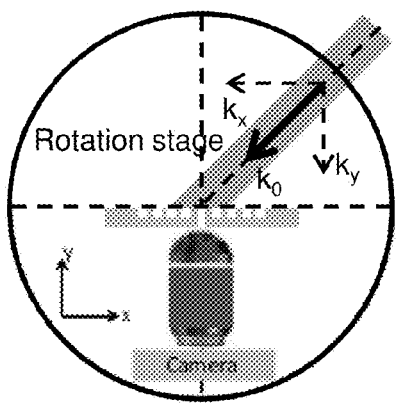
FIG. 37A is an experimental set up for characterizing the spatial response of the SWIA structure, according to an embodiment of the invention.

FIG. 37A is an experimental set up for characterizing the spatial response of the SWIA structure 3000, according to an embodiment of the invention. A Ti-Sapphire laser was used as the illumination source. The transmission of the proposed aperture is collected by a 20× (0.5 NA) objective and the whole detection set up is assembled on a motorized rotation stage to measure the spatial response of the aperture with different transverse wave vector of the incident light.

Figure 37B:
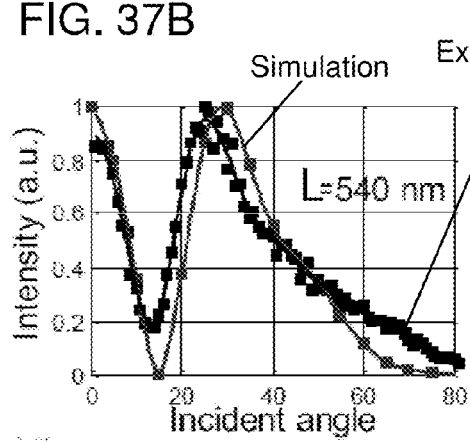
FIG. 37B is a graph of the simulated and experimental spatial response of a notch filter designed SWIA structure of an embodiment.
Figure 37C:
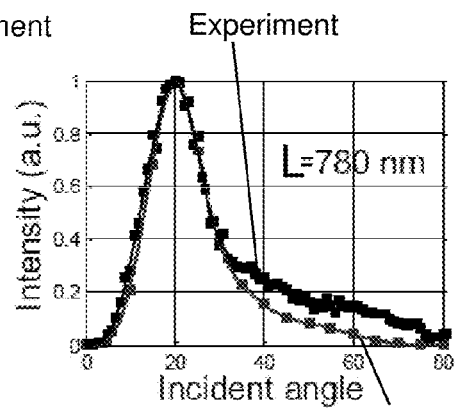
FIG. 37C is a graph of the simulated and experimental spatial response of a highpass filter designed SWIA structure, according to an embodiment.
Figure 37D:
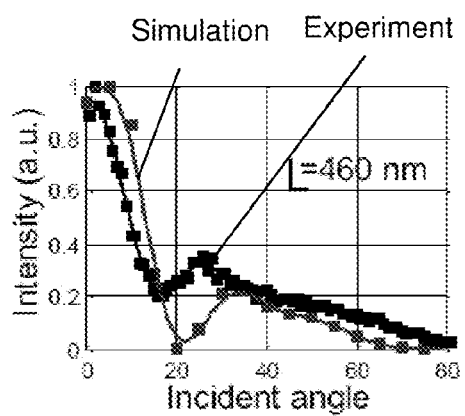
FIG. 37D is a graph of the simulated and experimental spatial response of a lowpass filter designed SWIA structure according to an embodiment.
Figure 37E:
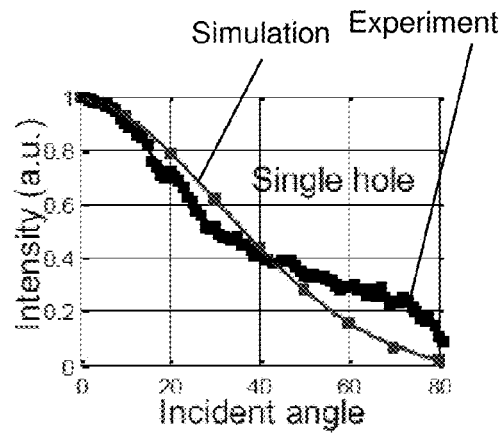
FIG. 37E is a graph of the simulated and experimental spatial response of a single hole without a groove structure for reference.

FIGS. 37B, 37C and 37D are graphs of the experimental and simulated spatial response of three fabricated SWIA structures 3000 with different distances, L=540 nm, 780 nm, and 460 nm respectively, according to an embodiments of the invention. The three SWIA structures 3000 are designed as notch, lowpass, and highpass filters respectively. FIG. 37E is the measured and simulated spatial response of a single hole without a groove structure for reference. The measured experimental spatial responses shown in FIGS. 37B-D were measured using the experimental set up in FIG. 37A. In the simulation experimental set up, the transmission through the OTF-designed SWIA structures 3000 was calculated by integrating the Poynting vector over a $6\lambda \times 6\lambda$ region ($0.85\lambda$ beneath the aperture). As shown, the experimental results appear to be in good agreement with the simulated results.

The different filter designs (notch, lowpass, and highpass filter designs) of the SWIA structures 3000 may have specific applications due to the properties of their exhibited spatial responses and the fundamental compactness and cost-effectiveness of their construction. For example, a notch filter designed SWIA structure 3000 may have a property of its spatial response that can be used for wavefront detection. As another example, a highpass OTF designed SWIA structure 3000 may have a property of its spatial response that can be used for darkfield imaging.

FIG. 37B illustrates the spatial response of a notch filter designed SWIA structure 3000 of an embodiment. The illustrated spatial response has a property that can be used for wavefront detection. As shown in FIG. 37B, the transmission of a notch filter design of a SWIA structure 3000 drops from a maximum to almost zero from 0 to 15-degree incidence. Compared with the conventional single aperture where the gradient of transmission versus incident angle is close to zero at normal incidence, the transmission through the notch filter designed SWIA structure 3000 may have a relatively large gradient near zero degree incidence as shown in FIG. 37B. The property of having a relatively large gradient of transmission near zero degree incidence can be used for wavefront detection. In a wavefront detection scheme, a SWIA-based pixel sensor pixel with a notch filter designed SWIA structure 3000 such as the one in FIG. 37B can have another simple aperture fabricated close (e.g., at about 2 μm) to the central aperture 3010. The two apertures are placed in close proximity so that the intensity of incoming light does not dramatically change between the two apertures. The wavefront information can be decomposed from the intensity information measured through the apertures. First, the local intensity through the simple aperture and the central aperture 3010 can be measured. The intensity through the central hole 3010 can be normalized by the intensity through the simple aperture. The normalized value can then be mapped to a pre measured calibration curve to get the incident angle of the incoming light. Since a SWIA structure 3000 can be fabricated on a sensor chip, the wavefront detection process can be done on a conventional sensor chip with a high spatial sampling rate (at least two orders of magnitude larger than the microlens array used in a conventional Shack-Hartmann wavefront sensor).

FIG. 37C illustrates the spatial response of a highpass filter designed SWIA structure 3000, according to an embodiment. The properties of the spatial response show that the highpass filter designed SWIA structure 3000 can be used in darkfield imaging. As shown in FIG. 37C, the central aperture 3010 of this design captures the high frequency components contributed by an object's scattering. The low spatial frequency background illumination is reflected back by the destructive interference. Also, the maximum transmission occurs at the normalized spatial frequency ($k_x/k_0$) of 0.3. This highpass filter designed SWIA structure 3000 can act as an optical antenna, with its main lobe of receiving pattern oriented at certain angle. The angle-oriented directivity of the highpass filter designed SWIA structure 3000 may have equivalence to using a ring aperture in the lens system in multi-aperture photography. With different main lobe orientations, the highpass filter designed SWIA structure 3000 can also find some application in depth of field extrapolation and refocusing.

FIG. 37D illustrates the spatial response of a lowpass filter designed SWIA structure 3000 according to an embodiment. As shown in FIG. 37D, the central aperture 3010 of this design captures low spatial frequency components and reflects high spatial frequency components. In the illustrated example, the full width at half maximum (FWHM) of the OTF curve is about 20 degrees, which is only 30% percent of the FWHM of the single hole aperture shown in FIG. 37E. The smaller the FWHM of the OTF curve means the smaller the collection angle, and thus, a smaller f-number of the imaging system and a larger depth of field. Also, a small value of FWHM may be critical for design of aperture-based imaging devices where apertures are used as light collection units. One example of such an aperture-based imaging device is an OFM, where the resolution can degrade as the height between the sample and the aperture increases. Since the FWHM value of the proposed aperture is only 30% of the conventional single hole, the resolution of an OFM or other such aperture-based imaging device can be increased by tan(60 degrees)/tan(20 degrees)≈5 folds (provided that it is still in the diffraction limited region).

Figure 38:
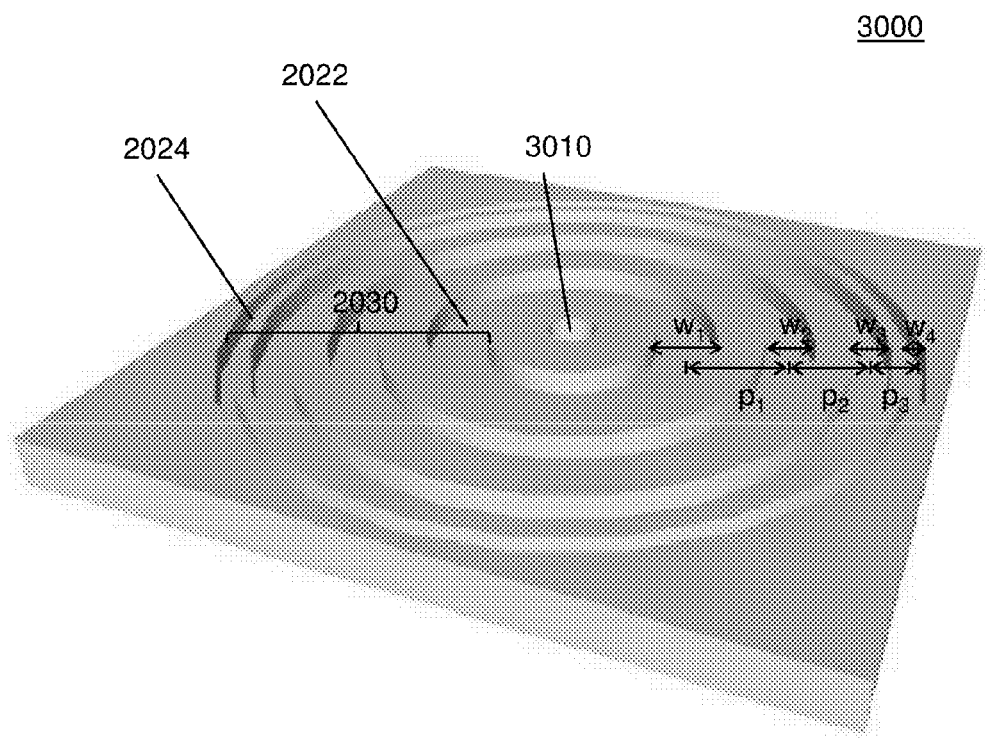
FIG. 38 is an schematic drawing of a broadband OTF designed SWIA structure that has a gradually period changing SWIA structure, according to an embodiment of the invention.

In embodiments, a SWIA structure 3000 may be designed for multibeam interference to generate multiple destructive interference points in the OTF curve. These embodiments are designed with mulitbeam interference points for a larger working bandwidth than those with a single interference point in a two beam interference scheme. These broadband OTF designed SWIA structures 3000 may include a plurality of grooves 2030 having grooves 2010 with multiple periods. Any suitable number of periods can be used (e.g., 2, 3, 4, 5, etc.). FIG. 38 is an illustrated example of a broadband OTF designed SWIA structure 3000 that has a gradually period changing SWIA structure 3000, according to an embodiment of the invention. The SWIA structure 3000 has a plurality of grooves 2030 with an innermost groove 2022 and an outermost groove 2024. The plurality of grooves 2030 have groove periods, $p_1$, $p_2$, and $p_3$ that gradually decrease from the innermost groove 2022 to the outermost groove 2024. Similar to a multilayer thin film filter design of conventional filters, the multibeam interference scheme in FIG. 38 may provide more freedom on bandwidth control.

B. Grating Structure System for Spectral Imaging

Conventional spectral imaging techniques typically rely on filters or interferometers combined with scanning or subsampling to record a spectral image. This can lead to inefficient use of the incoming light and/or long recording times.

Figure 39A:
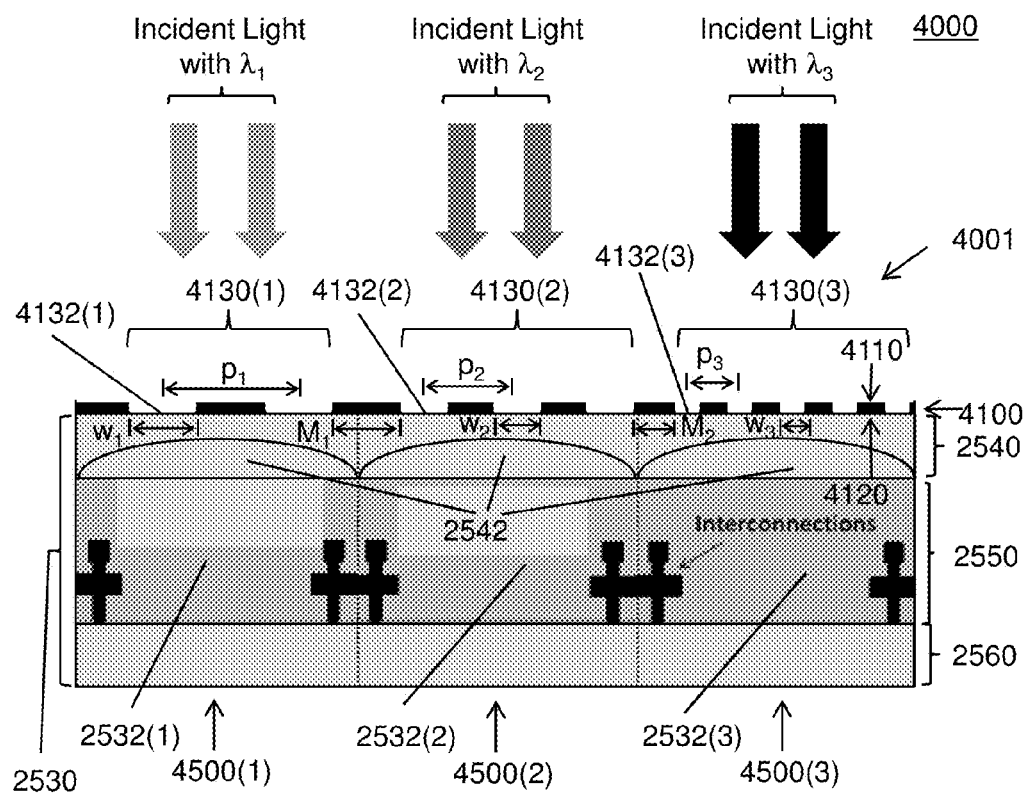
FIG. 39A is a schematic drawing of across sectional view of a portion of a grating structure system for spectral imaging, according to an embodiment.

FIG. 39A is a schematic drawing of a cross sectional view through of a portion of a grating structure system 4000 for spectral imaging, according to an embodiment. The grating structure system 4000 of the illustrated example may provide surface wave assisted direct recording of spectral image cubes of data in a single exposure.

In FIG. 39A, the grating structure system 4000 includes a multi-layer body 4001 comprising a grating layer 4100 and a light detector layer 2530. In this cross-sectional view, the grating layer 4100 includes a first grating structure 4130(1), a second grating structure 4130(2), and a third grating structure 4130(3). The light detector layer 2530 comprises three light detecting elements 2532(1), 2532(2), and 2532(3) corresponding to the grating structures 4130(1), 4130(2), and 4130(3) respectively. The light detector layer 2530 is a multilayered structure comprising a transparent layer 2540 (e.g., a PMMA layer) having optional microlenses 2542, a dielectric stack layer 2550 having interconnections, and a photosensitive layer 2560 (e.g., silicon substrate layer). The multi-layer body 4001 may omit layers or include other layers in other embodiments. For example, one embodiment may include a transparent layer (e.g., layer(s) of transparent material or vacuum or gas-filled space) located between the light detector layer 2530 and the grating layer 4100. For example, one embodiment may include a transparent protective layer located outside the grating layer 4100 of FIG. 39A. As another example, one embodiment may include an additional grating layer 4100 located on the other side of the light detector layer 2530. The grating structure system 4000 also includes an x-axis, a y-axis (not shown), and a z-axis normal to the x-axis. The y-axis is normal to the x-z plane.

A grating layer 4100 can refer to an opaque or semi-opaque layer having at least one grating structure 4130. The grating layer 4100 can be made of any suitable material(s). For example, the grating layer 4100 may be a metallic layer (e.g., a thin gold layer). In another example, the grating layer 4100 may consist of a metallic layer over a transparent plate (e.g., a glass plate). The dimensions (thickness, length, width) of the grating layer 4100 can have any suitable values. For example, the thickness of the grating layer 4100 can be in the range of 10-40 nm. In some cases, the type of material used in the grating layer 4100 can affect roughness of the grating layer 4100 and the sharpness of the features in the grating layer 4100, which can affect the properties of the surface waves induced by the grating structures 4130. In some cases, the grating layer 4100 may be a planar thin film.

A grating layer 4100 may include any suitable number (e.g., 1, 2, 3, etc.) of grating structures 4130. A grating structure 4130 can refer to a checkerboard or other suitable pattern of periodically placed elements 4132 of removed material from the grating layer 4100. Each grating structure 4130 can have any suitable number of periodically located grating elements 4132 with period, p, and dimensions (e.g., depth, d, width, w, length, l, etc.) of suitable values. Each periodic element 4132 may be of any suitable shape such as square, bowtie, C-shaped, H-shaped, etc.

In FIG. 39A, the cross-sectional view of the grating layer 4100 shows three grating structures 4130: a first grating structure 4130(1), a second grating structure 4130(2), and a third grating structure 4130(3). The first grating structure 4130(1) is shown to have two grating elements 4132(1) having a width, $w_1$ and a period, $p_1$ along the x-axis. The second grating structure 4130(2) is shown to have three grating elements 4132(1) having a width, $w_2$ and a period, $p_2$ along the x-axis. The third grating structure 4130(3) is shown to have five grating elements 4132(3) having a width, $w_3$ and a period, $p_3$ along the x-axis. The grating layer 4100 in FIG. 39A also includes a distance, $M_1$, between the first grating structure 4130(1) and the second grating structure 4130(2). The grating layer 4100 also includes a distance, $M_2$, between the second grating structure 4130(2) and the third grating structure 4130(3). In the illustrated example, the periods, p, widths, w, and distances, M, gradually decrease in the x-direction.

In FIG. 39A, the grating structure system 4000 includes a first pixel 4500(1), 4500(2), and 4500(3). Each pixel 4500 includes a grating layer 4100 (e.g., thin metal film) with a grating structure 4132 of a single period, p, over a corresponding light detecting element 2532 (e.g., image sensor pixel). The grating structure 4132 of each pixel 4500 is designed to induce surface waves that constructively interfere with incoming light of a select wavelength based on the design parameters (e.g., period, p) of the grating structure 4132. In this way, each pixel 4500 acts as an antenna for incoming light of a select wavelength. The pixels 4500 in the grating structure system 4000 have different grating structures 4130 designed to induce surface waves that constructively interfere with light of different wavelengths. By applying a grating layer 4100 on top of the light detecting elements 2532, incoming light is converted to surface wave(s) and can then be separated according to wavelengths by the different grating structures 4130, before being recoupled to light through individual light detecting elements 2532.

Figure 39B:
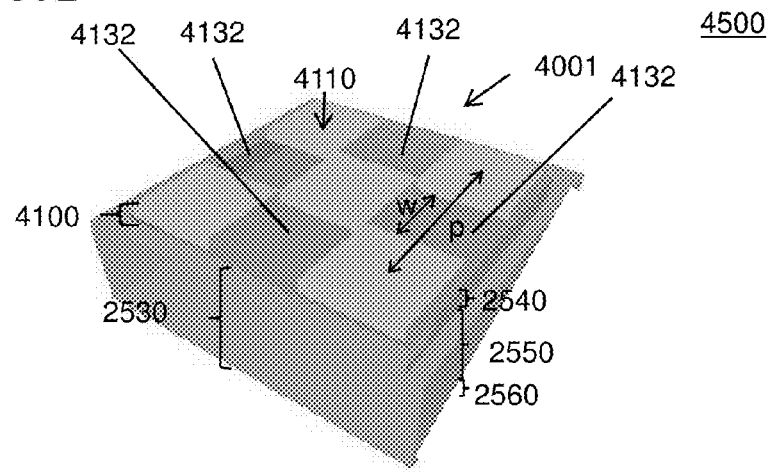
FIG. 39B is a schematic drawing of a pixel of a grating structure system for spectral imaging, according to an embodiment.

FIG. 39B is a schematic drawing of a pixel 4500 of a grating structure system 4000 having a square grating structure 4100 with a single period, p, according to an embodiment. The pixel 4001 includes a grating layer 4100 and a light detector layer 2530 having a single light detecting element 2532. The grating layer 4100 includes a checkerboard pattern of five periodically located rectangular elements 4132. The rectangular elements 4132 are defined in the outer surface 4110. The rectangular elements 4132 have a width, w and a period, p.

The grating structure system 4000 employs field enhancement of the surface wave resonance of light of a particular wavelength within each pixel 4500. Surface waves can be described as light waves trapped at the interference between a metal (e.g., grating layer) and the dielectric stack layer 2550. The dispersion relation of the surface waves is different from the free space propagating light, and thus, a periodic grating structure may be used to enhance coupling of the free space propagating light into surface waves. In a pixel 4500 of a grating structure system 4000, the incoming light is collected and coupled into surface waves by a resonance process. As such, the grating structure 4130 can increase the efficiency of the light collection due to the many passes the light makes within the resonator, increasing the amount of time light spends within the detector active region, and therefore enhance the probability of light detection.

In other embodiments, a grating structure system 4000 may include multiple grating layers 4100. For example, in a broadband application, a grating structure system 4000 may include multiple superimposed grating layers 4100 with grating structures 4106 having different periods, p.

Most conventional many-band spectral imagers use some form of scanning, which leads to spectral artifacts for non-stationary scenes or loss of throughput or both. The in-plane photon-sorting capacity of surface waves of the grating structure system 4000 offers opportunities for improvement in spatial resolution, band registration, band count, throughput, simultaneity or simplicity, depending on with which technology it is compared. There is a potential for extending the concept to more spectral bands, especially into the near-infrared where surface wave resonances become sharper with higher quality factors. Improvements are also possible in the delineation between different sets of light collecting structures to obtain better defined pixel shapes in the spectral image. Furthermore, it is important to note that the antenna effect of the grooved structure permits reduction in the underlying light detecting element size, with potential gains in speed and chip dimensions. Mass production of photon-sorting structures should be feasible using current fabrication techniques, which involve structuring on scales of tens of nanometers.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

A recitation of "a", "an" or "the" is intended to mean "one or more" unless specifically indicated to the contrary.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

All patents, patent applications, publications, and descriptions mentioned above are hereby incorporated by reference in their entirety for all purposes. None is admitted to be prior art.

What is claimed is:

1. A surface wave assisted system comprising:
   an aperture layer having a surface and an aperture; and
   a plurality of grooves around the aperture, the plurality of grooves configured to generate an optical transfer function at the aperture by inducing a surface wave for destructively interfering with transmission of light of a range of spatial frequency at the aperture; and
   a light detector layer, wherein the aperture layer is disposed on the light detector layer.

2. The surface wave assisted system of claim 1, wherein the plurality of grooves is defined in the surface of the aperture layer.

3. The surface wave assisted system of claim 1, wherein the plurality of grooves is defined in a transparent layer disposed on the aperture layer.

4. The surface wave assisted system of claim 1,
   wherein the plurality of grooves comprises an innermost groove and an outermost groove, and
   wherein the optical transfer function is associated with a distance between the innermost groove and the outermost groove.

5. The surface wave assisted system of claim 1, wherein the optical transfer function is a notch filter.

6. The surface wave assisted system of claim 1, wherein the optical transfer function is a highpass filter.

7. The surface wave assisted structure of claim 1, wherein the optical transfer function is a lowpass filter.

8. The surface wave assisted system of claim 1,
   further comprising a simple aperture in the surface;
   wherein the plurality of grooves is further configured to generate a high gradient of transmission at normal incidence; and
   wherein the light detector layer is configured to detect a wavefront based on a measured intensity of light transmitted through the aperture normalized by a measured intensity of light through the simple aperture.

9. The surface wave assisted system of claim 1, wherein the plurality of grooves has a gradually changing period to destructively interfere with light having a broad range of wavelengths.

10. A surface wave assisted polarization sensor comprising:
    an aperture layer having a surface and an aperture;
    a first and second pluralities of linear grooves located on opposite sides of the aperture and configured to induce a surface wave for destructively interfering with transmission through the aperture of light of a polarization angle; and
    a light detector configured to detect the polarization angle by measuring intensity of light transmitted through the aperture, wherein the aperture layer is disposed on the light detector.

11. The surface wave assisted polarization sensor of claim 10, wherein the first and second pluralities of grooves are defined in the surface of the aperture layer.

12. The surface wave assisted polarization sensor of claim 10, wherein the first and second pluralities of grooves are defined in a transparent layer separate from the aperture layer.

13. A surface wave assisted system for spectral imaging, comprising:
 a grating structure configured to induce a surface wave for increasing intensity of light of a wavelength transmitted through the grating structure; and
 a light detecting element configured to receive light transmitted through the grating structure and detect the increased intensity of the light of the wavelength, wherein the grating structure is disposed over the light detecting element.

14. A surface wave assisted darkfield aperture system comprising:
 an aperture layer having a surface and an aperture; and
 a plurality of grooves around the aperture, the plurality of grooves configured to generate a darkfield at the aperture by inducing a surface wave for destructively interfering with direct transmission of a uniform incident light field received by the aperture;
 a light detector adapted to detect light passing through the aperture, wherein the aperture layer is disposed on the light detector.

15. The surface wave assisted darkfield aperture system of claim 14, wherein the plurality of grooves is further configured to constructively interfere with transmission of a non-uniform light field received by the aperture.

16. The surface wave assisted darkfield aperture system of claim 14, wherein the plurality of grooves is defined in the surface of the aperture layer.

17. The surface wave assisted darkfield aperture system of claim 14, wherein the plurality of grooves is in a transparent layer separate from the aperture layer.

18. The surface wave assisted darkfield aperture system of claim 14, further comprising a light detector adapted to detect light passing through the aperture.

19. A broadband surface wave aperture system comprising:
 an aperture layer having a surface and an aperture;
 a first plurality of grooves around the aperture, the first plurality of grooves configured to induce a first surface wave configured to destructively interfere with light of a first range of wavelengths;
 a second plurality of grooves around the aperture, the second plurality of grooves configured to induce a second surface wave configured to destructively interfere with light of a second range of wavelengths different from the first range of wavelengths; and
 a light detector, wherein the aperture layer is disposed on the light detector layer.

20. The broadband surface wave aperture system of claim 19,
 wherein the first plurality of grooves has a first periodicity configured to destructively interfere with light of the first range of wavelengths, and
 wherein the second plurality of grooves has a second periodicity different from the first periodicity, the second periodicity configured to destructively interfere with light of the second range of wavelengths.

21. The surface wave assisted darkfield aperture system of claim 14, wherein the plurality of grooves is further configured to constructively interfere with transmission of a non-uniform light field received by the aperture.

* * * * *